(12) United States Patent
Hagiwara et al.

(10) Patent No.: US 7,569,536 B2
(45) Date of Patent: Aug. 4, 2009

(54) METHOD FOR CONTROLLING SR PROTEIN PHOSPHORYLATION, AND ANTIVIRAL AGENTS WHOSE ACTIVE INGREDIENTS COMPRISE AGENTS THAT CONTROL SR PROTEIN ACTIVITY

(75) Inventors: Masatoshi Hagiwara, 912-8, Naniwa-cho, Hanamigawa-ku, Chiba-shi, Chiba 262-0024 (JP); Takeshi Fukuhara, Tokyo (JP); Masaaki Suzuki, Aichi (JP); Takamitsu Hosoya, Kanagawa (JP)

(73) Assignee: Masatoshi Hagiwara, Chiba (JP)

( * ) Notice: Subject to any disclaimer, the term of this patent is extended or adjusted under 35 U.S.C. 154(b) by 0 days.

(21) Appl. No.: 10/584,482

(22) PCT Filed: Dec. 24, 2004

(86) PCT No.: PCT/JP2004/019393

§ 371 (c)(1),
(2), (4) Date: Mar. 2, 2007

(87) PCT Pub. No.: WO2005/063293

PCT Pub. Date: Jul. 14, 2005

(65) Prior Publication Data

US 2007/0135367 A1    Jun. 14, 2007

(30) Foreign Application Priority Data

Dec. 26, 2003    (JP)    ............................. 2003-435085

(51) Int. Cl.
*A01N 61/00*    (2006.01)
*A61K 51/00*    (2006.01)
*C12N 15/09*    (2006.01)
*C12N 9/12*    (2006.01)

(52) U.S. Cl. ............................. 514/1; 424/9.1; 424/9.2; 435/69.2; 435/194

(58) Field of Classification Search ...................... 514/1, 514/2, 44; 424/9.1, 9.2; 435/6, 69.2, 194
See application file for complete search history.

(56) References Cited

U.S. PATENT DOCUMENTS 5,707,987 A * 1/1998 Nakagawa et al. ...... 514/210.09
2006/0094081 A1* 5/2006 Schubert et al. ............ 435/69.1

FOREIGN PATENT DOCUMENTS

| JP | 1-151593 A | 6/1989 |
| JP | 7-503966 A | 4/1995 |
| JP | 2000-510865 A | 8/2000 |
| JP | 2001-505193 A | 4/2001 |
| JP | 2002-179651 A | 6/2002 |
| WO | WO 02/02524 A1 | 1/2002 |
| WO | WO 02/094796 A2 | 11/2002 |
| WO | WO 2004/096795 | * 4/2003 |

OTHER PUBLICATIONS

Gendelman et al., AIDS, Bol. 4, No. 2, pp. 221-228 (1990).*
Bridge et al., "Adenovirus Early Region 4 and Viral DNA Synthesis," *Virology*. 193:794-801 (1993).
Daub et al., "Identification of SRPK1 and SRPK2 as the Major Cellular Protein Kinases Phosphorylationg Hepatitis B Virus Core Protein," *J. of Virology*. 76:8124-8137 (2002).
Furman et al., "Phosphorylation of 3'-azido-3'-deoxythymidine and selective interaction of the 5'-triphosphate with human immunodeficiency virus reverse transcriptase," *Proc. Natl. Acad. Sci. USA*. 83:8333-8337 (1986).
Huang et al., "Functional inactivation of the SR family of splicing factors during a vaccinia virus infection," *EMBO Reports*. 3:1088-1093 (2002).
Kanopka et al. "Regulation of Adenovirus Alternative RNA Splicing by Dephosphorylation of SR Proteins," *Nature*. 393:185-187 (1998).
Kuczynski et al., "Synthesis of New 4 and 5 Disubstituted Isothiazoles," *Polish J. of Pharmacology and Pharmacy*. 36:485-491 (1984).
Reedijk et al., "Safety, Pharmacokinetics, and Antiviral Activity of A77003, a $C_2$ Symmetry-Based Human Immunodeficiency Virus Protease Inhibitor," *Antimicrobial Agents and Chemotherapy*. 39:1559-1564 (1995).
ChemStar Product List, Order No. CHS 2726403, CAS Registry No. 494830-83-0, Apr. 24, 2003, Chemcats Accession No. 2003:2093953.
ChemStar Product List, Order No. CHS 2726421, CAS Registry No. 496012-09-0, Apr. 24, 2003, Chemcats Accession No. 2003:2093955.
ChemStar Product List, Order No. CHS 2726457, CAS Registry No. 672919-05-0, Apr. 24, 2003, Chemcats Accession No. 2004:2166987.
ChemStar Product List, Order No. CHS 2726514, CAS Registry No. 674360-18-0, Apr. 24, 2003, Chemcats Accession No. 2004:2167022.

* cited by examiner

*Primary Examiner*—Jane Zara
(74) *Attorney, Agent, or Firm*—Klarquist Sparkman, LLP

(57) ABSTRACT

The present invention provides: (1) antiviral agents that act by reducing or inhibiting the activity of SR proteins, more specifically, (i) antiviral agents that act by enhancing dephosphorylation of SR proteins, and (ii) antiviral agents that act by inhibiting proteins that phosphorylate SR proteins; (2) antiviral agents that act by inhibiting the expression of SR proteins, and (3) antiviral agents that act by activating proteins that antagonize SR proteins. The present invention also provides compounds that inhibit SRPKs, which phosphorylate SR proteins. Such compounds inhibit the activity of SR proteins and have antiviral activities. Various new viruses including SARS have emerged, and thus the present invention provides long-lasting broad-spectrum antiviral agents applicable to new viruses.

7 Claims, 12 Drawing Sheets

SRPIN-1(C18H18F3N3O)
MW349.35

PLAQUE ASSAY

| RESULTS | N.o | 340 | PFU/ml |
|---|---|---|---|
| | 340c-1 | 0 | $1.05 \times 10^7$ |
| | 340c-2 | DMSO | $1.20 \times 10^7$ |
| | 340-1 | 5uM(F/c) | $3.85 \times 10^6$ |
| | 340-2 | 10uM(F/c) | $3.60 \times 10^6$ |
| | 340-3 | 20uM(F/c) | $3.40 \times 10^6$ |
| | 340-4 | 40uM(F/c) | $1.25 \times 10^6$ |

(A)

CONTROL   #340   #349
          (40 μM) (40 μM)

15.5      1.5      7    (*10⁶ PFU/ml)

(B)

C : CONTROL,
S : SRPIN-1(#340) CONCENTRATION (μM)

METHOD FOR CONTROLLING SR PROTEIN PHOSPHORYLATION, AND ANTIVIRAL AGENTS WHOSE ACTIVE INGREDIENTS COMPRISE AGENTS THAT CONTROL SR PROTEIN ACTIVITY

CROSS REFERENCE TO RELATED APPLICATIONS

This is the U.S. National Stage of International Application No. PCT/JP2004/019393, filed Dec. 24, 2004 which in turn claims the benefit of Japan Application No. 2003-435085, filed Dec. 26, 2003. Both of these applications are incorporated herein by reference in their entirety.

TECHNICAL FIELD

The present invention relates to controlling the phosphorylation of SR proteins, which are involved in splicing reactions in the process of gene expression. The present invention also relates to methods for controlling the activity, expression, and stabilization of SR proteins that are useful for treating and preventing chronic and acute diseases caused by the infection of viruses or such, and antiviral agents whose active ingredients comprise agents that control SR protein activity. Furthermore, the present invention also relates to compounds useful for controlling SR protein activity and for antiviral treatments, and uses thereof.

BACKGROUND ART

Many of the antiviral agents reported to date as inhibiting viral replication are targeted at viral proteases or reverse transcriptases of viruses and so on.

For example, in the case of HIV virus, methods targeting the characteristics of the HIV genome are used. HIV's RNA genome is converted into DNA (provirus) by reverse transcriptase, and is then integrated into host chromosomes. Then, the transcription and translation mechanisms of the host cells produce viral proteins from the proviral DNA. These proteins are expressed as large polyprotein precursors. The precursors are cleaved into proteins by proteases, and then HIV virus is re-constituted and matured. Thus, HIV inhibitors targeted to each step in this HIV maturation process have been studied and developed; such inhibitors include (1) AZT and the like, which are targeted at reverse transcriptases characteristic of retroviruses (Non-patent Document 1) and (2) protease inhibitors, which inhibit proteases (Non-patent Document 2).

However, all of these are individually targeted antiviral agents that specifically attack the propagation process of the various viruses.

Non-patent Document 1: Proc Natl Acad Sci USA Vol. 86, No. 21, pp. 8333-7

Non-patent Document 2: Antimicrob Agents Chemother. July 1995; 39(7):1559-64

DISCLOSURE OF THE INVENTION

Problems to be Solved by the Invention

Since the natural rate of mutation is higher in viruses, and in RNA viruses in particular, the antiviral agents developed thus far, which target viral proteases or reverse transcriptases of viruses and so on, often rapidly lose their efficacy. Thus, the development of more effective antiviral agents is desired.

Specifically, in accordance with the recent emergence of various new viruses, including SARS, an objective of the present invention is to develop long-lasting broad-spectrum antiviral agents that are also applicable to new viruses.

Means to Solve the Problems

The present inventors previously studied the phosphorylation of SR proteins, which are involved in gene expression systems. In particular, the present inventors were the first in the world to clone SRPK2, an enzyme that phosphorylates SR proteins (Biochem. Biophys. Res. Commun. 242, 357-364), SPK1, a nematode SRPK homolog (Mech. Dev. 99, 51-64), hPRP4 (J. Biol. Chem. 277, 44220-44228), and CLASP, a regulatory factor for SR protein kinase Clk4 (J. Biol. Chem. 276, 32247-32256).

SR proteins are RNA-binding proteins rich in serine and arginine. SR proteins typically share one or two RNA-recognition motifs (RRM) and an RS (Arginine/Serine-rich) domain that is rich in consecutive RS sequences. The proteins play an important role in eukaryotic RNA processing, and in splicing of pre-mRNA in particular.

The following ten types of RNA-binding proteins belonging to the mammalian SR protein family have been reported: X16/SRp20, SF2/ASF/SRp30a, SC35/PR264/SRp30b, SRp30c, 9G8, HRS/SRp40, SRp46, SRp55, SRp75, and p54. Most SR proteins have been shown to be phosphorylated in cells. In particular, peptide mapping analysis has revealed that SF2/ASF, an SR protein, is phosphorylated at multiple sites within the RS domain (J. Cell. Biol. (1991) 115:587-596). Furthermore, the phosphorylation is known to potentiate the ability of SF2/ASF to selectively bind to U1snRNP (Genes & Dev. (1997) 11:334-344). The phosphorylation and dephosphorylation of RS domains is required for spliceosome formation and rearrangement. When this phosphorylation and dephosphorylation is inhibited, mRNA processing becomes abnormal. RS domains are found not only in RNA-binding proteins, as described above, but also in various functional proteins thought to function in the nucleus. These proteins have been named the "SR-related protein family" (Biochem. Cell Biol. (1999) 77: 277-291).

When studying the phosphorylation states of SR family proteins in virus-infected cells, the present inventors unexpectedly discovered that in virus-infected cells phosphorylation of SR proteins was inhibited, and these proteins were degraded via the ubiquitin-proteasome pathway. They also discovered a phenomenon whereby, conversely, SR proteins were stabilized and virus production increased upon forced expression of an SR protein, such as SRp40 or SRp75, or an SR protein kinase, such as SRPK1 or SRPK2. This suggests that SR proteins play an important role in viral replication, and that the dephosphorylation of SR proteins functions as a defense system against viral invasion of the body.

SR proteins bind to U1snRNP or U2AF, and are required for spliceosome formation; the RS domains are thought to play a major role in that protein-protein interaction. Furthermore, SR proteins influence splice site selection, promoting the selection of 3' splice sites proximal to an intron. In contrast, heteronuclear ribonucleoproteins (hnRNPs), such as hnRNP A1, A2, and B1, promote the selection of distal 3' splice sites. Thus, splice site selection may depend on the intracellular ratio of SR protein and hnRNP protein.

The present inventors thus developed and provided antiviral agents targeting SR proteins, which were found to play an important role in viral replication.

Specifically, first, the inventors attempted to inhibit SR proteins by inhibiting SR protein kinase.

Since there were no known low-molecular-weight compounds that inhibited SRPK activity, the present inventors screened for low-molecular-weight compounds targeting SRPK. As a result, they discovered that SRPIN-1 (SR protein phosphorylation inhibitor 1; also referred to as Compound No. 340) had the activity of inhibiting the kinase, SRPK; SRPIN-1 is represented by the following formula:

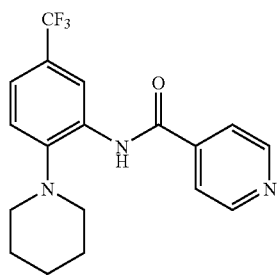

(IV)

The present inventors thus speculated that viral replication of HIV could be inhibited as a result of inhibiting SR protein phosphorylation by using SRPIN-1 to inhibit the enzymatic activity of SRPKs. Using various concentrations of SRPIN-1, they tested whether viral replication could be inhibited in infection experiments using MT-4 cells and HIV. They thus discovered that SRPIN-1 markedly inhibited HIV replication.

Further, the present inventors synthesized multiple SRPIN-1 analogs and tested their effect. Like SRPIN-1, the analogs were found to show SRPK-inhibiting activity and antiviral activity. Thus, SRPIN-1 and analogs thereof are useful as SRPK inhibitors, and can also be used as antiviral agents.

Specifically, the present invention relates to antiviral agents whose active ingredients comprise SR activity-controlling agents that control SR protein activity, methods for screening for antiviral agents, compounds with the activity of inhibiting SRPK, uses thereof, and such. More specifically, the present invention relates to each claim of the present invention:

[1] an antiviral agent comprising as an active ingredient an SR activity-controlling agent that controls an activity of an SR protein;

[2] the antiviral agent of [1], wherein the SR protein is any one of SF2/ASF/SRp30a, SC35/PR264/SRp30b, SRp30c, HRS/SRp40, SRp46, or SRp75;

[3] the antiviral agent of [1] or [2], wherein the SR activity-controlling agent is a substance or composition that enhances dephosphorylation of an SR protein;

[4] the antiviral agent of [3], which is an activator that activates Phosphatase 2A;

[5] the antiviral agent of [4], which is an expression vector for gene therapy, which carries an HIV tat gene, an adenovirus E4-ORF4 gene, or a vaccinia virus VH1 gene;

[6] the antiviral agent of [1] or [2], wherein the SR activity-controlling agent is a substance that inhibits an SRPK;

[7] the antiviral agent of [6], wherein the SRPK is an SRPK 1 or SRPK 2;

[8] the antiviral agent of [1] or [2], wherein the SR activity-controlling agent is an SRPK gene expression inhibitor;

[9] the antiviral agent of [8], wherein the SRPK gene expression inhibitor is an miRNA, siRNA, or morpholino oligo targeting an SRPK, or an expression vector for the miRNA or siRNA;

[10] the antiviral agent of [1] or [2], wherein the SR activity-controlling agent is a substance having the activity of antagonizing an SR protein;

[11] the antiviral agent of [10], wherein the substance having the activity of antagonizing an SR protein is an expression vector for hnRNPA1;

[12] the antiviral agent of any one of [1] to [11], wherein the virus is: (1) any one of the following RNA viruses: a human immunodeficiency virus (HIV), severe acute respiratory syndrome (SARS), poliovirus, human rhinovirus, adult T cell leukemia virus (HTLV-I), hepatitis A, C, D, and E viruses, vaccinia virus, Japanese encephalitis virus, dengue virus, human coronavirus, Ebola virus, influenza virus, or sindbis virus, or (2) any one of the following DNA viruses: a herpes simplex virus, human adenovirus, hepatitis B virus, cytomegalovirus, EB virus, herpesvirus, human herpesvirus, smallpox virus, polyoma virus, or human papilloma virus;

[13] a method for screening for an antiviral agent, which comprises the steps of: reacting a test compound with an SRPK, testing the ability of the SRPK to phosphorylate an SR protein, and selecting a compound that inhibits that ability;

[14] the screening method of [13], which comprises the step of testing the ability of an SRPK to phosphorylate an SR protein using, as a substrate, an SR protein or a peptide with two or more consecutive Arg-Ser (RS) or Ser-Arg (SR);

[15] a method for producing antiviral agents, which comprises the step of formulating a compound obtained by the method of [13] or [14];

[16] an aniline derivative represented by the following formula (I):

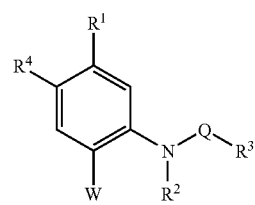

(I)

or a pharmaceutically acceptable salt or hydrate thereof;
wherein, $R^1$ represents a hydrogen atom, a $C_{1-6}$ alkyl group which may have a substituent, a $C_{2-6}$ alkenyl group which may have a substituent, a $C_{2-6}$ alkynyl group which may have a substituent, a $C_{6-10}$ aryl group which may have a substituent, a halogen atom, a nitro group, a cyano group, an azide group, a hydroxy group, a $C_{1-6}$ alkoxy group which may have a substituent, a $C_{1-6}$ alkylthio group which may have a substituent, a $C_{1-6}$ alkylsulfonyl group which may have a substituent, a carboxyl group, a formyl group, a $C_{1-6}$ alkoxycarbonyl group which may have a substituent, an acyl group, an acylamino group, or a sulfamoyl group;

$R^2$ represents a hydrogen atom, a $C_{1-6}$ alkyl group which may have a substituent, or an aryl group which may have a substituent;

$R^3$ represents a $C_{1-6}$ alkyl group which may have a substituent, a $C_{2-6}$ alkenyl group which may have a substituent, a $C_{6-10}$ aryl group which may have a substituent, a nitrogen-containing heterocycle which may have a substituent, or a condensed aromatic heterocycle which may have a substituent;

$R^4$ represents a hydrogen atom or a halogen atom;

Q represents —C(O)—, —C(S)—, —SO₂—, —C(S)NHC(O)—, —C(O)NHC(O)—, or —C(O)NHC(S)—;

W represents a hydrogen atom, a $C_{1-6}$ alkyl group which may have a substituent, a $C_{6-10}$ aryl group which may have a substituent, a halogen atom, a hydroxy group, a $C_{1-6}$ alkoxy group which may have a substituent, a $C_{1-6}$ alkylthio group which may have a substituent, a nitrogen-containing heterocycle which may have a substituent, a condensed aromatic heterocycle which may have a substituent, or a group represented by the following formula (II):

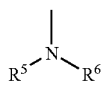

(II)

wherein, $R^5$ and $R^6$ are the same or different and each represents a hydrogen atom, a $C_{1-6}$ alkyl group which may have a substituent, a nitrogen-containing heterocycle which may have a substituent, a condensed aromatic heterocycle which may have a substituent, an acyl group, or an acylamino group;

the above $R^5$ and $R^6$ together with the adjacent nitrogen atom may form a heterocycle which may have a substituent, and the heterocycle may be a condensed aromatic heterocycle which may have a substituent;

the above $R^5$ and $R^6$ may be a cycloalkylidene amino group which may have a substituent, or an aromatic condensed cycloalkylidene group which may have a substituent;

[17] the aniline derivative of [16], or a pharmaceutically acceptable salt or hydrate thereof, wherein the above $R^1$ is a hydrogen atom, a $C_{1-6}$ alkyl group which may have a substituent, or a halogen atom;

[18] the aniline derivative of [16] or [17], or a pharmaceutically acceptable salt or hydrate thereof, wherein the above $R^2$ is a hydrogen atom or a $C_{1-6}$ alkyl group;

[19] the aniline derivative of any one of [16] to [18], or a pharmaceutically acceptable salt or hydrate thereof, wherein the above $R^3$ is a $C_{6-10}$ aryl group which may have a substituent, or a nitrogen-containing 5- to 10-membered heteroaryl group which may have a substituent;

[20] the aniline derivative of any one of [16] to [19], or a pharmaceutically acceptable salt or hydrate thereof, wherein the above $R^4$ is a hydrogen atom;

[21] the aniline derivative of any one of [16] to [20], or a pharmaceutically acceptable salt or hydrate thereof, wherein the above W represents a hydrogen atom, a halogen atom, or a group represented by the following formula (II):

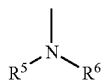

(II)

wherein, $R^5$ and $R^6$ are the same or different and each represent a $C_{1-6}$ alkyl group which may have a substituent; or the above $R^5$ and $R^6$ together with the adjacent nitrogen atom may form a heterocyclic group which may have a substituent, and the heterocyclic group may be a condensed aromatic heterocyclic group which may have a substituent;

[22] an SRPK inhibitor comprising as an active ingredient any one of the aniline derivatives of [16] to [21], or a pharmaceutically acceptable salt or hydrate thereof, and

[23] an antiviral agent comprising as an active ingredient any one of the aniline derivatives of [16] to [21], or a pharmaceutically acceptable salt or hydrate thereof.

Inventions that comprise one or more combinations of inventions set forth in claims that cite an identical claim are intended to include the inventions of those claims Hereinafter, the terms, symbols, and such used herein are defined, and the present invention will be explained in more detail.

Herein, "$C_{1-6}$ alkyl group" refers to a linear or branched alkyl group comprising one to six carbon atoms, which is a monovalent group derived by removing an arbitrary hydrogen atom from an aliphatic hydrocarbon consisting of one to six carbons. Specifically, the $C_{1-6}$ alkyl group includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group.

Herein, "$C_{2-6}$ alkenyl group" refers to a linear or branched alkenyl group comprising two to six carbons. Specifically, the $C_{2-6}$ alkenyl group includes, for example, a vinyl group, an allyl group, a 1-propenyl group, a 2-propenyl group, a 1-butenyl group, a 2-butenyl group, a 3-butenyl group, a pentenyl group, and a hexenyl group.

Herein, "$C_{2-6}$ alkynyl group" refers to a linear or branched alkynyl group comprising two to six carbons. Specifically, the $C_{2-6}$ alkynyl group includes, for example, an ethynyl group, a 1-propynyl group, a 2-propynyl group, a butynyl group, a pentynyl group, and a hexynyl group.

Herein, "$C_{1-6}$ alkoxy group" refers to an oxy group to which the above-defined "$C_{1-6}$ alkyl group" is linked. Specifically, the $C_{1-6}$ alkoxy group includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group.

Herein, "$C_{1-6}$ alkylthio group" refers to a thio group to which the above-defined "$C_{1-6}$ alkyl group" is linked. Specifically, the "$C_{1-6}$ alkylthio group" includes, for example, a methylthio group, an ethylthio group, a 1-propylthio group, a 2-propylthio group, a butylthio group, and a pentylthio group.

Herein, "$C_{1-6}$ alkoxycarbonyl group" refers to a carbonyl group to which the above-defined "$C_{1-6}$ alkoxy group" is linked. Specifically, the $C_{1-6}$ alkoxycarbonyl group includes, for example, a methoxy carbonyl group, an ethoxy carbonyl group, a 1-propyloxycarbonyl group, and a 2-propyloxycarbonyl group.

Herein, "$C_{1-6}$ alkylsulfonyl group" refers to a sulfonyl group to which the above-defined "$C_{1-6}$ alkyl group" is linked. Specifically, the $C_{1-6}$ alkylsulfonyl group includes, for example, a methylsulfonyl group, an ethylsulfonyl group, a 1-propylsulfonyl group, and a 2-propylsulfonyl group.

Herein, "halogen atom" refers to a fluorine atom, a chlorine atom, a bromine atom, and an iodine atom.

Herein, "$C_{6-10}$ aryl group" refers to an aromatic cyclic hydrocarbon group comprising six to ten carbon atoms. Specifically, the $C_{6-10}$ aryl group includes, for example, a phenyl group, a 1-naphthyl group, and a 2-naphthyl group.

Herein, "heterocycle" refers to an aromatic or non-aromatic ring that may comprise double bonds within the ring, wherein one or two of the atoms constituting the ring are heteroatoms.

Herein, "nitrogen-containing heterocycle" refers to an aromatic or non-aromatic ring that may comprise double bonds within the ring, wherein one or two of the atoms constituting the ring are nitrogen atoms.

Herein, "heteroatom" refers to a sulfur atom, an oxygen atom, or a nitrogen atom.

Herein, "nitrogen-containing 5- to 10-membered heteroaryl ring" refers to an aromatic ring in which five to ten atoms constitute the ring, wherein at least one of the atoms constituting the ring is a nitrogen atom, and one or more heteroatoms other than nitrogen atoms may further be comprised.

Specifically, the nitrogen-containing 5- to 10-membered heteroaryl ring includes, for example, a pyridine ring, a pyrrole ring, an oxazole ring, an isoxazole ring, a thiazole ring, an isothiazole ring, an indole ring, an isoindole ring, an imidazole ring, a triazole ring, a pyrazole ring, a pyridazine ring, a pyrimidine ring, a pyrazine ring, a quinoline ring, an isoquinoline ring, and a benzimidazole ring.

The "5- to 10-membered heteroaryl ring" preferably includes a pyridine ring, a pyrrole ring, and an imidazole ring, and more preferably includes a pyridine ring.

Herein, "nitrogen-containing 5- and 10-membered heteroaryl group" refers to a mono- or divalent group derived by removing one or two arbitrary hydrogen atoms from the above-defined "5- and 10-membered heteroaryl ring". Specifically, the nitrogen-containing 5- and 10-membered heteroaryl group includes, for example, a pyridyl group, a pyrrolyl group, an oxazolyl group, an isoxazolyl group, a thiazolyl group, an isothiazolyl group, an indolyl group, an isoindolyl group, an imidazolyl group, a triazolyl group, a pyrazolyl group, a pyridazinyl group, a pyrimidinyl group, a pyrazinyl group, a quinolyl group, an isoquinolyl group, and a benzimidazolyl group.

Herein, "4- to 8-membered heterocyclic ring" refers to a non-aromatic ring that meets the following definition:
1. four to eight atoms constitute the ring;
2. one or two of the atoms constituting the ring are heteroatoms;
3. one or two double bonds may be comprised in the ring;
4. one to three carbonyl groups may be comprised in the ring; and
5. the group is monocyclic.

The 4- to 8-membered heterocyclic ring is preferably a nitrogen-containing 4- to 8-membered heterocyclic ring that comprises nitrogen atoms as heteroatoms.

Specifically, the 4- to 8-membered heterocyclic ring includes, for example, an azetidine ring, a pyrrolidine ring, a piperidine ring, an azepane ring, an azocine ring, a tetrahydropyran ring, a morpholine ring, a thiomorpholine ring, a piperazine ring, a thiazolidine ring, a dioxane ring, an imidazoline ring, and a thiazoline ring. The "4- to 8-membered heterocyclic ring" preferably includes a pyrrolidine ring, a piperidine ring, a morpholine ring, and a piperazine ring.

Herein, "a 4- to 8-membered heterocyclic group" refers to a mono- or divalent group derived by removing one or two arbitrary hydrogen atoms from the above-defined "4- to 8-membered heterocyclic ring". Specifically, the 4- to 8-membered heterocyclic group includes, for example, an azetidinyl group, a pyrrolidinyl group, a piperidinyl group, an azepanyl group, an azocanyl group, a tetrahydropyranyl group, a morpholinyl group, a thoimorpholinyl group, a piperazinyl group, a thiazolidinyl group, a dioxanyl group, an imidazolyl group, and a thiazolyl group.

Herein, "condensed aromatic heterocycle" refers to a ring structure in which the heterocyclic moiety is ortho-condensed with an aromatic ring, such as a benzene ring. The heterocyclic moiety is an above-defined heterocycle.

Herein, "condensed aromatic heterocyclic group" refers to a ring structure in which the heterocyclic moiety is ortho-condensed with an aromatic ring, such as benzene ring. The heterocyclic moiety is an above-defined heterocyclic group.

The condensed aromatic heterocyclic group includes, for example, an indolinyl group, an isoindolinyl group, and a 1,2,3,4-tetrahydroquinoline.

Herein, "halogenated $C_{1-6}$ alkyl group" refers to a group in which at least one arbitrary hydrogen atom in the above-defined "$C_{1-6}$ alkyl group" is replaced with an above-defined "halogen atom". The halogenated $C_{1-6}$ alkyl group includes, for example, a trifluoromethyl group, a difluoromethyl group, and a monofluoromethyl group.

Herein, the phrase "may have substituents" means that a certain compound may have an arbitrary combination of one or more substituents at substitutable positions. Specifically, the substituents include, for example, groups selected from the following Substituent Group A:

[Substituent Group A]

a halogen atom, a hydroxyl group, a mercapto group, a nitro group, a cyano group, a formyl group, a carboxyl group, a trifluoromethyl group, a trifluoromethoxy group, an amino group, an oxo group, an imino group, a $C_{1-6}$ alkyl group, a $C_{1-6}$ alkoxy group.

Herein, "salt" is not particularly limited, so long as it is a pharmaceutical acceptable salt which is formed with a compound according to the present invention. Such salts include, for example, inorganic acid salts, organic salts, inorganic base salts, organic base salts, and acidic or basic amino acid salts.

Examples of preferable inorganic acid salts include: hydrochloride, hydrobromate, sulfate, nitrate, and phosphate. Examples of preferable organic salts include: acetate, succinate, fumarate, maleate, tartrate, citrate, lactate, stearate, benzoate, methanesulfonate, and p-toluene sulfonate.

Examples of preferable inorganic base salts include: alkali metal salts, such as sodium salts and potassium salts; alkali earth metal salts, such as calcium salts and magnesium salts; aluminium salts; and ammonium salts. Examples of preferable organic base salts include: diethylamine salts, diethanol amine salts, meglumine salts, and N,N'-dibenzylethylenediamine salts.

Examples of preferable acidic amino acid salts include: aspartate and glutamate. Examples of preferable basic amino acid salts include: arginine salts, lysine salts, and ornithine salts.

When left in air, the compounds of the present invention sometimes absorb moisture, and are sometimes attached to absorbed water or converted to hydrates. Such hydrates are also included in the present invention.

Furthermore, compounds of the present invention are sometimes converted into solvates, absorbing some other solvents. Such salts are also included in the present invention.

Herein, "gene" refers to DNAs or RNAs encoding transcriptional units in sense or antisense orientation. Transcriptional units refer to sequences that are continuously transcribed. Herein, a nucleic acid (DNA or RNA) encoding a protein is also referred to as a "gene for that protein".

Herein, the term "or" is used non-exclusively. For example, the phrase "A, B, or C" means that at least any one element of A, B, and C is comprised, and therefore the phrase also comprises things that comprise two or more of, or all three of A, B, and C, and things that comprise other elements.

Herein, the compounds shown in Tables 1 to 3 are sometimes referred by compound number. These compounds are sometimes shown as "GIF-", citing a compound number.

Effects of the Invention

The present invention revealed that SRPIN-1 (SR protein phosphorylation inhibitor 1) and analogs thereof had the activity of inhibiting SRPKs, which are kinases. SR proteins phosphorylated by SRPKs were found to exist stably in cells; however, SR protein phosphorylation is inhibited when SRPK enzyme activity is inhibited by SRPIN-1 or analogs and such thereof, leading to degradation of SR proteins via the ubiquitin-proteasome pathway. Then, the inventors inhibited SRPKs by adding SRPIN-1 or analogs thereof, and thus discovered that these compounds had the antiviral activity of inhibiting viral replication in HIV infection experiments.

The present invention is also beneficial in that it provides antiviral agents that control the activity of SR proteins, and by the same mechanism, are effective against a broad range of viruses.

[SR Proteins as Targets for Control]

Figure 1A:
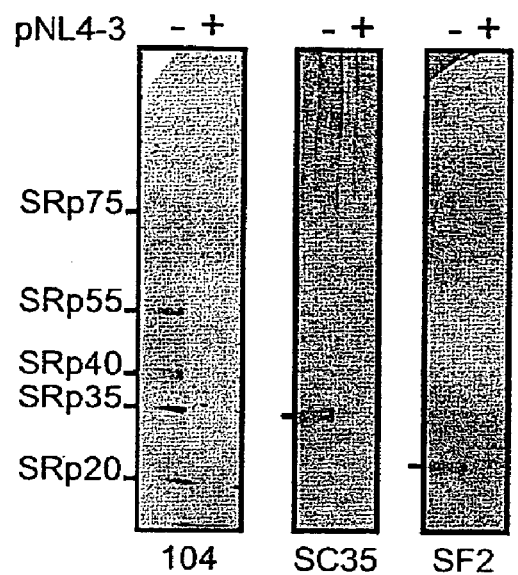
FIG. 1A: Phosphorylation of SR protein in HIV-infected cells. The pNL4-3 genome was introduced into Flp-In-293 cells. SR protein phosphorylation in these Flp-In-293 cells was evaluated by Western analysis using mouse anti-phosphorylated SR protein monoclonal antibody (Mab104), mouse anti-SC35 antibody, and mouse anti-SF2 antibody.

The SR proteins whose activity is to be reduced or inhibited according to the present invention may be arbitrary SR proteins, and specifically include X16/SRp20, SF2/ASF/SRp30a, SC35/PR264/SRp30b, SRp3c, 9G8, HRS/SRp40, SRp46, SRp55, SRp75, and p54. Preferable SR proteins are SF2/ASF/SRp30a, SC35/PR264/SRp30b, SRp30c, HRS/SRp40, SRp46, and SRp75, and particularly preferable SR proteins are SRp40 and SRp75. Hereinafter, SR protein refers to SF2/ASF/SRp30a, SC35/PR264/SRp30b, SRp30c, HRS/SRp40, SRp46, or SRp75.

The gene sequence encoding X16/SRp20 is set forth, for example, in nucleotides 1-492 of accession number L10838. The amino acid sequence of X16/SRp20 is set forth in accession numbers NP_003008 and AAA36648 (Zahler, A. et al., 1992, SR proteins: a conserved family of pre-mRNA splicing factors, Genes Dev. 6:837-847). The gene sequence encoding SF2/ASF/SRp30a is set forth, for example, in nucleotides 91-834 of accession number NM_006924. The amino acid sequence of SF2/ASF/SRp30a is set forth in accession numbers NP_008855 and Q07955 (Ge, H. et al., Cell 66, 373-382 (1991)). The gene sequence encoding SC35/PR264/SRp30b is set forth, for example, in nucleotides 156-818 of accession number M90104. The amino acid sequence of SC35/PR264/SRp30b is set forth in accession numbers AAA60306 and Q01130 (Fu, X. D. and Maniatis, T. Science 256, 535-538 (1992)). The gene sequence encoding SRp30c is set forth, for example, in nucleotides 53-715 and nucleotides 147-809 of accession numbers U30825 and NM_003769, respectively. The amino acid sequence of SRp30c is set forth in accession numbers AAA93069, Q13242, and NP_003760 (Screaton, G. R. et al., EMBO J. 14, 4336-4349 (1995)). The gene sequence encoding 9G8 is set forth, for example, in nucleotides 54-464 of accession number NM_006276. The amino acid sequence of 9G8 is set forth in accession numbers NP_006267, Q16629, and such (Lejeune, F. et al., J. Biol. Chem. 276, 7850-7858 (2001); Popielarz, M. et al., J. Biol. Chem. 270, 17830-17835 (1995); Cavaloc, Y. et al., EMBO J. 13, 2639-2649 (1994)). The gene sequence encoding HRS/SRp40 is set forth, for example, in accession number AF020307 (join(2406-2531, 2864-2925, 3049-3147, 3433-3503, 4740-4812, 5269-5382, 5472-5492)), and the amino acid sequence is set forth in accession numbers AAC39543 and Q13243, and other (Du, K. and Taub, R., Gene 204 (1-2), 243-249 (1997); Screaton, G R. et al., EMBO J. 14, 4336-4349 (1995)). The gene sequence encoding SRp46 is set forth, for example, in nucleotides 1-816 of accession number AF031166. The amino acid sequence of SRp46 is set forth in accession number AAK54351 and others (Soret, J. et al., Mol. Cell. Biol. 18, 4924-4934 (1998)). The gene sequence encoding SRp55 is set forth, for example, in nucleotides 106-1137 of accession number U30883. The amino acid sequence of SRp55 is set forth in accession numbers AAA93073 and Q13247, and others (Screaton, G R. et al., EMBO J. 14, 4336-4349 (1995); Zahler, A. M. et al., Genes Dev. 6, 837-847 (1992); Barnard, D. C. and Patton, J. G., Mol. Cell. Biol. 20, 3049-3057 (2000)). The gene sequence encoding SRp75 is set forth, for example, in nucleotides 98-1579 and nucleotides 98-1579 of accession numbers BC002781 and NM_005626, respectively. The amino acid sequence of SRp75 is set forth in accession numbers AAH02781, NP_005617 and Q08170, and others (Zahler, A. M. et al., Mol. Cell. Biol. 13, 4023-4028 (1993)). The gene sequence encoding p54 is set forth, for example, in nucleotides 84-1535 of accession number M74002. The amino acid sequence of p54 is set forth in accession numbers AAA35554 and Q05519, and others (Chaudhary, N. et al., Proc. Natl. Acad. Sci. U.S.A. 88, 8189-8193 (1991)).

[Target Viruses]

The antiviral agents of the present invention particularly preferably inhibit HIV propagation, but are not limited to human immunodeficiency virus (HIV) and also have a similar effect on other viruses, including RNA viruses, such as severe acute respiratory syndrome (SARS), polioviruses, human rhinoviruses, adult T cell leukemia viruses (HTLV-I), hepatitis A, C, D, and E viruses (excluding hepatitis B virus), vaccinia viruses, Japanese encephalitis viruses, dengue viruses, human coronaviruses, Ebola viruses, influenza viruses, and sindbis viruses. Human coronaviruses include SARS coronaviruses (also referred to as a SARS-associated coronavirus or SARS virus).

Since SR protein dephosphorylation has been reported as a host defense mechanism upon infection of herpes simplex viruses and human adenoviruses, which are DNA viruses, SRPIN-1 affects herpes simplex viruses and human adenoviruses, and also has a similar effect on hepatitis B viruses, cytomegaloviruses, EB viruses, herpesviruses, human herpes viruses, smallpox viruses, polyoma viruses, and human papilloma viruses.

Particularly preferable target viruses of the present invention include viruses of the retrovirus family (Retroviridae; including viruses of the genus *lentivirus*), togavirus family (Togaviridae; including viruses of the genus *alphavirus*), herpesvirus family (Herpesviridae; including *cytomegalovirus*), and coronavirus family (Coronaviridae; including viruses of the genus *coronavirus*).

[Antiviral Agents]

The present invention includes: (1) antiviral agents that act by reducing or inhibiting SR protein activity, more specifically, antiviral agents that act by enhancing the dephosphorylation of SR proteins, and (ii) antiviral agents that act by inhibiting proteins that phosphorylate SR proteins.

The present invention also includes: (2) antiviral agents that act by inhibiting SR protein expression, and (3) antiviral agents that act by activating the function of proteins that antagonize SR proteins.

In particular, the present invention relates to antiviral agents comprising compounds that inhibit the activity and/or expression of SRPK. The phosphorylation that contributes to the stabilization of SR protein is inhibited by inhibiting the activity and/or expression of SRPK. As a result, degradation of SR protein is promoted, and SR protein activity is reduced. Thus, SRPK (SRPK1 and/or SRPK2) is a particularly preferable inhibition target of the present invention.

[Methods for Inhibiting Viral Production]

The present invention also includes: (1) methods for inhibiting viral production by reducing or inhibiting SR protein activity, more specifically, the present invention includes (i)

methods for inhibiting virus production by enhancing the dephosphorylation of SR protein, and (ii) methods for inhibiting virus production by inhibiting proteins that phosphorylate SR protein. In particular, the present invention relates to methods for inhibiting viral production, which comprise the step of inhibiting the activity and/or expression of SRPK. When SRPK is inhibited, the phosphorylation of SR protein is inhibited, and the SR protein level is reduced, which thus reduces SR protein activity.

The present invention also includes: (2) methods for inhibiting viral production by inhibiting SR protein expression, and (3) methods for inhibiting viral production by activating the function of proteins that antagonize SR protein.

Specifically, the present invention also includes the following inventions:

[M1] Method of inhibiting propagation of a virus, which comprises the step of reducing an activity or expression level of an SR protein;

[M2] the method of [M1], in which the SR protein is SF2/ASF/SRp30a, SC35/PR264/SRp30b, SRp30c, HRS/SRp40, SRp46, or SRp75;

[M3] the method of [M1] or [M2], in which the step of reducing an activity or expression level of an SR protein is the step of inhibiting the phosphorylation of an SR protein or enhances its dephosphorylation;

[M4] the method of [M3], in which the step of inhibiting the phosphorylation of an SR protein or enhances its dephosphorylation is the step of increasing an activity of protein phosphatase 2A;

[M5] the method of [M4], in which the step of increasing an activity of protein phosphatase 2A is the step of introducing an expression vector for one or more genes selected from the group consisting of: an HIV tat gene, adenovirus E4-ORF4 gene, and vaccinia virus VH1 gene;

[46] the method of [M3], in which the step of inhibiting the phosphorylation of an SR protein or enhances its dephosphorylation is the step of inhibiting an expression or activity of a SRPK;

[M7] the method of [M6], in which the SRPK is SRPK1 or SRPK2;

[M8] the method of [M6] or [M7], in which the step of inhibiting an expression or activity of a SRPK is the step of administering an aniline derivative represented by the following formula:

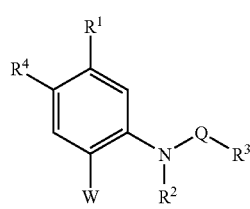

(I)

or a pharmaceutically acceptable salt or hydrate thereof;
wherein, $R^1$, $R^2$, $R^3$, $R^4$, Q, and W are defined in [16] herein above;

[M9] the method of [M8], in which the above $R^1$ is a hydrogen atom, a $C_{1-6}$ alkyl group which may have a substituent, or a halogen atom;

[M10] the method of [M8] or [M9], in which the above $R^2$ is a hydrogen atom or a $C_{1-6}$ alkyl group;

[M11] the method of any one of [M8] to [M10], in which the above $R^3$ is a $C_{6-10}$ aryl group which may have a substituent, or a nitrogen-containing 5- to 10-membered heteroaryl group which may have a substituent;

[M12] the method of any one of [M8] to [M11], in which the above $R^4$ is a hydrogen atom;

[M13] the method of any one of [M8] to [M12], in which the above W is a hydrogen atom, a halogen atom, or a group represented by the following formula (II):

(II)

wherein, $R^5$ and $R^6$ are defined above;

[M14] the method of [M8], in which the aniline derivative of [M8] is selected from the group consisting of compounds with Compound Nos: 340, 348, 613, 616, 618, 622, and 624 described herein;

[M15] the method of [M6], in which the step of inhibiting an expression or activity of a SRPK is the step of introducing a SRPK miRNA, siRNA or morpholino oligo, or introducing an miRNA or siRNA expression vector;

[M16] the method of [M1] or [M2], in which the step of reducing an activity or expression level of an SR protein is the step of administering a substance having an activity of antagonizing an SR protein;

[M17] the method of [M16], in which the substance having an activity of antagonizing an SR protein is an hnRNP A1 expression vector;

[M18] the method of any one of [M1] to [M17], in which the virus is: any one of (1) an RNA virus: a human immunodeficiency virus (HIV), severe acute respiratory syndrome (SARS), poliovirus, human rhinovirus, adult T cell leukemia virus (HTLV-I), hepatitis A, C, D, and E virus, vaccinia virus, Japanese encephalitis virus, dengue virus, human coronavirus, Ebola virus, influenza virus, and sindbis virus, and (2) a DNA virus: a herpes simplex virus, human adenovirus, hepatitis B virus, cytomegalovirus, EB virus, herpesvirus, human herpesvirus, smallpox virus, polyoma virus, and human papilloma virus.

[M19] the method of inhibiting a SRPK, which comprises the step of administering the aniline derivative of [M8], or a pharmaceutically acceptable salt or hydrate thereof;

[M20] the method of [M19], in which the SRPK is SRPK1 or SRPK2;

[M21] the method of [M19] or [M20], in which the above $R^1$ is a hydrogen atom, a $C_{1-6}$ alkyl group which may have a substituent, or a halogen atom;

[M22] the method of any one of [M19] to [M21], in which the above $R^2$ is a hydrogen atom or a $C_{1-6}$ alkyl group;

[M23] the method of any one of [M19] to [M22], in which the above $R^3$ is a $C_{6-10}$ aryl group which may have a substituent, or a nitrogen-containing 5- to 10-membered heteroaryl group which may have a substituent;

[M24] the method of any one of [M19] to [M23], in which the above $R^4$ is a hydrogen atom;

[M25] the method of any one of [M19] to [M24], in which the above W is a hydrogen atom, a halogen atom, or a group represented by the following formula (II):

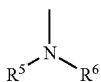

wherein, $R^5$ and $R^6$ are defined above; and

[M26] the method of [M19], in which the aniline derivative of [M8] is a compound selected from the group consisting of compounds with the Compound Nos: 340, 348, 613, 616, 618, 622, and 624 described herein, or a pharmaceutically acceptable salt or hydrate thereof.

The present invention further relates to uses of the compounds that reduce the expression and/or activity of SR protein for inhibiting viral propagation and for producing antiviral agents (reagents and/or pharmaceuticals for inhibiting viral propagation). Specifically, the present invention also relates to the following inventions:

[U1] Use of a compound that reduces an activity or expression level of an SR protein for inhibiting propagation of a virus or for producing an antiviral agent;

[U2] the use of [U1], in which the SR protein is SF2/ASF/SRp30a, SC35/PR264/SRp30b, SRp30c, HRS/SRp40, SRp46, or SRp75;

[U3] the use of [U1] or [U2], in which the compound that reduces an activity or expression level of an SR protein is a compound that inhibits the phosphorylation of an SR protein or enhances its dephosphorylation;

[U4] the use of [U3], in which the compound that inhibits the phosphorylation of an SR protein or enhances its dephosphorylation is a compound that increases an activity of protein phosphatase 2A;

[U5] the use of [U4], in which the compound that increases an activity of protein phosphatase 2A is an expression vector for one or more genes selected from the group consisting of: an HIV tat gene, adenovirus E4-ORF4 gene, and vaccinia virus VH1 gene;

[U6] the use of [U3], in which the compound that inhibits the phosphorylation of an SR protein or enhances its dephosphorylation is a compound that inhibits an expression or activity of a SRPK;

[U7] the use of [U6], in which the SRPK is SRPK1 or SRPK2;

[U8] the use of [U6], in which the compound that inhibits an expression or activity of a SRPK is an aniline derivative represented by the following formula:

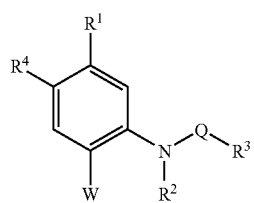

(I)

or a pharmaceutically acceptable salt or hydrate thereof; wherein, $R^1$, $R^2$, $R^3$, $R^4$, Q, and W are defined in [16] herein above;

[U9] the use of [U8], in which the above $R^1$ is a hydrogen atom, a $C_{1-6}$ alkyl group which may have a substituent, or a halogen atom;

[U10] the use of [U8] or [U9], in which the above $R^2$ is a hydrogen atom or a $C_{1-4}$ alkyl group;

[U11] the use of any one of [U8] to [U10], in which the above $R^3$ is a $C_{6-10}$ aryl group have a substituent, or a nitrogen-containing 5- to 10-membered heteroaryl group which may have a substituent;

[U12] the use of any one of [U8] to [U11], in which the above $R^4$ is a hydrogen atom;

[U13] the use of any one of [U8] to [U12], in which the above W is a hydrogen atom, a halogen atom, or a group represented by the following formula (II):

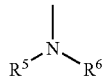

(II)

wherein, $R^5$ and $R^6$ are defined above;

[U14] the use of [U8], in which the aniline derivative of [U8] is selected from the group consisting of compounds with Compound Nos: 340, 348, 613, 616, 618, 622, and 624 described herein;

[U15] the use of [U6], in which the compound that inhibits an expression or activity of a SRPK is a SRPK miRNA, siRNA or morpholino oligo, or is an miRNA or siRNA expression vector;

[U16] the use of [U1] or [U2], in which the compound that reduces an activity or expression level of an SR protein is a substance having an activity of antagonizing an SR protein;

[U17] the use of [U16], in which the substance having an activity of antagonizing an SR protein is an hnRNP A1 expression vector;

[U18] the use of any one of [U1] to [U17], in which the virus is: any one of (1) an RNA virus: a human immunodeficiency virus (HIV), severe acute respiratory syndrome (SARS), poliovirus, human rhinovirus, adult T cell leukemia virus (HTLV-I), hepatitis A, C, D, and E virus, vaccinia virus, Japanese encephalitis virus, dengue virus, human coronavirus, Ebola virus, influenza virus, and sindbis virus, and (2) a DNA virus: a herpes simplex virus, human adenovirus, hepatitis B virus, cytomegalovirus, EB virus, herpesvirus, human herpesvirus, smallpox virus, polyoma virus, and human papilloma virus.

[U19] the use of the aniline derivative of [U8], or a pharmaceutically acceptable salt or hydrate thereof for inhibiting a SRPK or for producing a SRPK inhibitor;

[U20] the use of [U19], in which the SRPK is SRPK1 or SRPK2;

[U21] the use of [U19] or [U20], in which the above $R^1$ is a hydrogen atom, a $C_{1-6}$ alkyl group which may have a substituent, or a halogen atom;

[U22] the use of any one of [U19] to [U21], in which the above $R^2$ is a hydrogen atom or a $C_{1-6}$ alkyl group;

[U23] the use of any one of [U19] to [U22], in which the above $R^3$ is a $C_{6-10}$ aryl group which may have a substituent, or a nitrogen-containing 5- to 10-membered heteroaryl group which may have a substituent;

[U24] the use of any one of [U19] to [U23], in which the above $R^4$ is a hydrogen atom;

[U25] the use of any one of [U19] to [U24], in which the above W is a hydrogen atom, a halogen atom, or a group represented by the following formula (II):

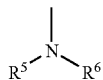

(II)

wherein, $R^5$ and $R^6$ are defined above; and

[U26] the use of [U19], in which the aniline derivative of [U8] is a compound selected from the group consisting of compounds with the Compound Nos: 340, 348, 613, 616, 618, 622, and 624 described herein, or a pharmaceutically acceptable salt or hydrate thereof.

[Therapeutic Methods]

The present invention includes: (1) methods for treating or preventing viral diseases by reducing or inhibiting SR protein activity, more specifically, (i) methods for treating or preventing viral diseases by dephosphorylating SR protein, and (ii) methods for treating viral diseases by inhibiting proteins that phosphorylate SR protein. In particular, the present invention relates to methods for treating or preventing viral diseases, which comprise the step of inhibiting the activity and/or expression of SRPK. SRPK inhibition results in inhibition of SR protein phosphorylation, which reduces the SR protein level and thus inhibits viral propagation.

The present invention also includes: (2) methods for treating or preventing viral diseases by inhibiting the expression of SR protein, and (3) methods for treating or preventing viral diseases by activating the function of proteins that antagonize SR protein.

III.

The present invention also includes methods for screening for antiviral agents and uses of SRPK inhibitors.

[Methods for Screening for Antiviral Agents]

The present invention also includes: (1) methods for screening SRPK inhibitors using SR proteins or peptides with two or more consecutive units of RS or SR as SRPK substrates

[SRPK Inhibitors and Use Thereof]

The present invention also includes: (1) SRPK inhibitors comprising SRPIN-1 or an analog thereof as an active ingredient, (2) viral propagation inhibitors comprising SRPIN-1 or an analog thereof as an active ingredient, and (3) antiviral therapeutic agents comprising SRPIN-1 or an analog thereof as an active ingredient.

IV. Specific Disclosures of the Present Invention (1) Antiviral Agents that Reduce or Inhibit the Activity of SR Proteins (i) Antiviral Agents that Act by Dephosphorylating SR Proteins The antiviral agents that act by dephosphorylating SR proteins include activators that activate Phosphatase 2A (Mumby, M. C. and Walter, G (1993) Physiol. Rev. 73, 673-680; Lechward, K., Awotunde, O. S., Swiatek, W. and Muszynska, G (2001) Acta Biochim. Pol. 48, 921-933; Cohen, P. (1989) The structure and regulation of protein phosphatases. Annu. Rev. Biochem. 58, 453-508; Janssens, V. and Goris, J. (2001) Biochem. J. 353, 417-39). Specifically, such antiviral agents include polypeptides encoded by HIV tat gene (for example, accession number AAK08486), polypeptides encoded by adenovirus E4-ORF4 (for example, accession number AAB37507), or polypeptides encoded by vaccinia virus VH1 (for example, accession number AAV38329). Furthermore, such antiviral agents also include expression vectors for gene therapy, which carry a HIV tat gene, adenovirus E4-ORF4 gene, or vaccinia virus VH1 gene. A tat gene is available, for example, as CDS (nucleotides 5830-6044 plus nucleotides 8369-8411)under accession number AF324493; E4-ORF4 is available, for example, as CDS (nucleotides 1634-1993) under accession number S82508; vaccinia virus VH1 is available, for example, as CDS (nucleotides 1-555) under accession number BT019522.

(ii) SR Protein Kinase Inhibitors (ii-1)

There are various kinases already known as enzymes that phosphorylate SR proteins, but these enzymes are thought to phosphorylate RS domains at different sites. The present inventors discovered that SRPKs are the only RS kinases that achieve the specific phosphorylation which contributes to SR protein stabilization. Thus, to prevent the stabilization of SR proteins through phosphorylation, the target SR protein kinases particularly include SRPKs. The SRPKs include both SRPK1 (Nature (1994) Vol. 369, pp. 678-682) and SRPK2 (Biochem. Biophys. Res. Commun. (1998) Vol. 242: pp. 357-364; Wang, H. Y. et al., J. Cell. Biol. 1998, 140:737-750). The nucleotide sequence of SRPK1 gene is set forth, for example, in nucleotides 124-2088, nucleotides 109-2073, nucleotides 10-2487, and nucleotides 43-1986 of accession numbers NM_003137, U09564, AJ318054, and NM_016795, respectively. The amino acid sequence is set forth, for example, in accession numbers NP_003128, AAA20530, CAC39299, CAA11833, and NP_058075. Meanwhile, the nucleotide sequence of SRPK2 gene is set forth, for example, in nucleotides 188-2245 and nucleotides 208-2253 of accession numbers U88666 and NM_009274,respectively. The amino acid sequence is set forth, for example, in AAC05299 and NP_033300 (Nikolakaki, E. et al., J. Biol. Chem. 276, 40175-40182 (2001); Papoutsopoulou, S., et al., Nucleic Acids Res. 27, 2972-2980 (1999); Wang, H. Y. et al., Genomics 57, 310-315 (1999); Gui, J. F. et al., Nature 369, 678-682 (1994); Wang, H. Y. et al., J. Cell Biol. 140, 737-750 (1998); Papoutsopoulou, S. et al., Nucleic Acids Res. 27, 2972-2980 (1999); Kuroyanagi, N. et al., Biochem. Biophys. Res. Commun. 242, 357-364 (1998); Bedford, M. T. et al., EMBO J. 16, 2376-2383 (1997)). SRPK1s also include the species referred to as "SRPK1a".

Substances having the function of inhibiting kinases (SRPKs), which are used in the methods of the present invention, include compounds (including SRPIN-1 and analogs thereof) represented by the following formula:

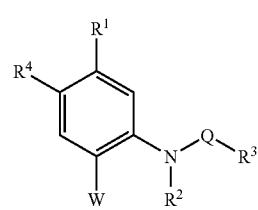

(I)

and pharmaceutically acceptable salts and hydrates thereof;
wherein, $R^1$ represents a hydrogen atom, a $C_{1-6}$ alkyl group which may have substituents, a $C_{2-6}$ alkenyl group which may have substituents, a $C_{2-6}$ alkynyl group which may have substituents, a $C_{6-10}$ aryl group which may have substituents, a halogen atom, a nitro group, a cyano group, an azide group, a hydroxy group, a $C_{1-6}$ alkoxy group which may have substituents, a $C_{1-6}$ alkylthio group which may have substituents, a $C_{1-6}$ alkylsulfonyl group which may have substituents, a carboxyl group, a formyl group, a $C_{1-6}$ alkoxycarbonyl group which may have substituents, an acyl group, an acylamino group, or a sulfamoyl group;

$R^2$ represents a hydrogen atom, a $C_{1-6}$ alkyl group which may have substituents or an aryl group which may have substituents;

$R^3$ represents a $C_{1-6}$ alkyl group which may have substituents, a $C_{2-6}$ alkenyl group which may have substituents, a $C_{6-10}$ aryl group which may have substituents, a nitrogen-containing heterocycle which may have substituents, or a condensed aromatic heterocycle which may have substituents;

$R^4$ represents a hydrogen atom or a halogen atom;

Q represents —C(O)—, —C(S)—, —SO$_2$—, —C(S)NHC(O)—, —C(O)NHC(O)—, or —C(O)NHC(S)—;

W represents a hydrogen atom, a $C_{1-6}$ alkyl group which may have substituents, a $C_{6-10}$ aryl group which may have substituents, a halogen atom, a hydroxy group, a $C_{1-6}$ alkoxy group which may have substituents, a $C_{1-6}$ alkylthio group which may have substituents, a nitrogen-containing heterocycle which may have substituents, a condensed aromatic heterocycle which may have substituents, or a group represented by the following formula (II);

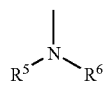

(II)

wherein, $R^5$ and $R^6$ are the same or different and each represent a hydrogen atom, a $C_{1-6}$ alkyl group which may have substituents, a nitrogen-containing heterocycle which may have substituents, a condensed aromatic heterocycle which may have substituents, an acyl group, or an acylamino group; or the above $R^5$ and $R^6$, together with the adjacent nitrogen atom, may form a heterocycle which may have substituents, and the heterocycle may be a condensed aromatic heterocycle which may have substituents;

the above $R^5$ and $R^6$ may be a cycloalkylidene amino group which may have substituents or an aromatic condensed cycloalkylidene group which may have substituents.

Examples of the compounds described above include the compounds represented by the following formula:

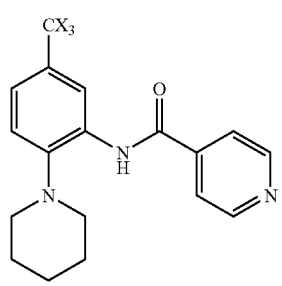

(III)

X includes F, Cl, Br, I, and At.

Specifically, such compounds includes SRPIN-1, represented by the following formula:

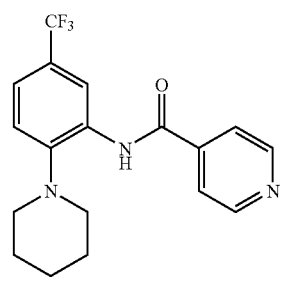

(IV)

The SRPIN-1 of the present invention is available from Maybridge (Trevillett, Tintagel, Cornwall PL34 OHW, England) and Ambinter (46 quai Louis Bleriot, Paris, F-75016 France); however, the following outlines its chemical synthesis:

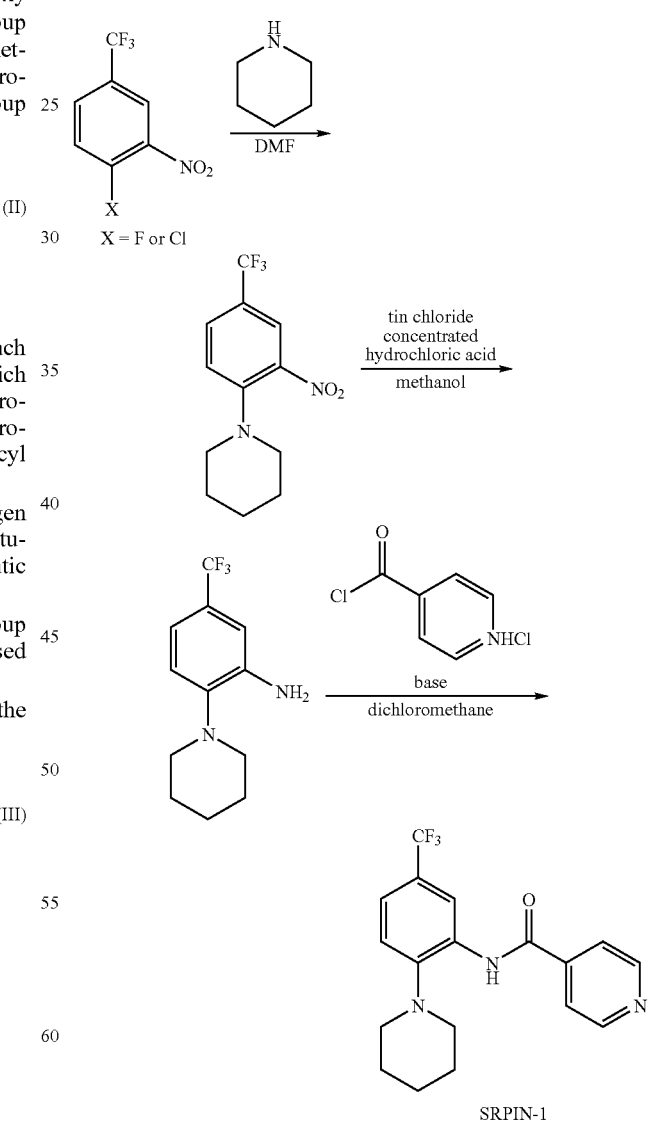

SRPIN-1

(ii-2) Antiviral Agents Using RNAi Targeting SRPK1 Gene and SRPK2 Gene

Inside cells, siRNAs, morpholino oligos, or miRNAs can be used to reduce the expression level of genes encoding SRPK1 and SRPK2.

Known methods can be used to design siRNAs. The RNAs may be designed, for example, by the following methods:

(ii-2-1)

The sequences that can be used as siRNA targets avoid the 5' and 3' UTRs (untranslated region) and sequences adjacent to the start codon; are 50 nucleotides or more downstream of the start codon; are within the ORF and start from AA or NA; comprise 19 to 21 nucleotides (most typically 19 nucleotides) whose CG content is about 50%; and minimal sequence biases and repeats at the 5' and 3' ends.

When the target sequence starts with AA, siRNAs may be prepared to comprise a dinucleotide overhang of dTdT or UU. Alternatively, when the target sequence starts with NA, siRNAs may be prepared to comprise dTdN, dTdT, or UU.

To prevent cross-reactions with sequences other than the target sequence from affecting expression of proteins other than the target protein, a BLAST search or the like will confirm whether the selected sequence has homology with other RNA sequences.

The present invention also includes embodiments that use siRNA expression vectors, constructed to allow intracellular expression of the designed siRNAs.

The morpholino oligos are compounds in which multiple nucleotide-comprising morpholino subunits are linked in a chain comprising structures that link the morpholine ring and non-ionic phosphorodiamidate subunits (U.S. Pat. Nos. 5,142,047; 5,185,444). Since morpholino antisense oligos are highly stable in cells and have high affinity for mRNAs, they can thus be preferably used to inhibit the expression of target genes (Summerton J E., Ann NY Acad Sci 2003; 1002: 189). Methods for designing effective morpholino oligos are already known (see Summerton, 1989, In: Discoveries in Antisense Nucleic Acids; Ed.: C. Brakel; Pub.: The Portfolio Publishing Co., Woodlands, Tex.; pages 71-80; Summerton & Weller, 1997, Antisense Nuc. Acid Drug Dev. 7, 187; and the Gene Tools website). Morpholino oligos are available from Gene Tools (Gene Tools, LLC, Philomath, Oreg.).

(2) The Antiviral Agents that Act by Inhibiting the Expression of the Genes Encoding SR Proteins Include, for Example, siRNAs, Morpholino Oligos, and miRNAs.

(2-1) siRNAs siRNAs can be designed using the methods described above in (ii-2).

(3) Antiviral Agents Comprising Proteins that Antagonize SR Proteins or that Act by Activating These Proteins (3-1)

The phrase "antagonize SR protein" means promoting the selection of a 3' splice site distal to an intron in splicing, for example. Specifically, the activity of SR proteins can be canceled using a splicing regulatory factor that antagonizes SR proteins, which promote the selection of 3' splice sites proximal to an intron. Specifically, such proteins that antagonize SR proteins include heteronuclear ribonucleoproteins (hnRNPs), such as hnRNP A1, A2, and B1, but hnRNP A1 is preferable. More preferable are antiviral agents that are gene therapy expression vectors carrying an hnRNP A1-encoding gene. The gene sequence encoding hnRNP A1 is set forth, for example, in nucleotides 105-1064 and nucleotides 105-1220 of accession numbers NM_002136 and NM_031157, respectively. The amino acid sequence of hnRNPA1 is set forth in accessions number NP_002127 and NP_112420, and others (Expert-Bezan, Sureau, A. et al., J. Biol. Chem. 279, 38249-38259 (2004); Zahler, A. M. et al., J. Biol. Chem. 279, 10077-10084 (2004); Marchand, V. et al., J. Mol. Biol. 323, 629-652 (2002); Buvoli, M. et al., EMBO J. 9, 1229-1235 (1990); Biamonti, G. et al., J. Mol. Biol. 207, 491-503 (1989); Buvoli, M. et al., Nucleic Acids Res. 16, 3751-3770 (1988); Michael, W. M. et al., Cell 83, 415-422(1995)). The gene sequence encoding hnRNP A2/B1 is set forth, for example, in nucleotides 170-1192 and nucleotides 170-1228 of accession numbers NM_002137 and NM_031243, respectively. The amino acid sequence of hnRNP A2/B1 is set forth in accession numbers NP_002128 and NP_112533, and others (Kozu, T., et al., Genomics 25, 365-371 (1995); Biamonti, G et al., Nucleic Acids Res. 22, 1996-2002 (1994); Burd, C. G. et al., Proc. Natl. Acad. Sci. U.S.A. 86, 9788-9792 (1989); Kumar, A. et al., J. Biol. Chem. 261, 11266-11273 (1986)).

(4) Methods for Screening for Antiviral Agents, Which Comprise Screening for Substances that Inhibit SRPKs The methods for screening for antiviral agents of the present invention are, for example, methods comprising the selection of SRPK inhibitors, which comprise the steps of reacting test compounds with SRPKs, and testing the ability of the SRPKs to phosphorylate SR proteins. Compounds that impair this ability (SRPK inhibitors) are useful as antiviral agents. In particular, the present invention also includes methods for screening for antiviral agents, which comprise screening various compounds that target SRPK1 or SRPK2 for SRPK inhibitors, using SR proteins or peptides with two or more consecutive units of RS or SR as SRPK substrates. Compounds that inhibit the SR protein-phosphorylating activity of SRPKs can be selected efficiently by using peptides with two or more consecutive units of Arg-Ser (RS) or Ser-Arg (SR) as SRPK substrates, and selecting compounds that impair SRPK's ability to phosphorylate the substrates (SRPK inhibitors).

More specifically, the screenings of the present invention comprise the steps of:

(a) contacting an SRPK with a substrate in the presence of a test compound;
(b) detecting the phosphorylation of the substrate; and
(c) selecting compounds that impair phosphorylation compared to when the test compound is absent or present in small amounts.

As described above, the substrates include SR proteins, partial polypeptides thereof which comprise RS domains, and polypeptides with two or more consecutive units of RS or SR (see the Examples). The SRPKs may be wild type SRPK1 or SRPK2. Alternatively, the SRPKs may be fusion proteins comprising tag peptides or other modified proteins, as long as they retain phosphorylation activity. Herein, SRPKs comprising mutations or such are also referred to as "SRPK", as long as they retain the activity of phosphorylating SR proteins.

More specifically, herein, SRPK1 includes:

(a) a protein comprising an amino acid sequence of accession numbers NP_003128, AAA20530, CAC39299, CAA11833, or NP_058075;
(b) a protein with phosphorylation activity which comprises an amino acid sequence that exhibits 80% or higher sequence identity, preferably 85% or higher sequence identity, more preferably 90% or higher sequence identity, still more preferably 95% or higher sequence identity to this amino acid sequence;
(c) a protein with phosphorylation activity which is encoded by a nucleic acid which hybridizes under stringent conditions to a complementary strand of a nucleic acid comprising the whole or a portion of nucleotides 124-2088 of accession number NM_003137, nucleotides 109-2073 of accession number U09564, nucleotides 10-2487 of accession number AJ318054, or nucleotides 43-1986 of accession number NM_016795. Herein, SRPK2 includes:

(a) a protein comprising an amino acid sequence of accession numbers AAC05299 or NP_033300;

(b) a protein with phosphorylation activity comprising an amino acid sequence that exhibits 80% or higher sequence identity, preferably 85% or higher sequence identity, more preferably 90% or higher sequence identity, still more preferably 95% or higher sequence identity to this amino acid sequence;

(c) a protein with phosphorylation activity which is encoded by a nucleic acid which hybridizes under stringent conditions to a complementary strand of a nucleic acid comprising the whole or a portion of nucleotides 188-2245 of accession number U88666, or nucleotides 208-2253 of accession number NM_009274. The "portion" means, for example, 20 or more consecutive nucleotides, preferably 25 or more nucleotides, more preferably 30 or more nucleotides, 40 or more nucleotides, 45 or more nucleotides, 50 or more nucleotides.

Amino acid sequence identity can be determined, for example, using the BLASTP program (Altschul, S. F. et al., 1990, J. Mol. Biol. 215: 403-410). For example, homology searches are carried out at the BLAST webpage of NCBI (National Center for Biotechnology Information) using default parameters with all filters, including Low complexity, switched off (Altschul, S. F. et al. (1993) Nature Genet. 3:266-272; Madden, T. L. et al. (1996) Meth. Enzymol. 266: 131-141; Altschul, S. F. et al. (1997) Nucleic Acids Res. 25:3389-3402; Zhang, J. & Madden, T. L. (1997) Genome Res. 7:649-656). Parameters may be set, for example, as follows: gap open cost=11, gap extend cost=1, wordsize=2, Dropoff (X) for blast extensions in bits=7, X dropoff value for gapped alignment (in bits)=15, final X dropoff value for gapped alignment (in bits)=25. BLOSUM62 is used as a score matrix. Sequence identity can be determined, for example, by aligning two sequences using the blast2 sequences program, which compares two sequences (Tatiana A et al. (1999) FEMS Microbiol Lett. 174:247-250). Gaps are treated in the same way as mismatches. An identity score is calculated for the entire amino acid sequence of the wild type protein, which is set forth in the above accession numbers (for example, the entire sequence of SEQ ID NO: 2 or 4). Identity scores may be calculated disregarding gaps outside the amino acid sequence of the wild type protein in the alignment. For hybridization, a probe is prepared from either a nucleic acid comprising the coding sequence of the wild type protein (for example, SEQ ID NO: 1 or 3) or a nucleic acid targeted in the hybridization, and whether or not the probe will hybridize to other nucleic acids can be identified by detection. Stringent hybridization conditions include, for example, conditions where hybridization is carried out using a solution containing 5×SSC (1×SSC comprises 150 mM NaCl and 15 mM sodium citrate), 7% (W/V) SDS, 10 µg/ml denatured salmon sperm DNA, and 5× Denhardt's solution (1× Denhardt's solution contains 0.2% polyvinylpyrrolidone, 0.2% bovine serum albumin, and 0.2% Ficoll) at 48° C., preferably at 50° C., and more preferably at 52° C., and where post-hybridization washing is carried out for two hours at the same temperature as in the hybridization, more preferably at 60° C., still more preferably at 65° C., and even more preferably at 68° C. using 2×SSC, preferably 1×SSC, more preferably 0.5×SSC, and still more preferably 0.1×SSC, with shaking.

The phosphorylation activity of SRPKs can be detected, for example, by conducting a reaction between an SRPK and a substrate using labeled ATP, and quantifying the labeled substrate. Specifically, the methods described in Example 4B can be followed.

Compounds exhibiting marked antiviral activity may be further selected from the yielded compounds by detecting antiviral activity through the additional steps of:

(d) detecting viral propagation or the expression of a viral gene in the presence of a selected test compound; and (e) selecting a compound that reduces viral propagation or viral gene expression compared to when the compound is absent or present in small amounts.

As described in the Examples, viral propagation or viral gene expression can be evaluated, for example, by detecting the production of viral proteins in cells introduced with the viral genome.

The present invention also relates to SRPK inhibitors and antiviral agents that comprise compounds selected by the above-described screening methods of the present invention. The present invention also relates to uses of the compounds obtained by the above-described screening methods of the present invention for producing SRPK inhibitors and/or antiviral agents, and uses of the same in SRPK inhibition and/or antiviral treatments. For example, compounds selected from the group consisting of the compounds of CAS Registry Nos. 218156-96-8, 674360-18-0, 494830-83-0, 672919-05-0, 54231-51-5, 10338-55-3, 1692-79-1, 1496-40-81, 496012-09-0, 445406-05-3, 445412-62-4, and 388071-30-5 are useful as SRPK inhibitors and/or antiviral agents.

The present invention also includes uses of the above antiviral agents as viral propagation inhibitors or antiviral therapeutic agents. For example, when SRPIN-1 is used as an antiviral agent, in addition to SRPIN-1, known pharmaceutical adjuvants, for example, AZT and protease inhibitors, may be added.

The viral propagation inhibitors or antiviral therapeutic agents of the present invention may be administered, for example, orally, percutaneously, submucosally, subcutaneously, intramuscularly, intravascularly, intracerebrally, or intraperitoneally, intermittently or continuously so that their concentration in the body falls within the range of 100 nM to 1 mM.

The SRPIN-1 analog compounds of the present invention are described in more detail below. The present invention relates to compounds with the structure indicated below, and to uses thereof.

Compounds of the present invention are aniline derivatives represented by the following formula (I):

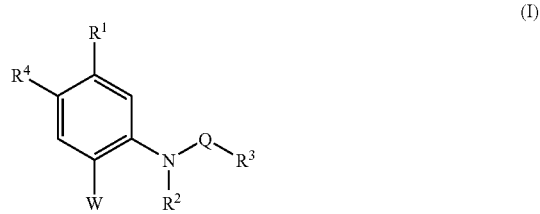

(I)

or pharmaceutically acceptable salts or hydrates thereof;
wherein, $R^1$ represents a hydrogen atom, a $C_{1-6}$ alkyl group which may have substituents, a $C_{2-6}$ alkenyl group which may have substituents, a $C_{2-6}$ alkynyl group which may have substituents, a $C_{6-10}$ aryl group which may have substituents, a halogen atom, a nitro group, a cyano group, an azide group, a hydroxy group, a $C_{1-6}$ alkoxy group which may have substituents, a $C_{1-6}$ alkylthio group which may have substituents, a $C_{1-6}$ alkylsulfonyl group which may have substituents, a carboxyl group, a formyl group, a $C_{1-6}$ alkoxycarbonyl group which may have substituents, an acyl group, an acylamino group, or a sulfamoyl group;

$R^2$ represents a hydrogen atom, a $C_{1-6}$ alkyl group which may have substituents, or an aryl group which may have substituents;

$R^3$ represents a $C_{1-6}$ alkyl group which may have substituents, a $C_{2-6}$ alkenyl group which may have substituents, a $C_{6-10}$ aryl group which may have substituents, a nitrogen-containing heterocycle which may have substituents, or a condensed aromatic heterocycle which may have substituents;

$R^4$ represents a hydrogen atom or a halogen atom;

Q represents —C(O)—, —C(S)—, —SO$_2$—, —C(S)NHC(O)—, —C(O)NHC(O)—, or —C(O)NHC(S)—;

W represents a hydrogen atom, a $C_{1-6}$ alkyl group which may have substituents, a $C_{6-10}$ aryl group which may have substituents, a halogen atom, a hydroxy group, a $C_{1-6}$ alkoxy group which may have substituents, a $C_{1-6}$ alkylthio group which may have substituents, a nitrogen-containing heterocycle which may have substituents, a condensed aromatic heterocycle which may have substituents, or a group represented by the following formula (II):

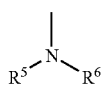

(II)

wherein, $R^5$ and $R^6$ are the same or different and each represent a hydrogen atom, a $C_{1-6}$ alkyl group which may have substituents, a nitrogen-containing heterocycle which may have substituents, a condensed aromatic heterocycle which may have substituents, an acyl group, or an acylamino group; or the above $R^5$ and $R^6$, together with the adjacent nitrogen atom, may form a heterocycle which may have substituents, and the heterocycle may be a condensed aromatic heterocyclic group which may have substituents;

the above $R^5$ and $R^6$ may be a cycloalkylidene amino group which may have substituents, or an aromatic condensed cycloalkylidene group which may have substituents.

Among such compounds represented by formula (I), preferable compounds include, for example, the following compounds:

(1) compounds in which the above $R^1$ is a hydrogen atom, a $C_{1-6}$ alkyl group which may have substituents, or a halogen atom;

(2) compounds in which the above $R^1$ is a hydrogen atom, a $C_{1-6}$ alkyl group, a halogenated $C_{1-6}$ alkyl group, or a halogen atom;

(3) compounds in which the above $R^1$ is a hydrogen atom, a methyl group, a trifluoromethyl group, a chlorine atom, or a fluorine atom;

(4) compounds in which the above $R^1$ is a hydrogen atom or a trifluoromethyl group;

(5) compounds in which the above $R^2$ is a hydrogen atom or a $C_{1-6}$ alkyl group;

(6) compounds in which the above $R^2$ is a hydrogen atom or a methyl group;

(7) compounds in which the above $R^2$ is a hydrogen atom;

(8) compounds in which the above $R^3$ is a $C_{6-10}$ aryl group which may have substituents or a nitrogen-containing 5- to 10-membered heteroaryl ring which may have substituents;

(9) compounds in which the above $R^3$ is a phenyl group; $C_{6-10}$ aryl group which has as a substituent a $C_{1-6}$ alkyl group, a $C_{1-6}$ alkoxy group, or a nitro group; or a nitrogen-containing 5- to 10-membered heteroaryl group;

(10) compounds in which the above $R^3$ is a phenyl group; a phenyl group which has as a substituent a $C_{1-6}$ alkyl group, a $C_{1-6}$ alkoxy group, or a nitro group; or a pyridyl group;

(11) compounds in which the above $R^3$ is a phenyl group, a tolyl group, a methoxyphenyl group, a nitrophenyl group, or a pyridyl group;

(12) compounds in which the above $R^3$ is a tolyl group or a pyridyl group;

(13) compounds in which the above $R^3$ is a 4-pyridyl group;

(14) compounds in which the above $R^4$ is a hydrogen atom;

(15) compounds in which the above Q is —C(O)— or —C(O)NHC(S)—, where C(O) means that an oxygen atom is linked with a carbon atom via a double bond, and C(S) means that a sulfur atom is linked with a carbon atom via a double bond;

(16) compounds in which the above Q is —C(O)—;

(17) compounds in which the above W is a hydrogen atom, a halogen atom, or a group represented by the following formula (II):

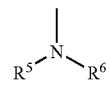

(II)

wherein, $R^5$ and $R^6$ are the same or different and each represent a C1-6 alkyl group which may have substituents; or the above $R^5$ and $R^6$, together with the adjacent nitrogen atom, may form a heterocyclic group which may have substituents; and the heterocyclic group may be a condensed aromatic heterocyclic group which may have substituents;

(18) compounds in which the above W is a 4- to 8-membered heterocyclic group having one nitrogen atom, which may have a $C_{1-6}$ alkyl group as a substituent, a 4- to 8-membered heterocyclic group comprising one nitrogen atom and one oxygen atom, which may have a $C_{1-6}$ alkyl group as a substituent, or a 4- to 8-membered heterocyclic group which is condensed with a phenyl group and comprises one nitrogen atom;

(19) compounds in which the above W is a 4- to 8-membered heterocyclic group comprising one nitrogen atom, which may have a $C_{1-6}$ alkyl group as a substituent;

(20) compounds in which the above W is a piperidinyl group or a perhydroazepine group, which may have a $C_{1-6}$ alkyl group as a substituent; and

(21) compounds in which the above W is a hydrogen atom, a halogen atom, a diethylamino group, a pyrrolidinyl group, a piperidinyl group, a 2-methylpiperidinyl group, a perhydroazepine group, an indolinyl group, an isoindolinyl group, or a 1,2,3,4-tetrahydroquinolyl group.

In the compounds described above, $R^1$ is preferred in the order of (1) to (4), with (4) most preferred. $R^2$ is more preferred in the order of (5) to (7), with (7) most preferred. $R^3$ is more preferred in the order of (8) to (13), with (13) most preferred. Q is more preferred in the order of (15) to (16), with

(16) most preferred. W is more preferred in the order of (17) to (20), with (20) most preferred. W defined in (21) is also preferred.

More preferable compounds are represented by the above formula (I), and comprise arbitrary combinations of preferable substituent types, each of which is selected from the group consisting of (1) to (4), the group consisting of (5) to (7), the group consisting of (8) to (13), the group consisting of (14), the group consisting of (15) to (16), or the group consisting of (17) to (21).

Specific compounds represented by formula (1) are shown herein below, but the present invention is not to be construed as being limited thereto.

TABLE 1

| Compound No. | Structural Formula |
| --- | --- |
| 340 | |
| 341 | |
| 342 | |
| 343 | |

TABLE 1-continued

| Compound No. | Structural Formula |
| --- | --- |
| 344 | |
| 345 | |
| 346 | |
| 347 | |
| 348 | |

TABLE 1-continued

| Compound No. | Structural Formula |
|---|---|
| 349 | (structure) |

TABLE 2

| Compound No. | Structural Formula |
|---|---|
| 608 | (structure) |
| 609 | (structure) |
| 610 | (structure) |
| 611 | (structure) |

TABLE 2-continued

| Compound No. | Structural Formula |
|---|---|
| 612 | (structure) |
| 613 | (structure) |
| 614 | (structure) |
| 615 | (structure) |
| 616 | (structure) |

TABLE 2-continued

| Compound No. | Structural Formula |
| --- | --- |
| 617 | (5-CF3, 2-pyrrolidin-1-yl-phenyl)-isonicotinamide |

TABLE 3

| Compound No. | Structural Formula |
| --- | --- |
| 618 | (5-CF3, 2-azepan-1-yl-phenyl)-isonicotinamide |
| 619 | (5-CF3, 2-(2,3-dihydro-1H-indol-1-yl)-phenyl)-isonicotinamide |
| 620 | (5-CF3, 2-(1,3-dihydro-2H-isoindol-2-yl)-phenyl)-isonicotinamide |
| 621 | (5-CF3, 2-(3,4-dihydroisoquinolin-2(1H)-yl)-phenyl)-isonicotinamide |
| 622 | (5-CF3, 2-piperidin-1-yl-phenyl)-4-methylbenzenesulfonamide |
| 623 | N-((4-iodo-2-chlorophenyl)carbamothioyl)nicotinamide |
| 624 | N-((5-CF3, 2-piperidin-1-yl-phenyl)carbamothioyl)nicotinamide |
| 625 | N-((3-CF3-phenyl)carbamothioyl)nicotinamide |
| 626 | N-(phenylcarbamothioyl)nicotinamide |

The present invention relates to any of the compounds shown as examples above, but of these compounds, preferable compounds are those of Compound Nos. 340, 341, 342, 343, 344, 345, 346, 347, 348, 608, 613, 615, 616, 618, 619, 620, 621, 622, 623, 624, 625, and 626; more preferable are the compounds of Compound Nos. 340, 341, 342, 343, 345, 347, 348, 608, 613, 615, 616, 618, 619, 620, 622, 623, 624, 625, and 626; still more preferable are the compounds of Compound Nos. 340, 348, 613, 616, 618, 622, and 624; and further more preferable are the compounds of Compound Nos. 340, 348, 613, 618, and 624.

The present invention also relates to any of the compounds shown above as examples. In particular, the present invention also relates to novel compounds selected from the group consisting of the compounds of Compound Nos. 341, 342, 346, 347, 348, 349, 612, 613, 614, 616, 617, 618, 619, 620, 621, 622, and 624, which are shown above as examples.

These compounds (aniline derivatives), or pharmaceutically acceptable salts or hydrates thereof, are effective as SRPK inhibitors.

The compounds (aniline derivatives), or pharmaceutically acceptable salts or hydrates thereof, are also useful as antiviral agents.

Representative methods for producing the compounds of the present invention, represented by the above formula (I), are described below.

The $R^1$, $R^2$, $R^3$, $R^4$, $R^5$, $R^6$, Q, and W below are defined as above. Room temperature means a temperature ranging from about 20 to 30° C.

Production method A

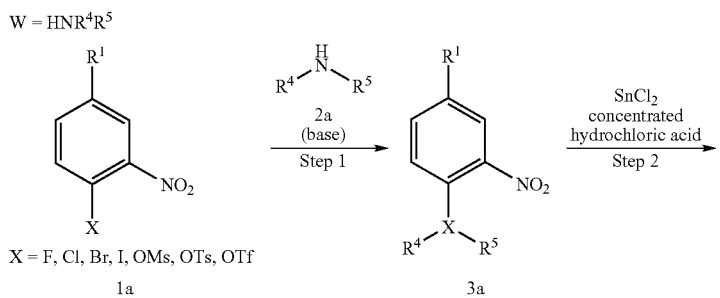

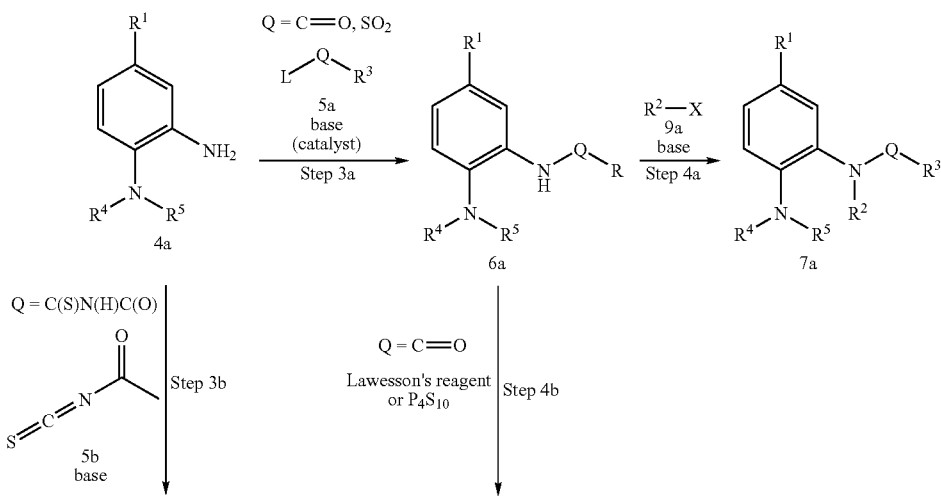

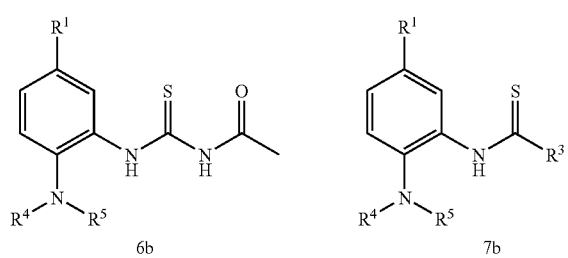

Step 1

In this step, compound 1a is reacted with compound 2a to give compound 3a. The material "nitrobenzene derivative 1a" may be available commercially or by appropriately inducing functional groups. X is a halogen atom or sulfonate used as a leaving group. Compound 2a is a reagent comprising the —NR$^5$R$^6$ to be introduced. It is preferable to use one to two equivalents of compound 2a. The reaction may be conducted in a solvent in the presence of a base.

It is possible to use triethylamine, diisopropyl ethylamine, pyridine, 4-(dimethylamino)pyridine, or such as the base. It is preferable to use one to five equivalents of base. Alternatively, an excess amount (one to five equivalents) of H—NR$^5$R$^6$ may be used as the base.

The solvents include, for example, dimethyl sulfoxide, N,N-dimethylformamide, N-methylpyrrolidone, dioxane, tetrahydrofuran, and toluene.

The reaction temperature range from 0° C. to 150° C. However, room temperature is preferable.

Step 2

In this step, the nitro group of compound 3a is reduced to an amino group to give compound 4a.

The reduction method can be to contact concentrated hydrochloric acid or such in the presence of tin chloride or such in the solvent. Alternatively, standard reduction reactions, such as catalytic hydrogenation, can also be used.

The reaction solvents include methanol, ethanol, N,N-dimethylformamide, tetrahydrofuran, 1,2-dimethoxyethane, 1,4-dioxane, and water, and mixed solvents comprising combinations thereof.

It is preferable to use a mass ratio of 1 to 20 equivalents of tin chloride or such, as a reducing agent. The reaction can be conducted at a temperature ranging from 0° C. to 100° C.

Compounds 3a and 4a may sometimes be available commercially, and in this case commercially available products may be used. In particular, when W in formula (1) is hydrogen or a halogen, the compound is usually commercially available. For example, the compounds of Compound Nos. 608, 612, and 623 to 626 shown herein are included in such compounds.

Step 3a

In this step, compound 4a is reacted with compound 5a to give compound 6a. L represents a halogen atom or such. The reaction can be conducted in a solvent in the presence of a base, and in the presence of a catalyst if required. It is preferable to use one to three equivalents of compound 5a in this reaction.

The reaction solvents include dichloromethane, chloroform, 1,4-dioxane, tetrahydrofuran, toluene, pyridine, N,N-dimethylformamide, N-methylpyrrolidone, and the like.

As the base, triethylamine, diisopropyl ethylamine, pyridine, 4-(dimethylamino)pyridine, and such may be used.

Standard amide bond-forming reactions using condensing agents can be used when L is a hydroxyl group, and standard amide bond-forming reactions can also be used when L is a leaving group, such as a succinimidyl group or imidazole group.

The catalysts include 4-(dimethylamino)pyridine and such.

The reaction temperature may range from 0° C. to 100° C.

Step 3b

In this step, compound 4a is reacted with compound 5b to give compound 6b.

The reaction can be conducted using acyl isothiocyanate in a solvent in the presence of a base. Acyl isothiocyanate may be commercially available, or may be prepared by reacting an appropriate acyl halide and thiocyanate in solution, and then used as is. It is preferable to use one to five equivalents of acyl isothiocyanate. The thiocyanates that can be used include potassium thiocyanate, sodium thiocyanate, and ammonium thiocyanate. One to five equivalents of thiocyanate are preferably used.

The solvents include, for example, acetonitrile, N,N-dimethylformamide, N-methylpyrrolidone, tetrahydrofuran, ethylene glycol dimethyl ether, and 1,4-dioxane.

The bases include, for example, triethylamine, diisopropyl ethylamine pyridine, and 4-(dimethylamino)pyridine. It is preferable to use one to five equivalents of the base.

The reaction can be conducted at a temperature ranging from 0° C. to 150° C.

Step 4a

In this step, the amide group of compound 6a is alkylated (converted into R$^2$) to give compound 7a.

The reaction can be conducted in a solvent using an alkylating agent (R$^2$—X) in the presence of a base. X is a halogen atom or sulfonate which serves as a leaving group. One to five equivalents of the alkylating agent (R$^2$—X) are preferably used.

The solvents include, for example, N,N-dimethylformamide, N-methylpyrrolidone, tetrahydrofuran, ethylene glycol dimethyl ether, 1,4-dioxane, acetonitrile, and ether.

The bases include sodium hydride, potassium hydride, lithium hydride, butyl lithium, methyl lithium, phenyl lithium, and lithiumdiisopropyl amide. One to five equivalents of base are preferably used.

The reaction can be conducted at a temperature ranging from 0° C. to 150° C.

Step 4b

In this step, the carbonyl group with an amide bond in compound 6a is converted into a thiocarbonyl group to give compound 7b.

The reaction is conducted using a thiocarbonylating agent in a solvent. The thiocarbonylating agents include, for example, Lawesson's reagent (2,4-bis(4-methoxyphenyl)-1, 3,2,4-dithiadiphosphetane 2,4-disulfide) and phosphorous pentasulfide (phosphorus decasulfide, P4S$_{10}$). It is preferable to use one to five equivalents of thiocarbonylating agent.

The solvents include, for example, toluene, benzene, chlorobenzene, xylene, N,N-dimethylformamide, N-methylpyrrolidone, ethylene glycol dimethyl ether, 1,4-dioxane, and tetrahydrofuran.

The reaction can be conducted at a temperature ranging from 0° C. to 200° C.

The above are representative methods for producing compound (I) of the present invention. The material compounds and various reagents used to produce the compounds of the present invention may form salts, hydrates, or solvates thereof, and each vary depending on the type of starting materials or solvents and such to be used; they are not particularly limited as long as they do not inhibit the reaction. The types of solvents used varies with the types of starting materials and reagents and such. Of course, the solvents are not particularly limited as long as they dissolve the starting material to some extent and do not inhibit the reaction. When compound (I) of the present invention is yielded in a free form, it can be converted according to conventional methods into a salt or hydrate thereof that may be formed by compound (I).

When compound (I) of the present invention is yielded as a salt or a hydrate thereof, it can be converted into a free form of the above compound (I) according to conventional methods.

Various isomers (for example, geometric isomers, optical isomers based on asymmetric carbons, rotational isomers, stereoisomers, and tautomers) of compound (I) of the present invention can be purified and isolated using conventional isolation means, for example, recrystallization, diastereomer salt methods, enzyme-based resolution methods, various chromatographic methods (for example, thin-layer chromatography, column chromatography, and gas chromatography).

In the present invention, SRPIN-1 analogs can be used to inhibit the activity of SRPKs. Specifically, the phosphorylation activity of SRPK1 and/or SRPK2 can be inhibited by administering the SRPIN-1 analogs described herein. The present invention relates to uses of SRPIN-1 analogs to inhibit SRPK activity. The present invention also relates to SRPK inhibitors comprising SRPIN-1 analogs. The present invention also relates to uses of SRPIN-1 analogs to produce SRPK inhibitors. Furthermore, the present invention also relates to methods for inhibiting SRPK activity, which comprises the step of contacting an SRPIN-1 analog with a SRPK. The phrase "contacting with SRPK" can mean that an SRPIN-1 analog is administered in vitro or in vivo to cells, tissues, and/or individuals expressing SRPK.

In the present invention, SRPIN-1 analogs can also be used to inhibit viral propagation. Specifically, viral propagation is inhibited when the phosphorylation activity of SRPK1 and/or SRPK2 is inhibited by administering the SRPIN-1 analogs described herein. The present invention relates to uses of SRPIN-1 analogs to inhibit viral propagation. The present invention also relates to antiviral agents comprising SRPIN-1 analogs. The present invention also relates to uses of SRPIN-1 analogs to produce antiviral agents. The present invention also relates to methods for inhibiting viral propagation, which comprise the step of contacting an SRPIN-1 analog with a SRPK. The phrase "contacting with SRPK" can mean that an SRPIN-1 analog is administered in vitro or in vivo to cells, tissues, and/or individuals expressing SRPK.

The present invention also provides packages comprising the above-descried SRPIN-1 analogs or pharmaceutically acceptable salts or hydrates thereof, where the fact that the compounds have SRPK-inhibiting and/or antiviral activity is recorded on the package or package contents. Herein a package refers to a package that contains an SRPIN-1 analog, or pharmaceutically acceptable salt or hydrate thereof. The packages may include a container for the SRPIN-1 analog or pharmaceutically acceptable salt or hydrate thereof, and may further include a bag or outer case or such to contain the container.

The present invention also provides packages comprising compounds that reduce the activity or expression level of SR proteins, where the fact that the compounds have antiviral activity is recorded on the package or package contents. In particular, the present invention provides packages in which the compound is a compound having the activity of inhibiting the expression and/or activity of an SRPK.

The compounds of the present invention can be formulated into compositions in combination with pharmaceutically acceptable carriers. For example, the compounds may be formulated into pharmaceutical compositions using known preparation techniques. When the pharmaceutical compositions of the present invention are used as SRPK inhibitors, antiviral agents (specifically, preventive or therapeutic agents for viral diseases), or other pharmaceuticals, they can be administered, for example, orally in dosage forms, such as tablets, capsules, granules, powders, pills, troches, or syrups, or parenterally in dosage forms, such as injections, aerosols, suppositories, patches, poultices, lotions, liniments, ointments, or eye drops. Such preparations are produced by known methods using additives, such as excipients, lubricants, binders, disintegrating agents, stabilizers, flavoring agents, and diluents.

Excipients include, for example, starches, such as starch, potatostarch, and cornstarch; lactate; crystalline cellulose; and calcium hydrogen phosphate.

Coating agents include, for example, ethyl cellulose, hydroxypropyl cellulose, hydroxypropylmethyl cellulose, shellac, talc, carnauba wax, and paraffin.

Binders include, for example, polyvinylpyrrolidone, Macrogol, and the same compounds as described above for the excipients.

Disintegrating agents include, for example, the same compounds as described above for the excipients; and chemically modified starches and celluloses, such as cross carmellose sodium, carboxymethyl starch sodium, and cross-linked polyvinylpyrrolidone.

Stabilizers include, for example, paraoxybenzoates such as methylparaben and propylparaben; alcohols such as chlorobutanol, benzylalcohol, and phenyl ethyl alcohol; benzalkonium chloride; phenols such as phenol and cresol; thimerosal; dehydroacetic acid; and sorbic acid.

Flavoring agents include, for example, generally used sweeteners, acidifiers, and spices.

Solvents used to produce solutions include ethanol, phenol, chlorocresol, purified water, and distilled water.

Detergents and emulsifiers include, for example, polysorbate 80, polyoxyl 40 stearate, and Lauromacrogol.

When the pharmaceutical compositions of the present invention are used as SRPK inhibitors or antiviral agents, the doses of the compound of the present invention or the pharmaceutical acceptable salts thereof are varied depending on the symptoms, age, type of administration procedure, and such. For example, depending on the symptoms, when administered orally the compounds are preferably administered at a daily dose of 0.01 mg (preferably 0.1 mg) (lower limit) to 2000 mg (preferably 500 mg, more preferably 100 mg) (upper limit) per patient (warm-blooded animals, human in particular), administered at one time or divided into several times. When administered intravenously, the compounds are preferably administered at a daily dose of 0.001 mg (preferably 0.01 mg) (lower limit) to 500 mg (preferably 50 mg) (upper limit) per adult, administered at one time or divided into several times, depending on the symptoms.

EXAMPLES

Herein below, the present invention will be specifically described using Examples, however, it is not to be construed as being limited thereto. All publications cited herein have been incorporated as parts of this description.

Silica gel (MERCK 9385-5B, 70-230 mesh) was used in column chromatography as described below. Thin-layer chromatography (TLC) was carried out using glass plates pre-coated with silica gel (MERCK 5715, silica gel 60 $F_{254}$). Melting points were measured using a Yanaco MP-500D micro melting point apparatus, manufactured by Yanaco Analytical Instruments Corp. $^1$H NMR spectra were measured using a NMR spectrometer JNM AL-400 manufactured by JEOL Ltd. $CDCl_3$ or $CD_3OD$ (ISOTEC) was used as a solvent in the measurement of NMR spectra. Chemical shift is expressed as a relative value when tetramethylsilane ((CH$_3$)$_4$Si) is used as an internal standard (0 ppm). The coupling constant (J) is shown in Hz. The symbols, s, d, t, m, and br, represent singlet, doublet, triplet, qualtet, multiplet, and broad peak, respectively.

Referential Example 1

Synthesis of SRPIN-1

Representative synthesis methods for SRPIN-1 (code name GIF-0340) are described below.

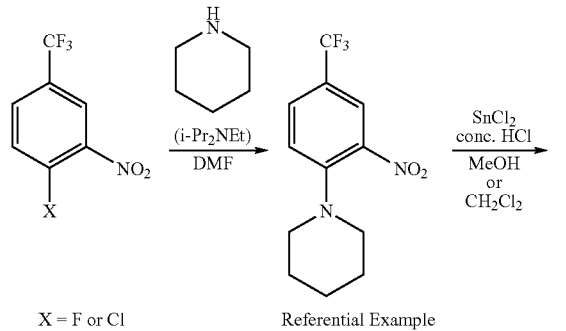

X = F or Cl

Referential Example 1-1

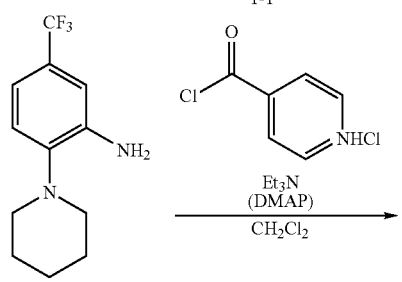

Referential Example 1-2

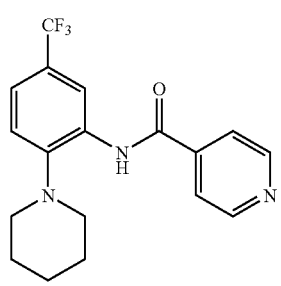

Referential Example 1-3
SRPIN-1
(GIF-0340)

Referential Example 1-1A

Piperidine (220 μl, 2.22 mmol) and N,N-diisopropylethylamine (220 μl, 2.40 mmol) were sequentially added at room temperature to an N,N-dimethylformamide (DMF; 1 ml) solution containing 1-fluoro-2-nitro-4-(trifluoromethyl)benzene (427 mg, 2.04 mmol, commercially available product). The resulting mixture was stirred for one hour. Water was added to the mixture, and the resulting mixture was extracted three times with ether. The extracted organic layer was washed with brine, dried over Na$_2$SO$_4$, filtered, and concentrated under reduced pressure.

The residue was purified by silica gel column chromatography (40 g, hexane/ethyl acetate=10/1). Thus, 1-[2-nitro-4-(trifluoromethyl)phenyl]piperidine (561 mg, 2.04 mmol, quant.) was yielded as an orange-colored solid.

The results of TLC and $^1$H NMR (CDCl$_3$, 400 MHz) are as follows: TLC R$_f$ 0.47 (hexane/acetone=16/1); $^1$H NMR (CDCl$_3$, 400 MHz) δ 1.61-1.68 (m, 2H, CH$_2$), 1.72 (tt, 4H, J=5.3, 5.3 Hz, 2CH$_2$), 3.13 (t, 4H, J=5.3 Hz, 2CH$_2$), 7.13 (d, 1H, J=8.8 Hz, aromatic) 7.61 (dd, 1H, J=2.0, 8.8 Hz, aromatic), 8.03 (d, 1H, J=2.0 Hz, aromatic).

Referential Example 1-2A

Concentrated hydrochloric acid (2.00 ml, 24.0 mmol) and anhydrous tin dichloride (2.50 g, 13.1 mmol) were sequentially added at 0° C. to a methanol (10 ml) solution containing 1-[2-nitro-4-(trifluoromethyl)phenyl]piperidine (559 mg, 2.03 mmol), obtained as described in Referential Example 1-1A. The resulting mixture was warmed to room temperature and then stirred for 17.5 hours. A saturated aqueous solution of sodium bicarbonate was added to the mixture. The resulting mixture was extracted three times with ethyl acetate. The obtained organic layer was washed with brine, dried over Na$_2$SO$_4$, filtered, and concentrated under reduced pressure. The residue was purified by silica gel column chromatography (50 g, hexane/ethyl acetate=14/1)). Thus, 2-(l-piperidinyl)-5-(trifluoromethyl)aniline (448 mg, 1.83 mmol, 90.4%) was yielded as a pale yellow solid.

The results of TLC and $^1$H NMR (CDCl$_3$, 400 MHz) are as follows: TLC R$_f$ 0.30(hexane/acetone=18/1); $^1$H NMR (CDCl$_3$, 400 MHz) δ 1.59-1.60 (m, 2H, CH$_2$), 1.71 (tt, 4H, J=5.4, 5.4 Hz, 2CH$_2$), 2.85 (brs, 4H, 2CH$_2$), 4.09 (brs, 2H, NH$_2$), 6.92 (d, 1H, J=1.9 Hz, aromatic), 6.97 (dd, 1H, J=1.9, 8.4 Hz, aromatic), 7.01 (d, 1H, J=8.4 Hz, aromatic).

Referential Example 1-3A

Isonicotinoyl chloride hydrochloride (151 mg, 0.850 mmol, commercially available product), triethylamine (450 μl, 3.23 mmol), and a catalytic amount of 4-(dimethylamino)pyridine were sequentially added at 0° C. to a dichloromethane (5 ml) solution of 2-(1-piperidinyl)-5-(trifluoromethyl)aniline (173 mg, 0.708 mmol), obtained as described in Referential Example 1-2A. The resulting mixture was warmed to room temperature and stirred for 19.5 hours. Water was added to the mixture, and the resulting mixture was extracted three times with ethyl acetate. The obtained organic layer was washed with a saturated aqueous solution of sodium bicarbonate, dried over Na$_2$SO$_4$, filtered, and concentrated under reduced pressure. The residue was purified by silica gel column chromatography (10 g, hexane/ethyl acetate=1.5/1) and recrystallization (hexane). Thus, N-[2-(1-piperidinyl)-5-(trifluoromethyl)phenyl]isonicotinamide (SRPIN-1, code name GIF-0340) (83.8 mg, 0.240 mmol, 33.9%) was yielded as a colorless solid.

The melting point, and results of TLC and $^1$H NMR (CDCl$_3$, 400 MHz), are as follows: m.p. 96-98° C.; TLC R$_f$ 0.40 (hexane/ethyl acetate=1/1); $^1$H NMR (CDCl$_3$, 400 MHz) δ 1.67-1.68 (m, 2H, CH$_2$), 1.78 (tt, 4H, J=5.5, 5.5 Hz, 2CH$_2$), 2.88 (t, 4H, J=5.5 Hz, 2CH$_2$), 7.29 (d, 1H, J=8.2 Hz, aromatic), 7.40 (dd, 1H, J=1.8, 8.2 Hz, aromatic), 7.76 (dd, 2H, J=2.0, 4.4 Hz, aromatic), 8.86 (dd, 2H, J=2.0, 4.4 Hz, aromatic), 8.87 (d, 1H, J=1.8 Hz, aromatic), 9.53 (s, 1H, NH).

Referential Example 1-1B

Piperidine (5.50 ml, 55.5 mmol, commercially available product) was added at 0° C. to an N,N-dimethylformamide (DMF; 7 ml) solution of 1-chloro-2-nitro-4-(trifluoromethyl)benzene (5.00 g, 22.4 mmol, commercially available product). The resulting mixture was stirred for 40 minutes. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (200 g, hexane/ethyl acetate=8/1). Thus, 1-[2-nitro-4-(trifluoromethyl)phenyl]piperidine (6.13 g, quant.) was yielded as an orange-colored solid.

Referential Example 1-2B

Concentrated hydrochloric acid (12.2 ml, 146 mmol) and anhydrous tin dichloride (12.7 g, 67.2 mmol) were sequentially added at 0° C. to a dichloromethane solution (10 ml) of 1-[2-nitro-4-(trifluoromethyl)phenyl]piperidine (6.13 g, 22.4 mmol), obtained as described in Referential Example 1-1 B. The resulting mixture was stirred for seven hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (200 g, hexane/ethyl acetate=15/1). Thus, 2-(1-piperidinyl)-5-(trifluoromethyl)aniline (4.55 g, 83.0%) was yielded as a pale yellow solid.

Referential Example 1-3B

Isonicotinoyl chloride hydrochloride (6.48 g, 36.4 mmol, commercially available product) and triethylamine (5.57 ml, 54.6 mmol) were sequentially added at 0° C. to a dichloromethane (10 ml) solution of 2-(1-piperidinyl)-5-(trifluoromethyl)aniline (4.45 g, 18.2 mmol) obtained as described in Referential Example 1-2B. The mixture was stirred for half an hour. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (200 g, hexane/ethyl acetate=1/1) and recrystallization. Thus, N-[2-(1-piperidinyl)-5-(trifluoromethyl)phenyl]isonicotinamide (SRPIN-1, GIF-0340) (5.49 g, 86.3%) was yielded as a colorless solid.

Referential Example 2

Synthesis of Code Name GIF-0613

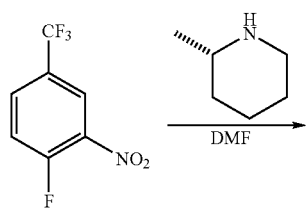

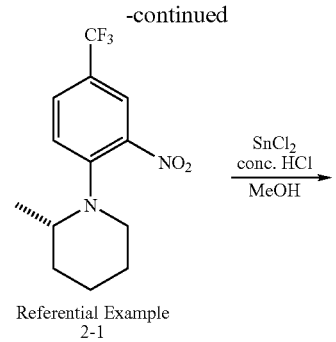

Referential Example 2-1

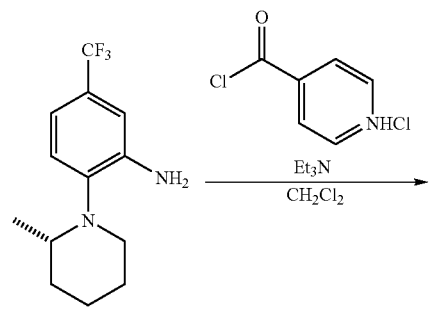

Referential Example 2-2

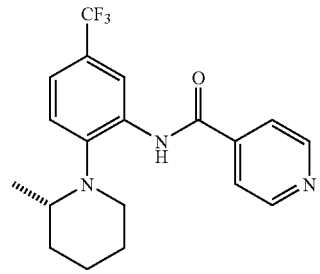

Referential Example 2-3
GIF-0613

Referential Example 2-1

(S)-2-methylpiperidine (270 µl, 2.24 mmol, commercially available product) was added at room temperature to an N,N-dimethylformamide (DMF; 0.5 ml) solution of 1-fluoro-2-nitro-4-(trifluoromethyl)benzene (211 mg, 1.00 mmol, commercially available product). The resulting mixture was stirred for two hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=12/1). Thus, (S)-1-[2-nitro-4-(trifluoromethyl)phenyl]-2-methylpiperidine (286 mg, 99.2%) was yielded as an orange-colored oily material.

TLC $R_f$ 0.44 (hexane/ethyl acetate=16/1).

Referential Example 2-2

Concentrated hydrochloric acid (1.00 ml, 12.0 mmol) and anhydrous tin dichloride (903 mg, 4.76 mmol) were sequentially added at 0° C. to a methanol (5 ml) solution of (S)-1-[2-nitro-4-(trifluoromethyl)phenyl]-2-methylpiperidine (275 mg, 0.953 mmol), obtained as described in [Referential Example 2-1]. The resulting mixture was warmed to room temperature and stirred for 17 hours. A saturated solution of sodium hydrogen carbonate was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=12/1). Thus, (S)-2-(2-methyl-1-piperidinyl)-5-(trifluoromethyl)aniline (233 mg, 94.6%) was yielded as a colorless oily material.

TLC $R_f$ 0.38 (hexane/ethyl acetate=16/1).

Referential Example 2-3

Isonicotinoyl chloride hydrochloride (466 mg, 2.61 mmol, commercially available product) and triethylamine (600 μl, 4.30 mmol) were sequentially added at 0° C. to a dichloromethane (5 ml) solution of (S)-2-(2-methyl-1-piperidinyl)-5-(trifluoromethyl)aniline (223 mg, 0.863 mmol), obtained as described in [Referential Example 2-2]. The resulting mixture was warmed to room temperature and stirred for 19.5 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (25 g, hexane/ethyl acetate=1.5/1). Thus, (S)-N-[2-(2-methyl-1-piperidinyl)-5-(trifluoromethyl)phenyl]isonicotinamide (GIF-0613) (293 mg, 93.4%) was yielded as an colorless oily material.

The results of TLC and $^1$H NMR (CDCl$_3$, 400 MHz) are as follows: TLC $R_f$ 0.40 (hexane/ethyl acetate=1/1); $^1$H NMR (CDCl$_3$, 400 MHz) δ 0.84 (d, 3H, J=6.4 Hz, CH$_3$), 1.39-1.69 (m, 3H, CH$_2$, CH), 1.82-1.86 (m, 1H, CH), 1.92-1.95 (m, 2H, CH$_2$), 2.65-2.72 (m, 1H, CH), 2.89-2.92 (m, 1H, CH), 2.98-3.02 (m, 1H, CH), 7.35 (d, 1H, J=8.4 Hz, aromatic), 7.40 (dd, 1H, J=2.2, 8.4 Hz, aromatic), 7.75 (dd, 2H, J=1.8, 4.4 Hz, aromatic), 8.86 (dd, 2H, J=1.8, 4.4 Hz, aromatic), 8.93 (d, 1H, J=1.8 Hz, aromatic), 10.1 (s, 1H, NH).

Referential Example 3

Synthesis of Code Name GIF-0617

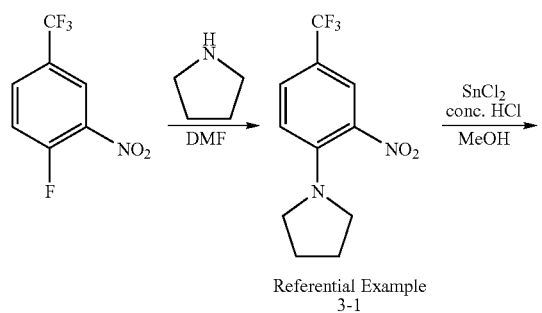

Referential Example 3-1

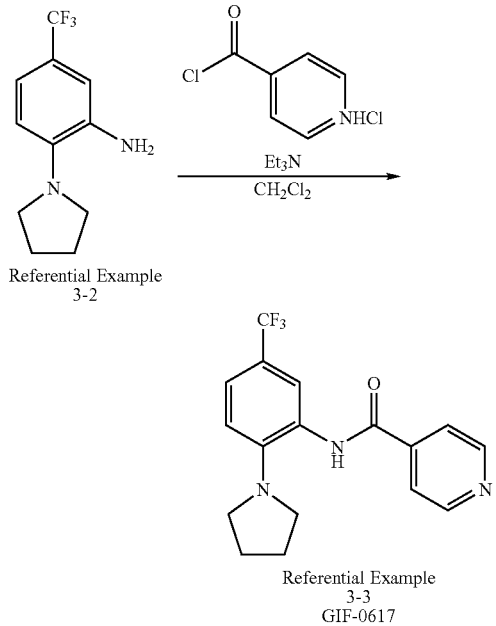

Referential Example 3-2
GIF-0617

Referential Example 3-1

Pyrrolidine ((983 μl, 12.0 mmol, commercially available product) was added at 0° C. to a N,N-dimethylformamide (DMF; 4 ml) solution of 1-fluoro-2-nitro-4-(trifluoromethyl) benzene (1.02 g, 4.89 mmol, commercially available product). The resulting mixture was warmed to room temperature and stirred for 4.5 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=5/1). Thus, 1-[2-nitro-4-(trifluoromethyl)phenyl]pyrrolidine (1.26 g, 99.3%) was yielded as an orange-colored solid.

TLC $R_f$ 0.45 (hexane/ethyl acetate=5/1).

Referential Example 3-2

Concentrated hydrochloric acid (1.36 ml, 16.3 mmol) and anhydrous tin dichloride (1.55 g, 8.16 mmol) were sequentially added at 0° C. to a methanol (4 ml) solution of 1-[2-nitro-4-(trifluoromethyl)phenyl]pyrrolidine (606 mg, 2.33 mmol), obtained as described in Referential Example 3-1. The resulting mixture was stirred for four hours. A saturated solution of sodium hydrogen carbonate was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=15/1). Thus, 1-[2-amino-4-(trifluoromethyl)phenyl]pyrrolidine (550 mg, quant.) was yielded as a red-orange colored oily material.

TLC $R_f$ 0.63 (hexane/ethyl acetate=1/1).

Referential Example 3-3

Isonicotinoyl chloride hydrochloride (705 mg, 3.96 mmol, commercially available product) and triethylamine (823 μl, 5.94 mmol) were sequentially added at 0° C. to a dichloromethane (10 ml) solution of 1-[2-amino-4-(trifluoromethyl)phenyl]pyrrolidine (516 mg, 2.24 mmol), obtained as described in Referential Example 3-2. The resulting mixture was warmed to room temperature and stirred for five hours. Water was added to the mixture, and the resulting mixture was extracted three times with dichloromethane. The obtained organic layer was washed with a saturated sodium chloride solution, dried over anhydrous sodium sulfate, filtered, and concentrated under reduced pressure. The residue was purified by silica gel column chromatography (25 g, hexane/ethyl acetate=1/2). Thus, N-[2-(1-pyrrolidinyl)-5-(trifluoromethyl)phenyl]isonicotinamide (GIF-0617) (734 mg, 97.8%) was yielded as a colorless solid.

The melting point, and results of TLC and $^1$H NMR (CDCl$_3$, 400 MHz), are as follows: m.p. 134-135° C.; TLC R$_f$ 0.29 (hexane/ethyl acetate=1/1); $^1$H NMR (CDCl$_3$, 400 MHz) δ 2.01 (tt, 4H, J=3.2 Hz, 6.4 Hz, 2CH$_2$), 3.15 (t, 4H, J=6.4 Hz, 2CH$_2$), 7.19 (d, 1H, J=8.5 Hz, aromatic), 7.38 (dd, 1H, J=2.2, 8.5 Hz, aromatic), 7.71 (dd, 2H, J=1.6, 4.4 Hz, aromatic), 8.53 (d, 1H, J=2.2, Hz, aromatic), 8.79 (s, 1H, NH), 8.83 (dd, 2H, J=1.6, 4.4 Hz, aromatic).

Referential Example 4

Synthesis of Code Name GIF-0618

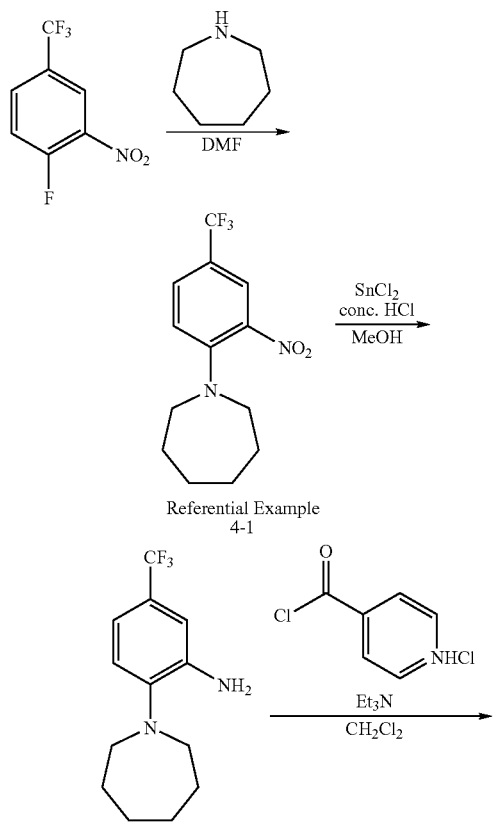

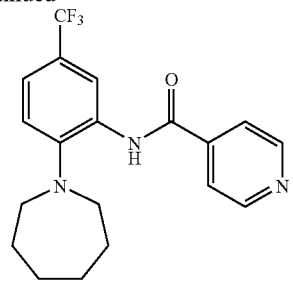

Referential Example 4-3
GIF-0618

Referential Example 4-1

Hexahydro-1H-azepine (682 μl, 6.05 mmol, commercially available product) was added at 0° C. to an N,N-dimethylformamide (DMF; 2 ml) solution of 1-fluoro-2-nitro-4-(trifluoromethyl)benzene (506 mg, 2.42 mmol, commercially available product). The resulting mixture was warmed to room temperature and stirred for one hour. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=7/1). Thus, hexahydro-1-[2-nitro-4-(trifluoromethyl)phenyl]-1H-azepine (680 mg, 97.5%) was yielded as an orange-colored solid.

The results of TLC and $^1$H NMR (CDCl$_3$, 400 MHz) are as follows: TLC R$_f$ 0.49 (hexane/ethyl acetate=5/1); $^1$H NMR (CDCl$_3$, 400 MHz) δ 1.57-1.63 (m, 4H, 2CH$_2$), 1.79-1.83 (m, 4H, 2CH$_2$), 3.31 (t, 4H, J=5.5 Hz, 2CH$_2$), 7.11 (d, 1H, J=9.1 Hz, aromatic) 7.53 (dd, 1H, J=2.0, 9.1 Hz, aromatic), 7.99 (d, 1H, J=2.0 Hz, aromatic).

Referential Example 4-2

Concentrated hydrochloric acid (1.27 ml, 15.2 mmol) and anhydrous tin dichloride (1.43 g, 7.54 mmol) were sequentially added at 0° C. to a methanol (5 ml) solution of hexahydro-1-[2-nitro-4-(trifluoromethyl)phenyl]-1H-azepine (675 mg, 2.34 mmol), obtained as described in Referential Example 4-1. The resulting mixture was stirred for two hours. A saturated solution of sodium hydrogen carbonate was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=20/1). Thus, 1-[2-amino-4-(trifluoromethyl)phenyl]-hexahydro-1H-azepine (522 mg, 86.3%) was yielded as a colorless solid.

The results of TLC and $^1$H NMR (CDCl$_3$, 400 MHz) are as follows: TLC R$_f$ 0.81 (hexane/ethyl acetate=3/1); $^1$H NMR (CDCl$_3$, 400 MHz) δ 1.70-1.84 (m, 8H, 4CH$_2$), 3.04 (t, 4H, J=5.4, Hz, 2CH$_2$), 4.10 (brs, 2H, NH$_2$), 6.92 (d, 1H, J=1.2 Hz, aromatic), 6.94 (dd, 1H, J=1.2, 7.9 Hz, aromatic), 7.05 (d, 1H, J=7.9 Hz, aromatic).

Referential Example 4-3

Isonicotinoyl chloride hydrochloride (704 mg, 3.95 mmol, commercially available product) and triethylamine (823 μl, 5.94 mmol) were sequentially added at 0° C. to a dichloromethane (6 ml) solution of 1-[2-amino-4-(trifluoromethyl)phenyl]-hexahydro-1H-azepine (512 mg, 1.98 mmol), obtained as described in Referential Example 4-2. The resulting mixture was stirred for one and a half hours. Water was added to the mixture, and the resulting mixture was extracted three times with dichloromethane. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=2/1). Thus, N-[2-(1-hexahydro-1H-azepinyl)-5-(trifluoromethyl)phenyl]isonicotinamide (GIF-0618) (697 mg, 97.0%) was yielded as a colorless solid.

The melting point, and results of TLC and $^1$H NMR (CDCl$_3$, 400 MHz), are as follows: m.p. 138-139° C.; TLC R$_f$ 0.40 (hexane/ethyl acetate=1/1); $^1$H NMR (CDCl$_3$, 400 MHz) δ 1.79 (br, 8H, 4CH$_2$), 3.06-3.10 (m, 4H, 2CH$_2$), 7.31 (d, 1H, J=8.2 Hz, aromatic), 7.37 (dd, 1H, J=1.6, 8.2 Hz, aromatic), 7.76 (dd, 2H, J=2.0, 6.0 Hz, aromatic), 8.85 (m, 3H, aromatic), 9.66 (s, 1H, NH).

Referential Example 5

Synthesis of Code Name GIF-0346

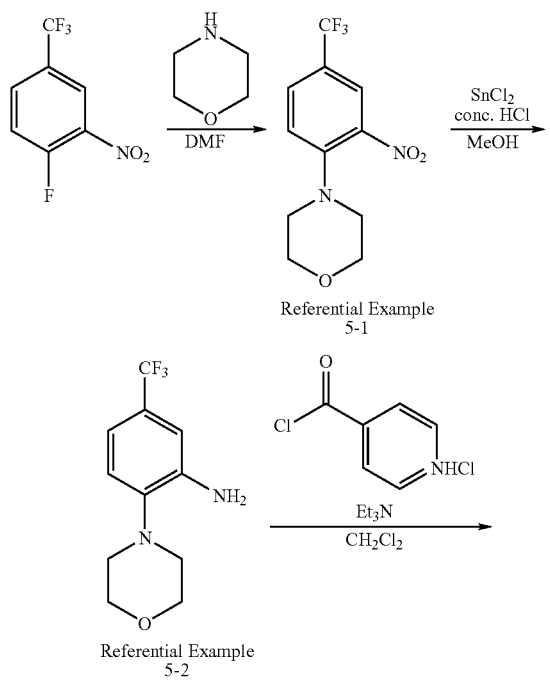

Referential Example 5-2

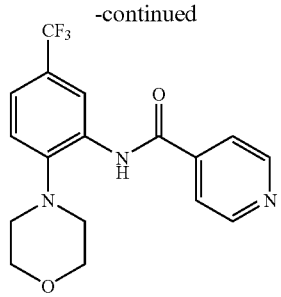

Referential Example 5-3
GIF-0346

Referential Example 5-1

Morpholine (190 μl, 2.17 mmol, commercially available product) was added at room temperature to an N,N-dimethylformamide (DMF; 0.5 ml) solution of 1-fluoro-2-nitro-4-(trifluoromethyl)benzene (209 mg, 1.00 mmol, commercially available product). The resulting mixture was stirred for three hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=3/1). Thus, 4-[2-nitro-4-(trifluoromethyl)phenyl]morpholine (270 mg, 97.7%) was yielded as an orange-colored oily material.

TLC R$_f$ 0.27 (hexane/ethyl acetate=3/1).

Referential Example 5-2

Concentrated hydrochloric acid (1.00 ml, 12.0 mmol) and anhydrous tin dichloride (905 mg, 4.77 mmol) were sequentially added at 0° C. to a methanol (5 ml) solution of 4-[2-nitro-4-(trifluoromethyl)phenyl]morpholine (263 mg, 0.952 mmol), obtained as described in Referential Example 5-1. The resulting mixture was warmed to room temperature and stirred for 20 hours. A saturated solution of sodium hydrogen carbonate was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=2/1). Thus, 4-[2-amino-4-(trifluoromethyl)phenyl]morpholine (214 mg, 91.2%) was yielded as a colorless solid.

TLC R$_f$ 0.31 (hexane/ethyl acetate=3/1).

Referential Example 5-3

Isonicotinoyl chloride hydrochloride (320 mg, 1.80 mmol, commercially available product) and triethylamine (480 μl, 3.44 mmol) were sequentially added at 0° C. to a dichloromethane (5 ml) solution of 4-[2-amino-4-(trifluoromethyl)phenyl]morpholine (196 mg, 0.796 mmol), obtained as described in Referential Example 5-2. The resulting mixture was warmed to room temperature and stirred for 60 hours. Water was added to the mixture, and the resulting mixture was extracted three times with dichloromethane. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=2/1). Thus, N-[2-(4-morpholinly)-5-(trifluoromethyl)phenyl]isonicotinamide (GIF-0346) (65.1 mg, 23.2%) was yielded as a colorless solid.

The melting point, and results of TLC and $^1$H NMR (CDCl$_3$, 400 MHz), are as follows: m.p. 172-173° C.; TLC R$_f$ 0.23 (hexane/ethyl acetate=1/3); $^1$H NMR (CDCl$_3$, 400 MHz) δ 2.96 (t, 4H, J=4.4 Hz, 2CH$_2$), 3.92 (t, 4H, J=4.4 Hz, 2CH$_2$), 7.34 (d, 1H, J=8.4 Hz, aromatic), 7.44 (dd, 1H, J=1.6, 8.4 Hz, aromatic), 7.75 (dd, 1H, J=1.6, 4.4 Hz, aromatic), 8.87-8.88 (m, 3H, aromatic) 9.48 (s, 1H, NH).

Referential Example 6

Synthesis of Code Name GIF-0347

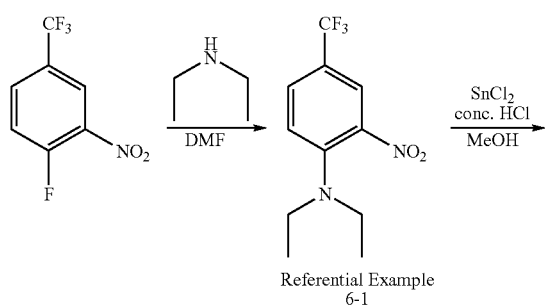
Referential Example 6-1

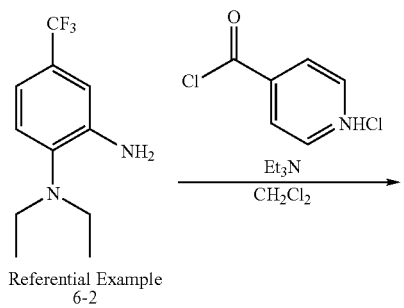
Referential Example 6-2

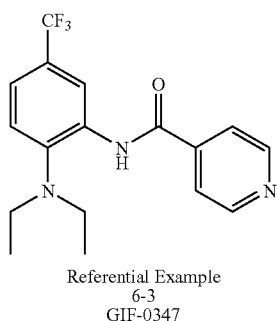
Referential Example 6-3
GIF-0347

Referential Example 6-1

Diethylamine (230 μl, 2.22 mmol, commercially available product) was added at room temperature to an N,N-dimethylformamide (DMF; 0.5 ml) solution of 1-fluoro-2-nitro-4-(trifluoromethyl)benzene (211 mg, 1.01 mmol, commercially available product). The resulting mixture was stirred for three hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=8/1). Thus, 1-diethylamino-2-nitro-4-(trifluoromethyl)benzene (258 mg, 98.3%) was yielded as an orange-colored oily material.

TLC R$_f$ 0.37 (hexane/ethyl acetate/ether=16/1/1).

Referential Example 6-2

Concentrated hydrochloric acid (1.00 ml, 12.0 mmol) and anhydrous tin dichloride (908 mg, 4.78 mmol) were sequentially added at 0° C. to a methanol (5 ml) solution of 1-diethylamino-2-nitro-4-(trifluoromethyl)benzene (251 mg, 0.957 mmol), obtained as described in Referential Example 6-1. The resulting mixture was warmed to room temperature and stirred for 22 hours. A saturated solution of sodium hydrogen carbonate was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=20/1-10/1). Thus, 2-amino-1-diethylamino-4-(trifluoromethyl)benzene (144 mg,. 64.7%) was yielded as a colorless oily material.

TLC R$_f$ 0.22 (hexane/ethyl acetate=30/1).

Referential Example 6-3

Isonicotinoyl chloride hydrochloride (88.2 mg, 0.495 mmol, commercially available product) and triethylamine (140 μL, 1.00 mmol) were sequentially added at 0° C. to a dichloromethane (3 ml) solution of 2-amino-1-diethylamino-4-(trifluoromethyl)benzene (103 mg, 0.443 mmol), obtained as described in Referential Example 6-2. The resulting mixture was warmed to room temperature and stirred for one and a half hours. Water was added to the mixture, and the resulting mixture was extracted three times with dichloromethane. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=2/1). Thus, N-[2-diethylamino-5-(trifluoromethyl)phenyl]isonicotinamide (GIF-0347) (51.0 mg, 34.1%) was yielded as a colorless solid.

The melting point, and results of TLC and $^1$H NMR (CDCl$_3$, 400 MHz), are as follows: m.p. 78-80° C.; TLC R$_f$ 0.31 (hexane/ethyl acetate=1/1); $^1$H NMR (CDCl$_3$, 400 MHz) δ 1.01 (t, 6H, J=7.1 Hz, 2CH$_3$), 3.04 (q, 4H, J=7.1 Hz, 2CH$_2$), 7.33 (d, 1H, J=8.2 Hz, aromatic), 7.41 (dd, 1H, J=1.8, 8.2 Hz, aromatic), 7.73 (dd, 2H, J=1.8, 4.4 Hz, aromatic), 8.60 (d, 1H, J=2.6 Hz, aromatic), 8.85 (dd, 2H, J=1.8, 4.4 Hz, aromatic), 8.91 (d, 1H, J=1.8 Hz, aromatic) 9.90 (s, 1H, NH).

Referential Example 7

Synthesis of Code Name GIF-0343

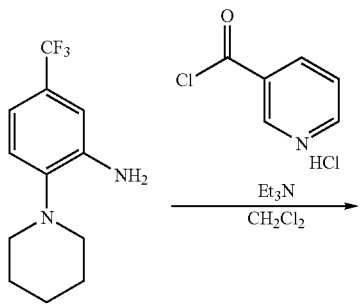

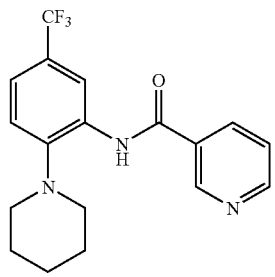

Referential Example 7
GIF-0343

Referential Example 8

Synthesis of Code Name GIF-0344

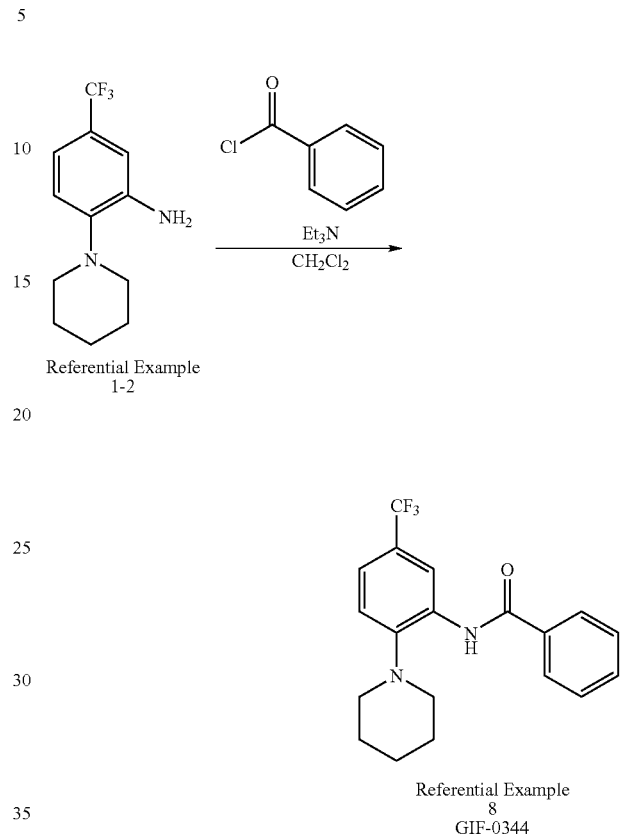

Nicotinoyl chloride hydrochloride (122 mg, 0.685 mmol, commercially available product) and triethylamine (250 μl, 1.79 mmol) were sequentially added at 0° C. to a dichloromethane (5 ml) solution of 2-(1-piperidinyl)-5-(trifluoromethyl)aniline (152 mg, 0.622 mmol), obtained as described in Referential Example 1-2. The resulting mixture was warmed to room temperature and stirred for 16.5 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (15 g, hexane/ethyl acetate=1.5/1-1/1). Thus, N-[2-(1-piperidinyl)-5-(trifluoromethyl)phenyl]nicotinamide (GIF-0343) (98.4 mg, 45.3%) was yielded as a colorless solid.

The melting point, and results of TLC and $^1$H NMR (CDCl$_3$, 400 MHz), are as follows: m.p. 145-146° C.; TLC R$_f$ 0.40 (hexane/ethyl acetate=1/1); $^1$H NMR (CDCl$_3$, 400 MHz) δ 1.62-1.69 (m, 2H, CH$_2$), 1.79 (tt, 4H, J=5.8, 5.8 Hz, 2CH$_2$), 2.88 (t, 4H, J=5.8 Hz, 2CH$_2$), 7.29 (d, 1H, J=8.4 Hz, aromatic), 7.39 (dd, 1H, J=2.0, 8.4 Hz, aromatic), 7.51 (dd, 1H, J=4.8, 8.0 Hz, aromatic), 8.30 (ddd, 1H, J=1.6, 2.4, 8.0 Hz, aromatic), 8.82 (dd, 1H, J=1.6, 4.8 Hz, aromatic), 8.87 (d, 1H, J=2.0 Hz, aromatic), 9.16 (d, 1H, J=2.4 Hz, aromatic), 9.53 (s, 1H, NH).

Benzoyl chloride (50.0 μl, 0.430 mmol, commercially available product) and triethylamine (170 μl, 1.21 mmol) were sequentially added at 0° C. to a dichloromethane (3 ml) solution of 2-(1-piperidinyl)-5-(trifluoromethyl)aniline (102 mg, 0.417 mmol), obtained as described in Referential Example 1-2. The resulting mixture was warmed to room temperature and stirred for 18 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=10/1). Thus, N-[2-(1-piperidinyl)-5-(trifluoromethyl)phenyl]benzamide (GIF-0344) (126 mg, 86.7%) was yielded as a colorless solid.

The melting point, and results of TLC and $^1$H NMR (CDCl$_3$, 400 MHz), are as follows: m.p. 128-129° C.; TLC R$_f$ 0.46 (hexane/ethyl acetate=4/1); $^1$H NMR (CDCl$_3$, 400 MHz) δ 1.62-1.70 (m, 2H, CH$_2$), 1.78 (tt, 4H, J=5.2, 5.2 Hz, 2CH$_2$), 2.88 (t, 4H, J=5.2 Hz, 2CH$_2$), 7.26 (d, 1H, J=8.6 Hz, aromatic), 7.35 (d, 1H, J=0.8, 8.6 Hz, aromatic), 7.52-7.61 (m, 1H, aromatic), 8.10 (m, 2H, aromatic), 7.94 (m, 2H, aromatic), 8.91 (d, 1H, J=0.8 Hz, aromatic), 9.44 (s, 1H, NH).

Referential Example 9

Code Name GIF-0345

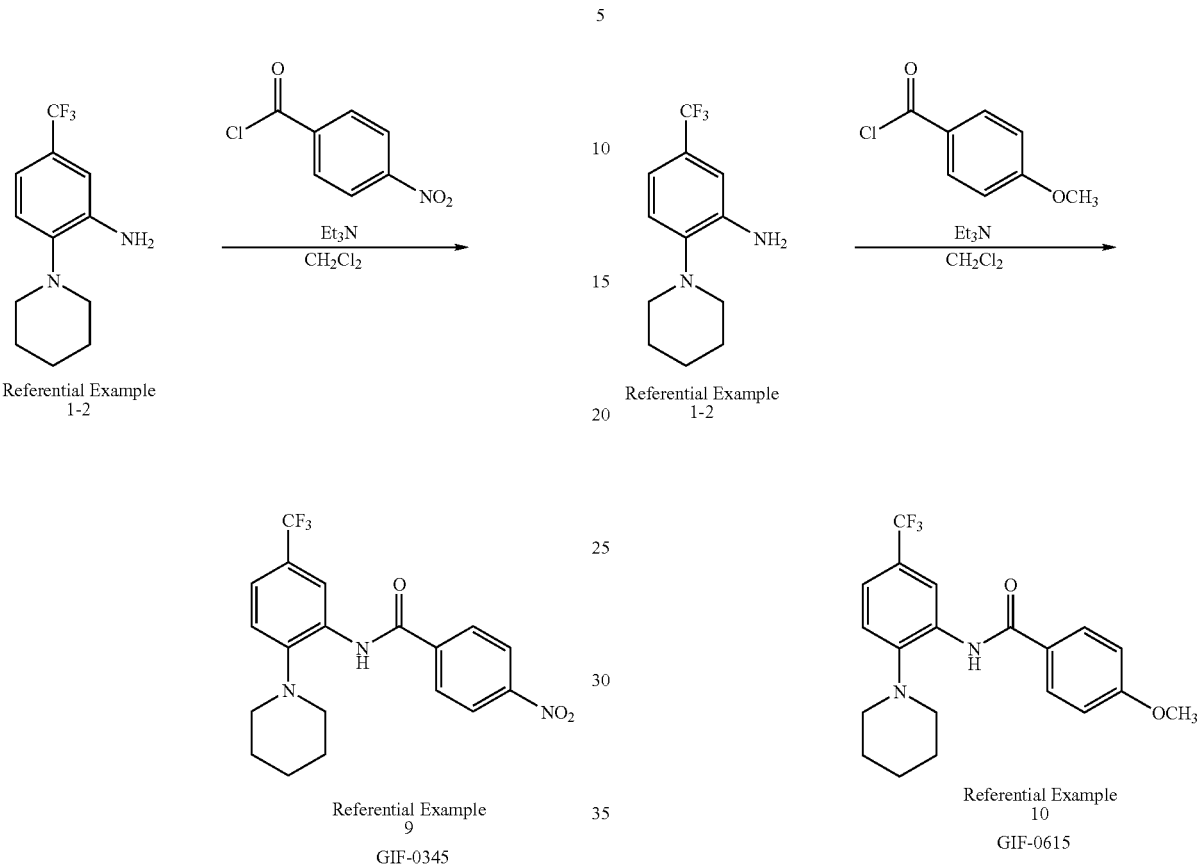

4-Nitrobenzoyl chloride (64.2 mg, 0.345 mmol, commercially available product) and triethylamine (120 μl, 0.859 mmol) were sequentially added at 0° C. to a dichloromethane (2 ml) solution of 2-(1-piperidinyl)-5-(trifluoromethyl)aniline (51.2 mg, 0.209 mmol), obtained as described in Referential Example 1-2. The resulting mixture was warmed to room temperature and stirred for 60 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=8/1-6/1). Thus, N-[2-(1-piperidinyl)-5-(trifluoromethyl)phenyl]-4-nitrobenzamide (GIF-0345) (46.3 mg, 56.3%) was yielded as a yellow solid.

The melting point, and results of TLC and $^1$H NMR (CDCl$_3$, 400 MHz), are as follows: m.p. 125-136° C.; TLC R$_f$ 0.33 (hexane/ethyl acetate=4/1); $^1$H NMR (CDCl$_3$, 400 MHz) δ 1.62-1.70 (m, 2H, CH$_2$), 1.77 (tt, 4H, J=5.0, 5.0 Hz, 2CH$_2$), 2.88 (t, 4H, J=5.0 Hz, 2C$_2$), 7.30 (d, 1H, J=8.0 Hz, aromatic), 7.40 (dd, 1H, J=1.6, 8.2 Hz, aromatic), 8.10 (dd, 2H, J=1.8, 6.8 Hz, aromatic), 8.41 (d, 2H, J=1.8, 6.8 Hz, aromatic), 8.86 (d, 1H, J=2.0 Hz, aromatic), 9.54 (s, 1H, NH).

Referential Example 10

Synthesis of Code Name GIF-0615

4-Methoxybenzoyl chloride (250 mg, 1.47 mmol, commercially available product) and triethylamine (254 μl, 1.83 mmol) were sequentially added at 0° C. to a dichloromethane (4 ml) solution of 2-(1-piperidinyl)-5-(trifluoromethyl)aniline (147 mg, 0.602 mmol), obtained as described in Referential Example 1-2. The resulting mixture was warmed to room temperature and stirred for 17 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=5/1). Thus, N-[2-(1-piperidinyl)-5-(trifluoromethyl)phenyl]-4-methoxybenzamide (GIF-0615) (240 mg, quant.) was yielded as a colorless solid.

The melting point, and results of TLC and $^1$H NMR (CDCl$_3$, 400 MHz), are as follows: m.p. 111-114° C.; TLC R$_f$ 0.33 (hexane/ethyl acetate=4/1); $^1$H NMR (CDCl$_3$, 400 MHz) δ 1.64-1.68 (m, 2H, CH$_2$), 1.78 (tt, 4H, J=5.4, 5.4 Hz, 2CH$_2$), 1.60-1.70 (m, 2H, CH$_2$), 2.39-2.41 (m, 2H, CH$_2$), 2.87 (t, 4H, J=5.4 Hz, 2CH$_2$), 3.89 (s, 3H, CH$_3$), 7.03 (dd, 2H, J=2.0, 7.0 Hz, aromatic), 7.23 (d, 1H, J=8.0 Hz, aromatic), 7.32 (dd, 1H, J=1.6, 8.0 Hz, aromatic), 7.91 (dd, 2H, J=2.0, 7.0 Hz, aromatic), 8.88 (d, 1H, J=1.6 Hz, aromatic), 9.34 (s, 1H, NH).

Referential Example 11

Synthesis of Code Name GIF-0622

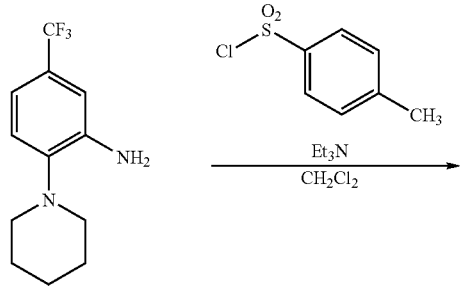

Referential Example 1-2

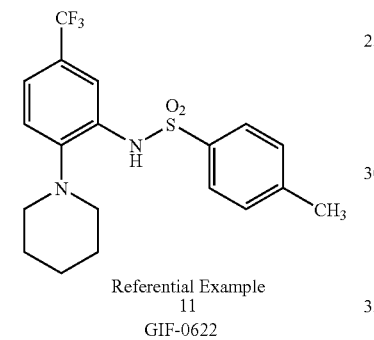

Referential Example 11
GIF-0622 p-Toluenesulfonyl chloride (233 g, 1.22 mmol, commercially available product) and triethylamine (254 µl, 1.83 mmol) were sequentially added at room temperature to a dichloromethane (5 ml) solution of 2-(1-piperidinyl)-5-(trifluoromethyl)aniline (149 mg, 0.610 mmol), obtained as described in Referential Example 1-2. The resulting mixture was stirred for 60 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=10/1). Thus, N-[2-(1-piperidinyl)-5-(trifluoromethyl)phenyl]-p-toluenesulfonamide (GIF-0622) (243 mg, quant) was yielded as a colorless solid.

The melting point, and results of TLC and $^1$H NMR (CDCl$_3$, 400 MHz), are as follows: m.p. 117-134° C.; TLC R$_f$ 0.49 (hexane/ethyl acetate=5/1); $^1$H NMR (CDCl$_3$, 400 MHz) δ 1.55-1.60 (m, 2H, CH$_2$), 1.66 (tt, 4H, J=5.2, 5.2 Hz, 2CH$_2$), 2.36 (s, 3H, CH$_3$), 2.51 (t, 4H, J=5.2 Hz, 2CH$_2$), 7.11 (d, 1H, J=8.0 Hz, aromatic), 7.22-7.28 (m, 3H, aromatic), 7.71 (dd, 2H, J=1.8, 8.6 Hz, aromatic), 7.85 (d, 1H, J=2.0 Hz, aromatic), 7.94 (s, 1H, NH).

Referential Example 12

Synthesis of Code Name GIF-0624

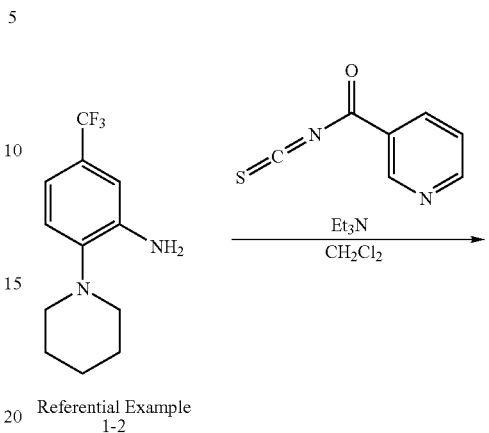

Referential Example 1-2

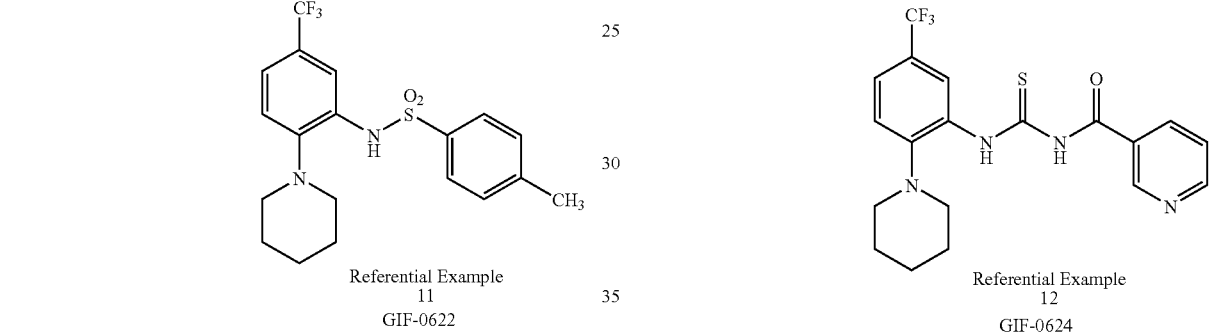

Referential Example 12
GIF-0624

An acetonitrile (15 ml) solution containing potassium thiocyanate (119 mg, 1.22 mmol, commercially available product) and nicotinoyl chloride hydrochloride (352 mg, 1.97 mmol, commercially available product) was stirred at 70° C. for 40 minutes. The mixture was cooled to room temperature, and then an acetonitrile (5 ml) solution of 2-(1-piperidinyl)-5-(trifluoromethyl)aniline (244 mg, 1.00 mmol), obtained as described in Referential Example 1-2, and triethylamine (278 µl, 2.00 mmol) were sequentially added thereto. The resulting mixture was stirred at 50° C. for one hour. Water was added to the mixture, and the resulting mixture was extracted three times with dichloromethane. The obtained organic layer was washed with a saturated sodium chloride solution, dried over anhydrous sodium sulfate, filtered, and concentrated under reduced pressure. The residue was purified by silica gel column chromatography (25 g, hexane/ethyl acetate=4/1-1/1). Thus, 1-nicotinoyl-3-[2-(1-piperidinyl)-5-(trifluoromethyl)phenyl]thiourea (GIF-0624) (383 mg, 93.7%) was yielded as a pale yellow solid.

The melting point, and results of TLC and $^1$H NMR (CD$_3$OD, 400 MHz), are as follows: m.p. 142-144° C.; TLC R$_f$ 0.26 (hexane/ethyl acetate=1/1); $^1$H NMR (CDCl$_3$, 400 MHz) δ 1.58-1.67 (m, 2H, CH$_2$), 1.75-1.85 (m, 4H, 2CH$_2$), 2.89-2.95 (m, 4H, 2CH$_2$), 7.33-7.40 (m, 1H, aromatic), 7.44-7.48 (m, 1H, aromatic), 7.60-7.65 (m, 1H, aromatic), 8.76-8.78 (m, 1H, aromatic), 9.05 (s, 0.6H, aromatic), 9.09-9.14 (m, 1H, aromatic), 8.37-8.39 (m, 1H, aromatic), 8.49 (s, 0.4H, aromatic).

Referential Example 13

Synthesis of Code Name GIF-0614

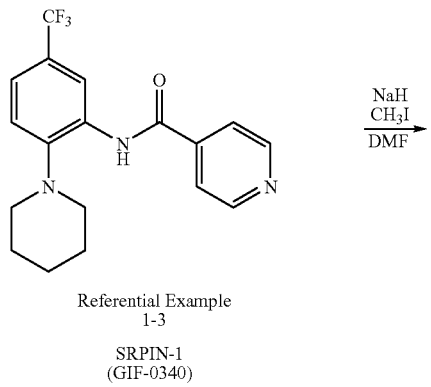

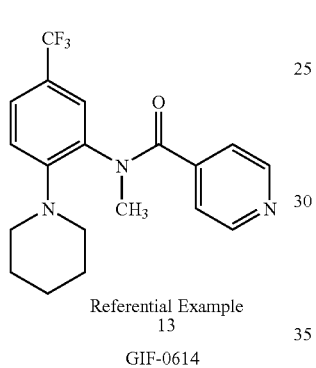

Sodium hydride (60% (w/w) oil mixture) (200 mg, 0.500 mmol) was added at 0° C. to an N,N-dimethylformamide (DMF; 0.5 ml) solution of 5 N-[2-(1-piperidinyl)-5-(trifluoromethyl)phenyl]isonicotinamide (SRPIN-1, GIF-0340) (121 mg, 0.496 mmol), obtained as described in Referential example 1-3. The resulting mixture was stirred for one hour, and an N,N-dimethylformamide (DMF) solution of methyl iodide (0.8 M, 0.62 ml, 0.496 mmol) was added thereto at 0° C. The resulting mixture was stirred for three hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (12 g, hexane/ethyl acetate=1/1). Thus, N-methyl-N-[2-(1-piperidinyl)-5-(trifluoromethyl)phenyl]isonicotinamide (GIF-0614) (65.9 mg, 51.5%) was yielded as a colorless solid.

The melting point, and results of TLC and $^1$H NMR (CDCl$_3$, 400 MHz), are as follows: m.p. 119-121° C.; TLC R$_f$ 0.36 (hexane/ethyl acetate=1/1); $^1$H NMR (CDCl$_3$, 400 MHz) δ 1.50-1.60 (m, 2H, CH$_2$), 1.60-1.70 (m, 2H, CH$_2$), 1.60-1.70 (m, 2H, CH$_2$), 2.39-2.41 (m, 2H, CH$_2$), 2.80-2.82 (m, 2H, CH$_2$), 3.20 (s, 3H, CH$_3$), 6.86 (d, 1H, J=8.3 Hz, aromatic), 7.15 (d, 2H, J=4.4 Hz, aromatic), 7.41 (d, 2H, J=8.3 Hz, aromatic), 7.48 (s, 1H, aromatic), 8.44 (d, 2H, J=4.4 Hz, aromatic).

Referential Example 14

Synthesis of Code Name GIF-0616

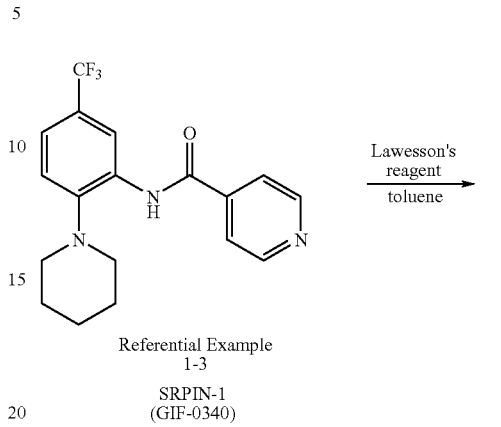

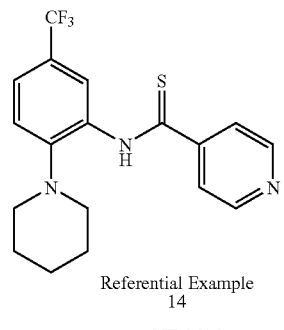

Lawesson's reagent (328 mg, 0.811 mmol, commercially available product) was added to a toluene (2.5 ml) solution of N-[2-(1-piperidinyl)-5-(trifluoromethyl)phenyl]isonicotinamide (SRPIN-1, GIF-0340) (528 mg, 1.51 mmol), obtained as described in Referential Example 1-3, and the resulting mixture was stirred with refluxing at 100° C. for 12 hours. The mixture was cooled to room temperature, and then an aqueous solution of 2 M sodium hydroxide was added thereto to alkalify the solution. The mixture was reverse extracted three times with an aqueous solution of 12 M sodium hydroxide. 2 M hydrochloric acid was added to the aqueous layer to acidify the solution. Then, the resulting mixture was extracted three times with ether. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=1/1). Thus, N-[2-(1-piperidinyl)-5-(trifluoromethyl)phenyl]isonicotinthioamide (GIF-0616) (186 mg, 33.7%) was yielded as a colorless solid.

The melting point, and results of TLC and $^1$H NMR (CDCl$_3$, 400 MHz), are as follows: m.p. 108-109° C.; TLC R$_f$ 0.27 (hexane/ethyl acetate=1/1); $^1$H NMR (CDCl$_3$, 400 MHz) δ

1.61-1.62 (m, 2H, CH$_2$), 1.68 (tt, 4H, J=5.0, 5.0 Hz, 2CH$_2$), 2.87 (t, 4H, (d, 1H, J=7.8 Hz, aromatic), 7.51 (dd, 1H, J=1.6 Hz, aromatic), 7.71 (dd, 2H, J=1.6, 6.4 Hz, aromatic), 8.76 (dd, 2H, J=1.6, 6.4 Hz, aromatic), 9.58 (d, 1H, J=1.6 Hz, aromatic), 10.5 ((s, 1H, NH).

Referential Example 15

Synthesis of Code Name GIF-0341

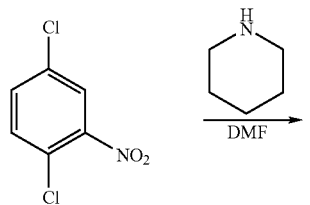

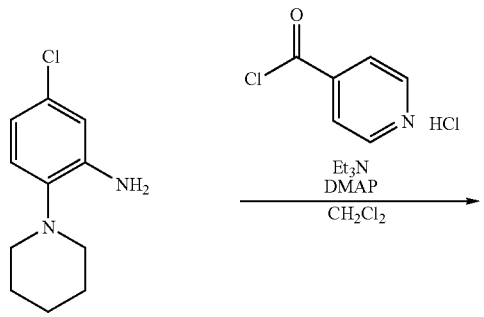

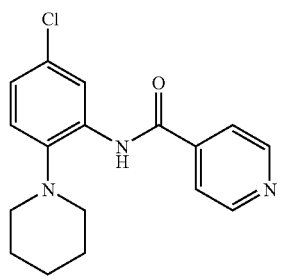

Referential Example 15-1

Piperidine (660 µl, 6.66 mmol, commercially available product) was added at room temperature to an N,N-dimethylformamide (DMF; 1 ml) solution of 1,4-dichloro-2-nitrobenzene (390 mg, 2.03 mmol, commercially available product). The resulting mixture was stirred for 18.5 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=10/1). Thus, 1-(4-chloro-2-nitrophenyl)piperidine (471 mg, 96.4%) was yielded as an orange-colored oily material.

TLC $R_f$ 0.18 (hexane alone).

Referential Example 15-2

Concentrated hydrochloric acid (2.00 ml, 24.0 mmol) and anhydrous tin dichloride (1.84 g, 9.70 mmol) were sequentially added at 0° C. to a methanol (10 ml) solution of 1-(4-chloro-2-nitrophenyl)piperidine (471 mg, 1.95 mmol), obtained as described in Referential Example 15-1. The resulting mixture was warmed to room temperature and stirred for 16 hours. A saturated aqueous solution of sodium bicarbonate was added to the mixture. The mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=9/1). Thus, 5-chloro-2-(1-piperidinyl)aniline (388 mg, 94.3%) was yielded as a colorless oily material.

TLC $R_f$ 0.26 (hexane/ethyl acetate=18/1).

Referential Example 15-3

Isonicotinoyl chloride hydrochloride (350 mg, 1.96 mmol, commercially available product), triethylamine (740 µl, 5.30 mmol), and a catalytic amount of 4-(dimethylamino)pyridine were sequentially added at room temperature to a dichloromethane (10 ml) solution of 5-chloro-2-(1-piperidinyl)aniline (378 mg, 1.79 mmol), obtained as described in Referential Example 15-2. The resulting mixture was stirred for 19 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (200 g, hexane/ethyl acetate=1/1). Thus, N-[5-chloro-2-(1-piperidinyl)phenyl]isonicotinamide (GIF-0341) (180 mg, 31.8%) was yielded as a colorless solid.

The melting point, and results of TLC and $^1$H NMR (CDCl$_3$, 400 MHz), are as follows: m.p. 141-143° C.; TLC $R_f$ 0.32 (hexane/ethyl acetate=1/1); $^1$H NMR (CDCl$_3$, 400 MHz) δ 1.61-1.62 (m, 2H, CH$_2$), 1.76 (tt, 4H, J=5.0, 5.0 Hz, 2CH$_2$), 2.82 (t, 4H, J=5.0 Hz, 2CH$_2$), 7.09 (dd, 1H, J=2.6, 8.8 Hz, aromatic), 7.14 (d, 1H, J=8.8 Hz, aromatic), 7.75 (dd, 2H, J=1.6, 4.4 Hz, aromatic), 8.60 (d, 1H, J=2.6 Hz, aromatic), 8.85 (dd, 2H, J=1.6, 4.4 Hz, aromatic), 9.66 (s, 1H, NH).

Referential Example 16

Synthesis of Code Name GIF-0342

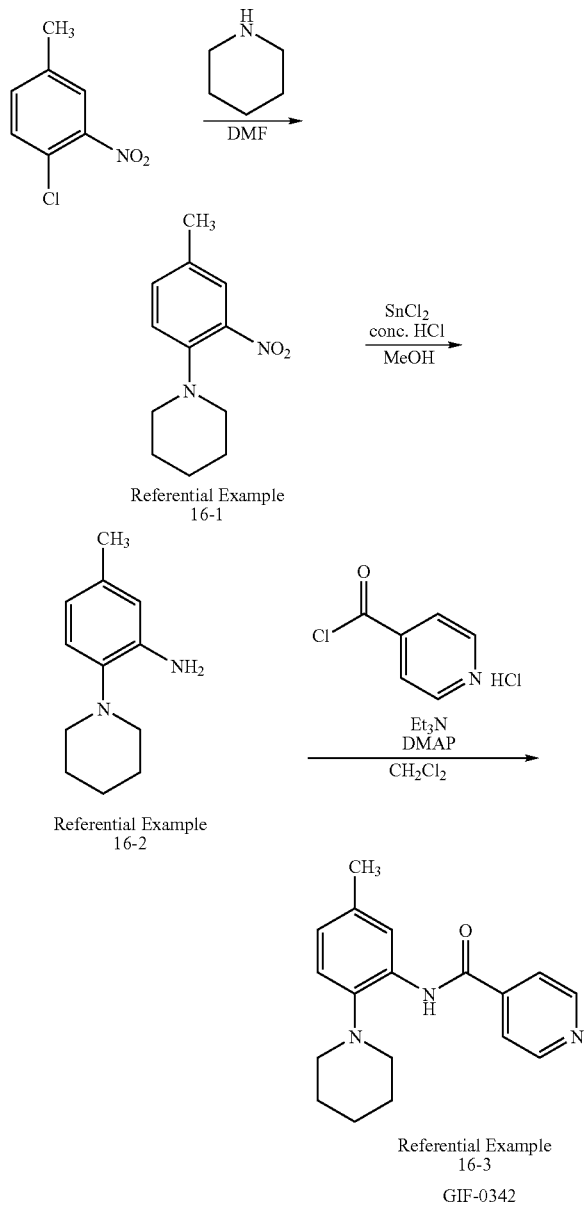

Referential Example 16-1

Piperidine (660 μl, 6.66 mmol, commercially available product) was added at room temperature to an N,N-dimethylformamide (DMF; 1 ml) solution of 4-chloro-3-nitrotoluene (358 mg, 2.08 mmol, commercially available product). The resulting mixture was stirred at 100° C. for 17 hours. The mixture was cooled to room temperature, and then water was added thereto. The resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=50/1). Thus, 1-(4-methyl-2-nitrophenyl)piperidine (212 mg, 46.2%) was yielded as a colorless oily material. TLC $R_f$ 0.54 (hexane/ethyl acetate=10/1).

Referential Example 16-2

Concentrated hydrochloric acid (0.70 ml, 8.4 mmol) and anhydrous tin dichloride (834 mg, 4.39 mmol) were sequentially added at 0° C. to a methanol (5 ml) solution of 1-(4-methyl-2-nitrophenyl)piperidine (212 mg, 0.880 mmol), obtained as described in Referential Example 16-1. The resulting mixture was warmed to room temperature and stirred for 16 hours. A saturated aqueous solution of sodium bicarbonate was added to the mixture. The mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=12/1). Thus, 5-methyl-2-(1-piperidinyl)aniline (164 mg, 95.0%) was yielded as a pale yellow oily material.

TLC $R_f$ 0.36 (hexane/ethyl acetate=10/1)

Referential Example 16-3

Isonicotinoyl chloride hydrochloride (172 mg, 0.966 mmol, commercially available product), triethylamine (340 μl, 2.44 mmol), and a catalytic amount of 4-(dimethylamino)pyridine were sequentially added at room temperature to a dichloromethane (5 ml) solution of 5-methyl-2-(1-piperidinyl)aniline (155 mg, 0.815 mmol), obtained as described in Referential Example 16-2. The resulting mixture was stirred for 19 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (10 g, hexane/ethyl acetate=1/1). Thus, N-[5-methyl-2-(1-piperidinyl)phenyl]isonicotinamide (GIF-0342) (69.5 mg, 28.8%) was yielded as a colorless solid.

The melting point, and results of TLC and $^1$H NMR (CDCl$_3$, 400 MHz), are as follows: m.p. 142-144° C.; TLC $R_f$ 0.35 (hexane/ethyl acetate=1/1); $^1$H NMR (CDCl$_3$, 400 MHz) δ 1.62-1.70 (m, 2H, CH$_2$), 1.75 (tt, 4H, J=4.9, 4.9 Hz, 2CH$_2$), 2.37 (s, 3H, 4.9 Hz, 2CH$_2$), 6.94 (dd, 1H, J=1.6, 8.1 Hz, aromatic), 7.12 (d, 1H, J=8.1 Hz, aromatic), 7.76 (dd, 2H, J=1.3, 4.5 Hz, aromatic), 8.38 (d, 1H, J=1.6 Hz, aromatic), 8.84 (dd, 2H, J=1.3, 4.5 Hz, aromatic), 9.75 (s, 1H, NH).

Referential Example 17

Synthesis of Code Name GIF-0348

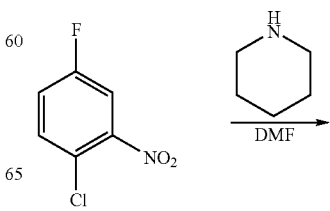

-continued

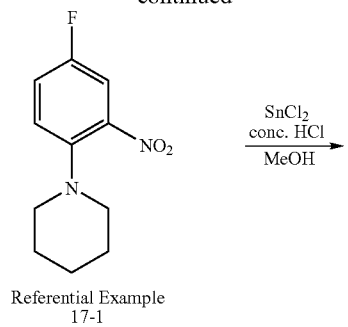

Referential Example 17-1

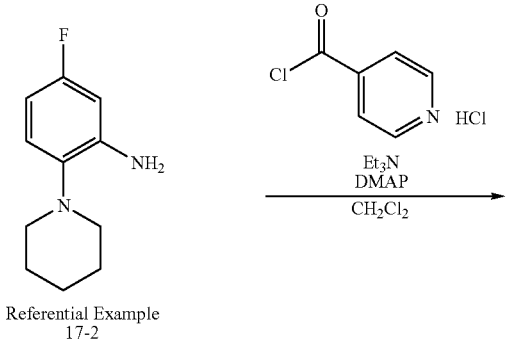

Referential Example 17-2

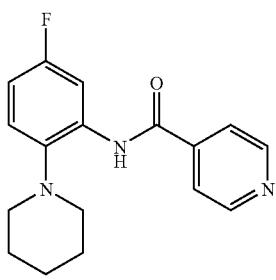

Referential Example 17-3
GIF-0348

Referential Example 17-1

Piperidine (320 μl, 3.23 mmol, commercially available product) was added at room temperature to an N,N-dimethylformamide (DMF; 0.5 ml) solution of 1,4-difluoro-2-nitrobenzene (225 mg, 1.41 mmol, commercially available product). The resulting mixture was stirred for two hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=12/1). Thus, 1-(4-fluoro-2-nitrophenyl)piperidine (298 mg, 94.2%) was yielded as an orange-colored oily material.

TLC $R_f$ 0.46 (hexane/ethyl acetate=12/1).

Referential Example 17-2

Concentrated hydrochloric acid (1.20 ml, 14.4 mmol) and anhydrous tin dichloride (1.22 g, 6.43 mmol) were sequentially added at 0° C. to a methanol (5 ml) solution of 1-(4-fluoro-2-nitrophenyl)piperidine (289 mg, 1.28 mmol), obtained as described in Referential Example 17-1. The resulting mixture was warmed to room temperature and stirred for 21 hours. A saturated aqueous solution of sodium bicarbonate was added to the mixture. The mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (25 g, hexane/ethyl acetate=12/1). Thus, 5-fluoro-2-(1-piperidinyl)aniline (250 mg, quant.) was yielded as a colorless oily material.

TLC $R_f$ 0.34 (hexane/ethyl acetate=16/1)

Referential Example 17-3

Isonicotinoyl chloride hydrochloride (454 mg, 2.55 mmol, commercially available product) and triethylamine (385 μl, 3.83 mmol) were sequentially added at 0° C. to a dichloromethane (10 ml) solution of 5-fluoro-2-(1-piperidinyl)aniline (248 mg, 1.27 mmol), obtained as described in Referential Example 17-2. The resulting mixture was warmed to room temperature and stirred for 17 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (15 g, hexane/ethyl acetate=1.5/1). Thus, N-[5-fluoro-2-(1-piperidinyl)phenyl]isonicotinamide (GIF-0348) (257 mg, 67.6%) was yielded as a colorless solid.

The melting point, and results of TLC and $^1$H NMR (CDCl$_3$, 400 MHz), are as follows: m.p. 115-116° C.; TLC $R_f$ 0.40 (hexane/ethyl acetate=1/1); $^1$H NMR (CDCl$_3$, 400 MHz) δ 1.62-1.69 (m, 2H, CH$_2$), 1.76 (bs, 4H, 2CH$_2$), 2.82 (bs, 4H, 2CH$_2$), 6.81 (ddd, 1H, J=2.8, 8.8, 10.8 Hz, aromatic), 7.18 (dd, 1H, J=5.6, 8.8 Hz, aromatic), 7.75 (dd, 2H, J=2.0, 4.4 Hz, aromatic), 8.34 (dd, 1H, J=2.8, 10.8 Hz, aromatic), 9.16 (dd, 2H, J=2.0, 4.4 Hz, aromatic), 9.83 (s, 1H, NH).

Referential Example 18

Synthesis of Code Name GIF-0349

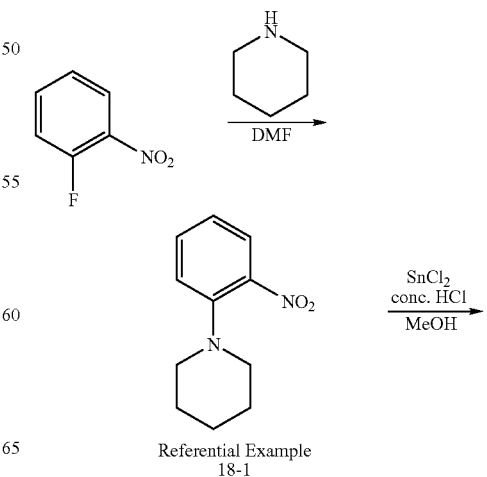

Referential Example 18-1

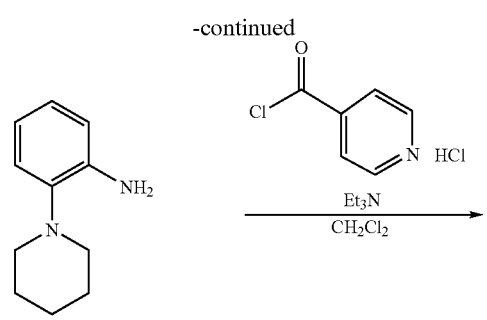

Referential Example 18-2

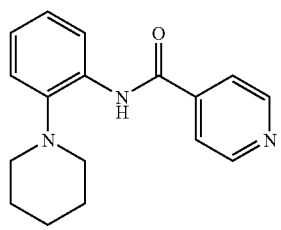

Referential Example 18-3

GIF-0349

5.73 mmol) were sequentially added at 0° C. to a dichloromethane (5 ml) solution of 2-(1-piperidinyl)aniline (203 mg, 1.15 mmol), obtained as described in Referential Example 18-2. The resulting mixture was warmed to room temperature and stirred for two hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=1/1). Thus, N-[2-(1-piperidinyl)phenyl]isonicotinamide (GIF-0349) (259 mg, 80.0%) was yielded as a colorless solid.

The melting point, and results of TLC and $^1$H NMR (CDCl$_3$, 400 MHz), are as follows: m.p. 111-113° C.; TLC R$_f$ 0.35 (hexane/ethyl acetate=1/1); $^1$H NMR (CDCl$_3$, 400 MHz) δ 1.62-1.67 (m, 2H, CH$_2$), 1.76 (tt, 4H, J=4.8, 4.8 Hz, 2CH$_2$), 2.85 (t, 4H, J=4.8 Hz, 2CH$_2$), 7.13 (td, 1H, J=1.6, 7.8 Hz, aromatic), 7.21 (td, 1H, J=1.6, 7.8 Hz, aromatic), 7.24 (dd, 1H, J=1.6, 7.8 Hz, aromatic), 7.77 (dd, 2H, J=1.9, 4.4 Hz, aromatic), 8.53 (dd, 1H, J=1.6, 7.8 Hz, aromatic), 8.84 (dd, 2H, J=1.9, 4.4 Hz, aromatic), 9.71 (s, 1H, NH).

Referential Example 19

Synthesis of Code Name GIF-0619

Referential Example 18-1

Piperidine (338 μl, 3.41 mmol, commercially available product) was added at room temperature to an N,N-dimethylformamide (DMF; 0.5 ml) solution of 2-fluoro-1-nitrobenzene (219 mg, 1.55 mmol, commercially available product). The resulting mixture was stirred for two hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=20/1). Thus, 1-(2-nitrophenyl)piperidine (315 mg, 98.8%) was yielded as a colorless oily material.

TLC R$_f$ 0.53 (hexane/ethyl acetate=16/1).

Referential Example 18-2

Concentrated hydrochloric acid (1.50 ml, 18.0 mmol) and anhydrous tin dichloride (1.45 g, 7.64 mmol) were sequentially added at 0° C. to a methanol (10 ml) solution of 1-(2-nitrophenyl)piperidine (315 mg, 1.52 mmol) obtained as described in Referential Example 18-1. The resulting mixture was warmed to room temperature and stirred for 17 hours. A saturated aqueous solution of sodium bicarbonate was added to the mixture. The resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=15/1). Thus, 2-(1-piperidinyl)aniline (238 mg, 88.8%) was yielded as a pale yellow oily material.

TLC R$_f$ 0.19 (hexane/ethyl acetate=18/1)

Referential Example 18-3

Isonicotinoyl chloride hydrochloride (616 mg, 3.46 mmol, commercially available product) and triethylamine (800 μl,

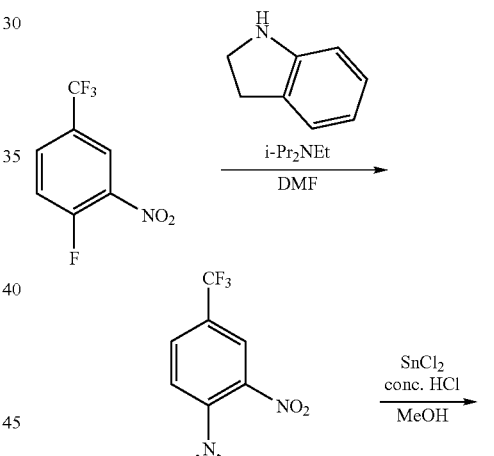

Referential Example 19-1

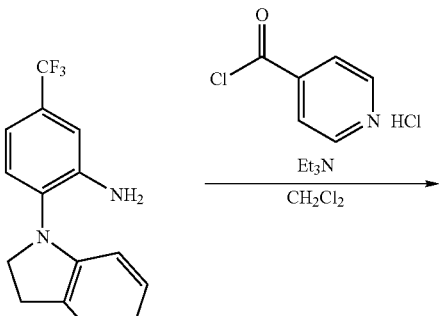

Referential Example 19-2

-continued

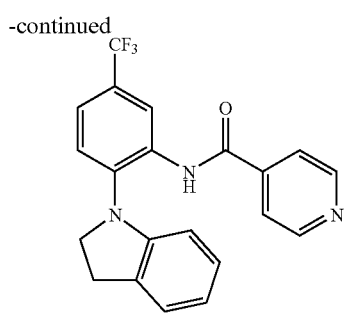

GIF-0619
Referential Example 19-3

Referential Example 19-1

Indoline (402 μl, 3.59 mmol, commercially available product) and N,N-diisopropylethylamine (619 μl, 3.59 mmol) were sequentially added at 0° C. to a N,N-dimethylformamide (DMF; 2 ml) solution of 1-fluoro-2-nitro-4-(trifluoromethyl)benzene (498 mg, 2.38 mmol, commercially available product). The resulting mixture was warmed to room temperature and stirred for one hour. The mixture was then heated at 70° C. for 5.5 hours with stirring. The mixture was cooled to room temperature. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=20/1). Thus, 1-(2-nitro-4-(trifluoromethyl)phenyl)indoline (730 mg, 99.4%) was yielded as a deep red oily material.

TLC $R_f$ 0.48 (hexane/ethyl acetate=6/1).

Referential Example 19-2

Concentrated hydrochloric acid (1.28 ml, 15.4 mmol) and anhydrous tin dichloride (1.57 g, 8.30 mmol) were sequentially added at 0° C. to a methanol (7 ml) solution of 1-(2-nitro-4-(trifluoromethyl)phenyl)indoline (730 mg, 2.37 mmol), obtained as described in Referential Example 19-1. The resulting mixture was warmed to room temperature, and stirred for eight hours. A saturated aqueous solution of sodium bicarbonate was added to the mixture. The resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=10/1). Thus, 1-[2-amino-4-(trifluoromethyl)phenyl]indoline (619 mg, 93.9%) was yielded as a red-orange colored oily material.

TLC $R_f$ 0.27 (hexane/ethyl acetate=6/1).

Referential Example 19-3

Isonicotinoyl chloride hydrochloride (669 mg, 3.76 mmol, commercially available product) and triethylamine (773 μl, 5.58 mmol) were sequentially added at 0° C. to a dichloromethane (5 ml) solution of 1-[2-amino-4-(trifluoromethyl)phenyl]indoline (518 mg, 1.86 mmol), obtained as described in Referential Example 19-2. The resulting mixture was warmed to room temperature and stirred for 2.5 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (50 g, hexane/ethyl acetate=1/1). Thus, N-[2-(1-indolinyl)-5-(trifluoromethyl)phenyl]isonicotinamide (GIF-0619) (643 mg, 90.1%) was yielded as a colorless solid.

TLC $R_f$ 0.32 (hexane/ethyl acetate=1/1).

Referential Example 20

Synthesis of Code Name GIF-0620

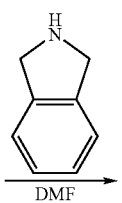

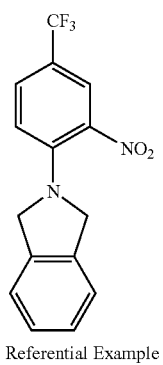

Referential Example 20-1

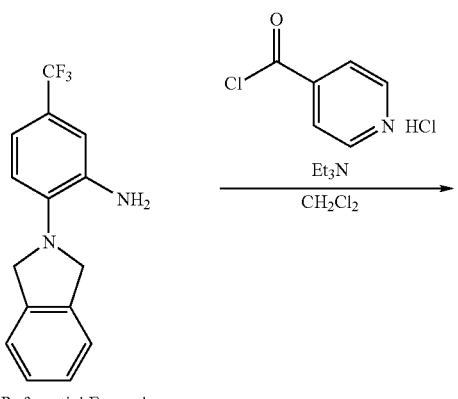

Referential Example 20-2

-continued

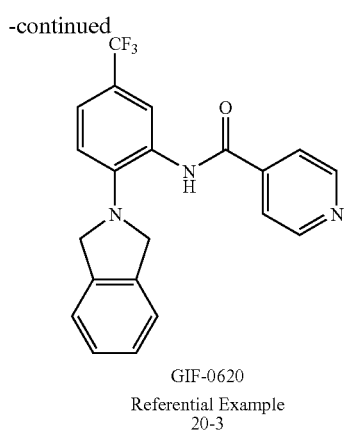

GIF-0620
Referential Example
20-3

Referential Example 20-1

Isoindoline (679 μl, 5.98 mmol, commercially available product) was added at 0° C. to an N,N-dimethylformamide (DMF; 2 ml) solution of 1-fluoro-2-nitro-4-(trifluoromethyl)benzene (508 mg, 2.43 mmol, commercially available product). The resulting mixture was warmed to room temperature and stirred for two hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=15/1). Thus, 2-[2-nitro-4-(trifluoromethyl)phenyl]isoindoline (749 mg, quant.) was yielded as a yellow solid.

TLC $R_f$ 0.42 (hexane/ethyl acetate=10/1).

Referential Example 20-2

Concentrated hydrochloric acid (1.13 ml, 13.5 mmol) and anhydrous tin dichloride (1.38 g, 7.28 mmol) were sequentially added at 0° C. to a methanol (7 ml) solution of 2-[2-nitro-4-(trifluoromethyl)phenyl]isoindoline (641 mg, 2.08 mmol), obtained as described in Referential Example 20-1. The resulting mixture was warmed to room temperature and stirred for 8.5 hours. A saturated aqueous solution of sodium bicarbonate was added to the mixture. The resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=15/1). Thus, 2-[2-amino-4-(trifluoromethyl)phenyl]isoindoline (225 mg, 38.9%) was yielded as a red-orange colored oily material.

TLC $R_f$ 0.38 (hexane/ethyl acetate=10/1).

Referential Example 20-3

Isonicotinoyl chloride hydrochloride (250 mg, 1.40 mmol, commercially available product) and triethylamine (287 μl, 2.07 mmol) were sequentially added at 0° C. to a dichloromethane (6 ml) solution of 2-[2-amino-4-(trifluoromethyl)phenyl]isoindoline (193 mg, 0.694 mmol), obtained as described in Referential Example 20-2. The resulting mixture was warmed to room temperature and stirred for three hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (5 g, hexane/ethyl acetate=1/1). Thus, N-[2-(2-isoindolinyl)-5-(trifluoromethyl)phenyl]isonicotinamide (GIF-0620) (266 mg, quant.) was yielded as a colorless solid.

TLC $R_f$ 0.31 (hexane/ethyl acetate=1/1).

Referential Example 21

Synthesis of Code Name GIF-0621

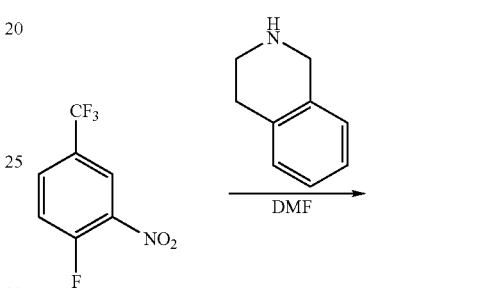

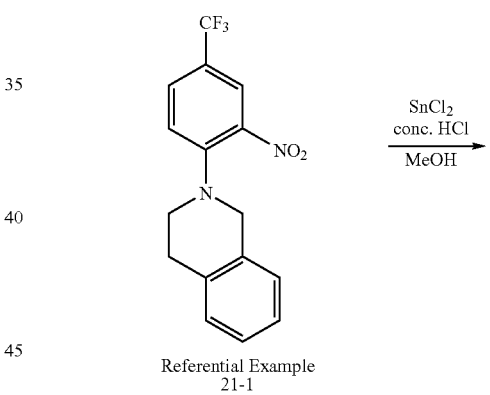

Referential Example
21-1

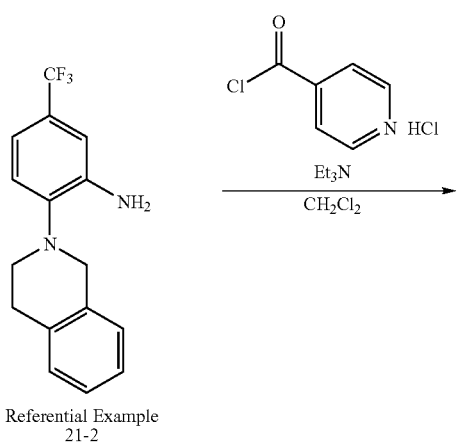

Referential Example
21-2

-continued

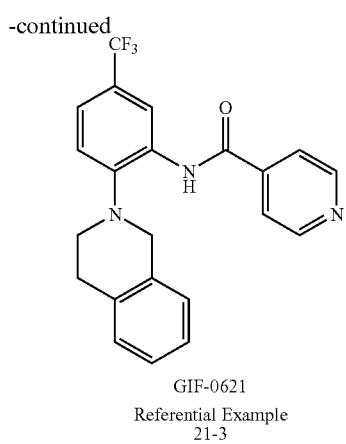

GIF-0621
Referential Example 21-3

Referential Example 21-1

1,2,3,4-tetrahydroisoquinoline (909 μl, 7.26 mmol, commercially available product) was added at 0° C. to an N,N-dimethylformamide (DMF; 4 ml) solution of 1-fluoro-2-nitro-4-(trifluoromethyl)benzene (506 g, 2.42 mmol, commercially available product). The resulting mixture was warmed to room temperature and stirred for 3.5 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=10/1). Thus, 1,2,3,4-tetrahydro-2-[2-nitro-4-(trifluoromethyl)phenyl]isoquinoline (779 mg, 99.9%) was yielded as an orange-colored solid.

TLC $R_f$ 0.54 (hexane/ethyl acetate=10/1).

Referential Example 21-2

Concentrated hydrochloric acid (1.11 ml, 13.3 mmol) and anhydrous tin dichloride (1.35 g, 7.12 mmol) were sequentially added at 0° C. to a methanol (8 ml) solution of 1,2,3,4-tetrahydro-2-[2-nitro-4-(trifluoromethyl)phenyl]isoquinoline (658 mg, 2.04 mmol), obtained as described in Referential Example 21-1. The resulting mixture was warmed to room temperature and stirred for 18 hours. A saturated aqueous solution of sodium bicarbonate was added to the mixture. The resulting mixture was extracted three times with ethyl acetate. The obtained organic layer was washed with a saturated sodium chloride solution, dried over anhydrous sodium sulfate, filtered, and concentrated under reduced pressure. The residue was purified by silica gel column chromatography (30 g, hexane/ethyl acetate=20/1). Thus, 2-[2-amino-4-(trifluoromethyl)phenyl]-1,2,3,4-tetrahydroisoquinoline (426 mg, 71.4%) was yielded as a red-orange colored oily material.

TLC $R_f$ 0.36 (hexane/ethyl acetate=10/1).

Referential Example 21-3

Isonicotinoyl chloride hydrochloride (390 mg, 2.19 mmol, commercially available product) and triethylamine (449 l, 3.24 mmol) were sequentially added at 0° C. to a dichloromethane (5 ml) solution of 2-[2-amino-4-(trifluoromethyl)phenyl]-1,2,3,4-tetrahydroisoquinoline (315 mg, 1.08 mmol), obtained as described in Referential Example 21-2. The resulting mixture was warmed to room temperature and stirred for half an hour. Water was added to the mixture, and the resulting mixture was extracted three times with dichloromethane. The obtained organic layer was washed with a saturated sodium chloride solution, dried over anhydrous sodium sulfate, filtered, and concentrated under reduced pressure. The residue was purified by silica gel column chromatography (20 g, hexane/ethyl acetate=2/1). Thus, N-[2-(1,2,3,4-tetrahydroisoquinolin-2-yl)-5-(trifluoromethyl)phenyl]isonicotinamide (GIF-0621) (418 mg, 97.6%) was yielded as a colorless solid.

TLC $R_f$ 0.52 (hexane/ethyl acetate=1/1).

Referential Example 22

Synthesis of Code Name GIF-0608

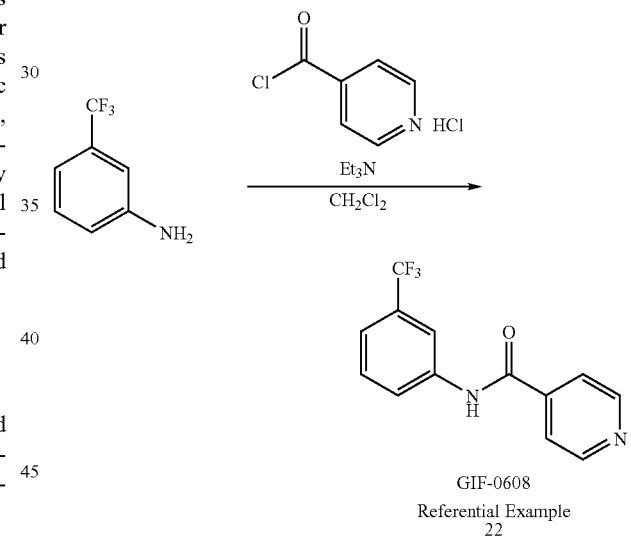

GIF-0608
Referential Example 22

Isonicotinoyl chloride hydrochloride (670 mg, 3.76 mmol, commercially available product) and triethylamine (864 μl, 6.20 mmol) were sequentially added at 0° C. to a dichloromethane (5 ml) solution of 3-(trifluoromethyl)aniline (208 mg, 1.29 mmol, commercially available product). The resulting mixture was warmed to room temperature and stirred for 23 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by recrystallization (ethyl acetate). Thus, N-[3-(trifluoromethyl)phenyl]isonicotinamide (GIF-0608) (166 mg, 48.3%) was yielded as a colorless solid.

TLC $R_f$ 0.26 (hexane/ethyl acetate=1/2).

Referential Example 23

Synthesis of Code Name GIF-0612

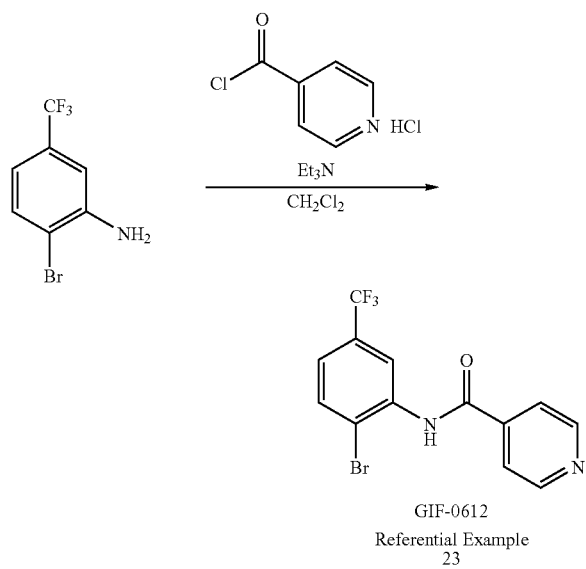

GIF-0612
Referential Example 23

Isonicotinoyl chloride hydrochloride (427 mg, 2.39 mmol, commercially available product) and triethylamine (410 µl, 2.94 mmol) were sequentially added at 0° C. to a dichloromethane (5 ml) solution of 2-bromo-5-(trifluoromethyl) aniline (480 mg, 2.00 mmol; commercially available product). The resulting mixture was warmed to room temperature and stirred for 24 hours. Water was added to the mixture, and the resulting mixture was extracted three times with ethyl acetate. The obtained organic layer was washed with a saturated sodium chloride solution, dried over anhydrous sodium sulfate, filtered, and concentrated under reduced pressure. The residue was purified by recrystallization (ethyl acetate). Thus, N-[2-bromo-5-(trifluoromethyl)phenyl]isonicotinamide (GIF-0612) (308 mg, 44.8%) was yielded as a colorless solid.

TLC $R_f$ 0.46 (hexane/ethyl acetate=1/1).

Referential Example 24

Testing the Toxicity of SRPIN-1

Chromosomal screening tests were carried out using mammalian cells to evaluate SRPIN-1 abnormalities. The mutagenicity of SRPIN-1 was evaluated using Chinese hamster CHL cells (Dainippon Pharma Co., Ltd) and with the inducibility of chromosome abnormality as an indicator. The tests used the metabolic activation method (+S9 mix) with a short treatment (six hours of treatment, 18 hours of restoration), and, in the absence of a metabolic activation system, used a continuous treatment method (24 hours of treatment). CHL cells were cultured in MEM Earle (GIBCO BRL) containing 10% fetal calf serum (ICN Flow) under 5% $CO_2$ at 37° C. Assays by the metabolic activation method used S9 fraction (Oriental Yeast Co Ltd.; A. T. Natarajan et al., Mutation Res., 37, pp 83-90 (1976)), which had been prepared from the liver of Sprague-Dawley rats (male, 7 weeks old; Charles River Laboratories Japan, Inc) to which phenobarbital was administered intraperitoneally once a day for four consecutive days (30 mg/kg in the first administration, and 60 mg/kg in the second to fourth administrations) and at the third administration, 5,6-benzoflavone was given intraperitoneally at a dose of 80 mg/kg. 1 ml of the S9 mix used in this assay contained 4 µmol of HEPES buffer (pH 7.4), 5 µmol of $MgCl_2$, 33 µmol of KCl, 5 µmol of G6P, 4 µmol of NADP, and 0.3 ml of S9 fraction.

In the short treatment method, CHL cells (about $4 \times 10^3$ cells/ml) were cultured in 5 ml of culture medium using a 60 mm dish. After three days of culture, a 1.33 ml aliquot of culture medium was taken from the dish, 0.83 ml of S9 mix was added thereto, and 0.5 ml of test solution was immediately added at various concentrations (final concentrations: 5, 1.58, or 0.5 mg/ml; dissolved in an aqueous solution of 0.5% carboxymethylcellulose sodium (CMC—Na)). The cells were incubated for six hours, and then washed with PBS. 5 ml of fresh culture medium was added to replace the culture medium. The cells were further cultured for 18 hours. An aqueous solution (0.5 ml) of 0.5% CMC—Na was used as a negative control, while dimethylnitrosamine (DMN; a final concentration of 500 µg/ml) was used as a positive control; the procedure used was the same as described above. In the method with continuous treatment, CHL cells (about $4 \times 10^3$ cells/ml) were cultured in 5 ml of culture medium in a 60 mm dish. After three days of culture, 0.5 ml of the culture medium was taken from the dish. 0.5 ml of test solutions at various concentrations (final concentrations: 5, 1.58, or 0.5 mg/ml) were added. The cells were incubated for 24 hours (about 1.5 cell cycles) without further treatment. An aqueous solution (0.5 ml) of 0.5% CMC—Na was used as a negative control, while mitomycin C (MMC; a final concentration 0.05 µg/ml) was used as a positive control; the procedure used was the same as described above.

0.1 ml of 10 µg/ml colcemide was added two hours before the culture was terminated, and the cells were harvested by treatment with a 0.25% trypsin solution. After hypotonic treatment using a 0.075 M potassium chloride solution, the cells were fixed with a mixed solution of methanol and acetic acid (3:1). The cells were dried, and then Giemsa-stained. For each dose, 50 metaphasic cells were spread out for observation and the type and frequency of structural and numerical chromosomal abnormalities was determined. Structural abnormalities were categorized into: chromatid breakage (ctb), chromatid exchange (cte), chromosome breakage (csb), chromosome exchange (cse), and miscellaneous (five or more abnormalities, fragmentations, pulverizations, and such). The frequency of occurrence was recorded for each category of abnormality. If a cell had at least one of these abnormalities, it was regarded as abnormal. When the frequency of cell abnormality was less than 5%, the testing substance was judged to be negative; when the frequency was 5% or higher and less than 10%, the testing substance was judged to be pseudo-positive; and when the frequency was 10% or higher, the substance was judged to be positive. When the frequency of occurrence of cells with abnormal chromosomes was found to be 10% or higher in a group treated with a test substance, the test substance was concluded to be a substance that induced chromosome abnormalities. In the positive control groups, where the cells were treated with 500 µg/ml DMN and 0.5 µg/ml MMC, the frequency of occurrence of cells with chromosomal abnormalities was 26 (52.0%) and 24 cells (48.0%) respectively. No abnormalities were found in the negative control. Thus, these tests were judged to be appropriately performed.

The test results for the SRPIN-1-treated groups showed that SRPIN-1 was negative for the increase in the number of cells with both structural and numerical chromosomal abnormalities when evaluated by both the short and continuous treatment methods. Based on the above results, it was concluded that the compound did not have the ability to induce chromosomal abnormalities in mammalian culture cells under the experimental conditions of the present invention.

Referential Example 25

In vivo Administration of SRPIN-1

The toxicity of SRPIN-1 was tested by single-dose oral administration to rats. SRPIN-1 was orally administered at a dose of 125, 250, 500, 1000, or 2000 mg/kg (in a volume of 10 ml per kg) to Slc:SD rats (five weeks old; Japan SLC, Inc.) whose weight gain and general conditions were normal during the acclimatization period. Each group included two males and two females. The animals were fasted from the evening of the day before administration until about four hours after administration. None of the male and female rats died, and no changes were detectable in their general condition for two days after administration. Then, SRPIN-1 was likewise orally administered at a dose of 2000 mg/kg to five male and five female Slc:SD rats (five weeks old). The rats were observed for 14 days after administration, and based on visual examinations any toxic symptoms were recorded along with their severity and timing, the time required for restoration, and the death date. The results showed that none of the male and female rats died, and no abnormalities were detectable in their general condition.

Example 1A

Phosphorylation of SR Proteins in Cells Infected with HIV

3 µg of HIVpNL4-3 genome (Adachi, A. et al., 1986, J. Virol. 59:284-289) was introduced into human Flp-In-293 cells derived from fetal kidney (R750-07; purchased from Invitrogen) using 9 µl of Genejuice (70967-4; purchased from Novagen), a gene transfer reagent. After four days the cells were lysed with 1 ml of SDS-PAGE sample buffer, and heat-denatured at 95° C. for three minutes. The lysate was immediately transferred onto ice and used as a protein sample.

The protein sample was analyzed using Western blotting. The sample was fractionated by SDS-PAGE using Laemmli buffer and gel with a gradient of 4% to 20% at 40 mA for 45 minutes. Molecular weights were determined using Broad Range Pre-stained Marker (02525-35; Nacalai) as a molecular weight marker. Then, the sample was transferred onto PROTRAN Nitrocellulose Membrane (BA85; purchased from Schleicher & Schuell BioScience) by semi-dry blotting using TransBlot SD Cell (170-3940; purchased from Bio-Rad) at 160 mA for 60 minutes. After blotting, the membrane was washed with TBS for five minutes with shaking. Then, the membrane was blocked with BlockingOne (03953-95; purchased from Nacalai) at room temperature for one hour. The membrane was washed again with TBS, and incubated at 4° C. overnight with mouse monoclonal antibody 104 (Mab104; hybridoma was purchased from ATCC), mouse anti-SC35 antibody (S4045; purchased from BDTransduction), and mouse anti-SF2 monoclonal antibody (AK103: a gift from Dr. Adrian Kramer; Hanamura, A. et al., 1998, RNA 4:430-444; Kojima, T. et al., 2001, J. Biol. Chem. 276:32247-56), which each recognize phosphorylated SR proteins and were diluted with TBS.

The membrane was washed three times with TBS at room temperature for ten minutes with shaking. Then, HRP-labeled sheep anti-mouse IgG antibody (NA9310; purchased from Amersham) was diluted with TBS, and the membrane was incubated with this secondary antibody at room temperature for one hour. The membrane was washed three times with TBS at room temperature for ten minutes with shaking. Then, the detection was carried out by chemical luminescence using ECL Detection Reagents (RPN2105; purchased from Amersham) and images were photographed using a LAS1000CCD camera (LAS1000; Fuji Film). The results are shown in FIG. 1A.

The results showed that when the cells were infected with HIVpNL4-3, Western analysis using Mab104, SC35, and SF2 antibodies could not detect any signals. Thus, it was revealed that not only was SR protein dephosphorylated, but endogenous SR proteins, such as SC35 and SF2 were also degraded.

Example 1B

Degradation of SR Proteins

Figure 1B:
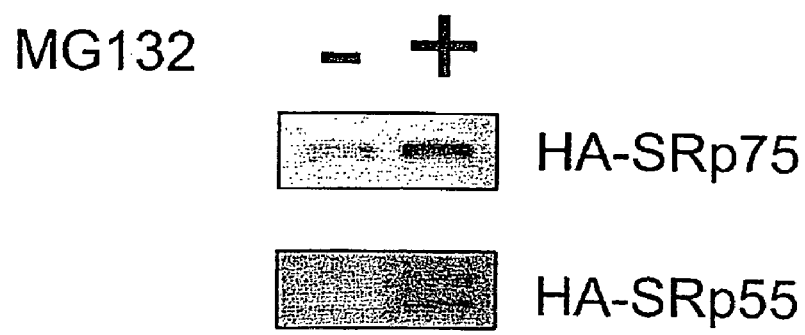
FIG. 1B: Degradation of SR protein. Plasmids for the SRp75, SRp55, and SRp40 genes were fused with Ha tag and introduced into Flp-In-293 cells. MG132 (474790; purchased from CALBIOCHEM) was added to the cells at a final concentration of 10 µM. The cells were lysed and heat-denatured. The resulting protein sample was separated by SDS-PAGE, followed by Western analysis using a rabbit anti-HA antibody as the primary antibody and a donkey anti-rabbit IgG antibody as the secondary antibody.

Using Genejuice, 1 µg each of the plasmids for the SRp75, SRp55, and SRp40 genes fused with HA tag (HA-SRp75, HA-SRp55, and HA-SRp40; gifts from Dr. Woan-Yuh TARN), were introduced into Flp-In-293 cells derived from human fetal kidney. After 36 hours, MG132 (474790; purchased from Calbiochem), a ubiquitin proteasome inhibitor, was added at a final concentration of 10 µM. After ten hours, the cells were lysed with SDS-PAGE sample buffer and heat-denatured. The resulting lysate was used as a protein sample. Using the same procedures as described above, the sample was fractionated by SDS-PAGE, and analyzed by Western blotting using a rabbit anti-HA antibody (H1803; purchased from Santa Cruz) as a primary antibody and a donkey anti-rabbit IgG antibody (NA9340; purchased from Amersham) as a secondary antibody. The results are shown in FIG. 1B.

The cells treated with MG132 gave a stronger signal than the control, showing that MG132 inhibited degradation of SR75, SR55, and SR40 proteins. In addition, similar results were obtained for other SR proteins (data not shown). Using MG132, it thus was revealed that SR proteins were degraded by ubiquitin proteasome.

Example 2A

Phosphorylation of SR Proteins in Cells Stably Expressing SRPK2

A single copy of the mouse SRPK2 gene was introduced into Flp-In-293 cells at the Flp-In site to establish multiple cell lines stably expressing SRPK2. The parent cell line Flp-In-293 was used as a mock in the analysis, and for use in the experiments SRPK2-2 was selected from the multiple established cell lines stably expressing SRPK2. pNL4-3 was introduced into these two cells. After four days, the dynamics of endogenous SR protein during HIV infection were investigated using Western analysis.

Western analysis was carried out the same way as in FIG. 1A. When the HIVpNL4-3 genome was introduced into SRPK2-2 cells, Mab104 antibody detected signals at positions corresponding to SRp35, SRp40, SRp55, and SRp75. The SR domains recognizable by Mab104 were found to be phosphorylated.

Figure 2A:
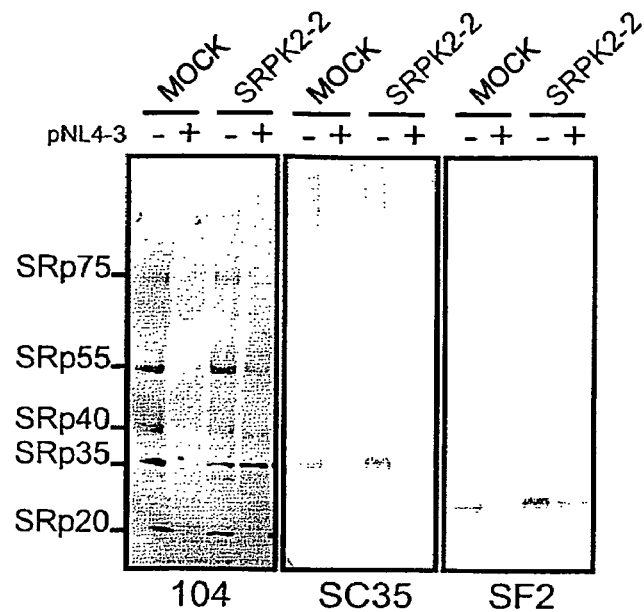
FIG. 2A: Phosphorylation of SR protein in cells stably expressing SRPK2. Mouse SRPK2 gene was introduced into Flp-In-293 cells to prepare cells stably expressing SRPK2 (SRPK2-2). pNL4-3 was introduced into these SRPK2-2 cells and cells of the parent cell line Flp-In-293 (mock). After four days, the kinetics of endogenous SR protein during HIV infection was evaluated by Western analysis in the same way as in FIG. 1A.

Furthermore, Western analysis using SC35 and SF2 antibodies revealed that SC35 and SF2 signals were observed in SRPK2-2 cells introduced with the HIVpNL4-3 genome. The results are shown in FIG. 2A.

These results showed that SR proteins are generally degraded upon HIV infection, but in cells stably expressing SRPK2, the SR proteins remain phosphorylated and are stabilized as a result. This suggests that SR protein is phosphorylated and that protein degradation via ubiquitin proteasome does not take place in cells stably expressing SRPK2.

Example 2B

Existence of SR Proteins in Cells Stably Expressing SRPK2

Figure 2B:
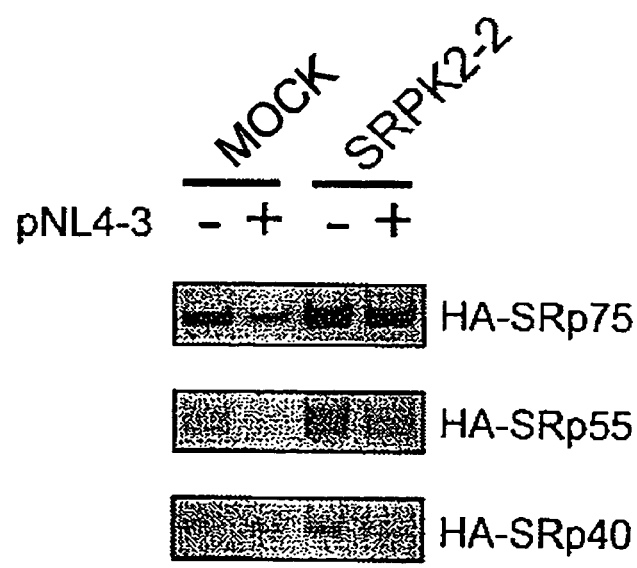
FIG. 2B: Existence of SR protein in cells stably expressing SRPK2. The HIVpNL4-3 genome and plasmids for SRp75, SRp55, and SRp40 genes fused with HA tag were introduced into mock and SRPK2-2 cells, prepared as in FIG. 2A. The samples were harvested after 36 hours and analyzed by Western blotting.

1 μg of HIVpNL4-3 genome and 1 μg each of the plasmids for the SRp75, SRp55, and SRp40 genes fused with HA tag (HA-SRp75, HA-SRp55, HA-SRp40; gifts from Dr. Woan-Yuh TARN) were introduced into the Flp-In-293 cells stably expressing SRPK2, where one copy of the SRPK2 gene had been introduced at the Flp-In site (SRPK2-2 cells) and the parental cell line Flp-In-293 (mock) using Genejuice. The samples were collected after 36 hours and analyzed by Western blotting. The results are shown in FIG. 2B. According to these results, upon HIV infection of the Flp-In-293 cells, the anti-HA antibody signal weakened or disappeared for not only SC35 and SF2, but also for SRp75, SRp55, and SRp40. In the SRPK2-2 cells, the signals for SRp75, SRp55, and SRp40 as well as SC35 and SF2 were detectable, although impaired as compared with the control.

These results suggest that SR protein degradation is enhanced upon HIV infection, but that SR protein phosphorylation in SRPK2-2 cells stabilizes the SR proteins.

Example 2C

Quantifying the Produced HIV

Figure 2C:
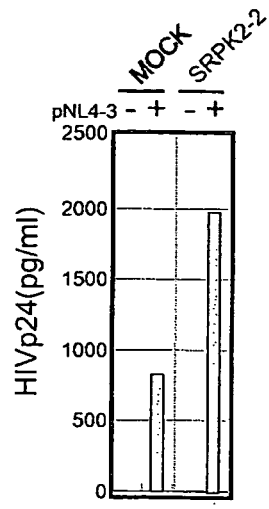
FIG. 2C: Measuring the quantity of produced HIV. The culture supernatants obtained as described in FIG. 2A were collected and the amount of produced HIV was determined.

In the experiment in Example 2A (FIG. 2A), the culture supernatant was collected and the HIV produced was quantified. After gene transfer, the culture supernatant was collected and the amount of HIV capsid protein 'p24' comprised in the culture supernatant was measured using the Lumipulse ELISA system (Fujirebio). The results are shown in FIG. 2C. These results showed that the SRPK2-2 cells produced 2.3 times more HIV than the mock culture supernatant.

These findings revealed that SR proteins are dephosphorylated in response to HIV infection, but that if the SR proteins remain phosphorylated, the regulatory mechanism of SR proteins in response to infection does not work, and thus HIV production is enhanced.

This suggests that the dephosphorylation of SR proteins functions as a host defense mechanism in response to HIV infection.

Example 3A

Evaluation of SR Proteins Contributing to In Vivo HIV Production

In the process of HIV gene expression, HIV is transcribed, processed, and translated using host-derived factors. In particular, it has been speculated that the Tat and Rev of HIV have split exons and thus an mRNA splicing reaction is essential for gene expression.

Figure 3A:
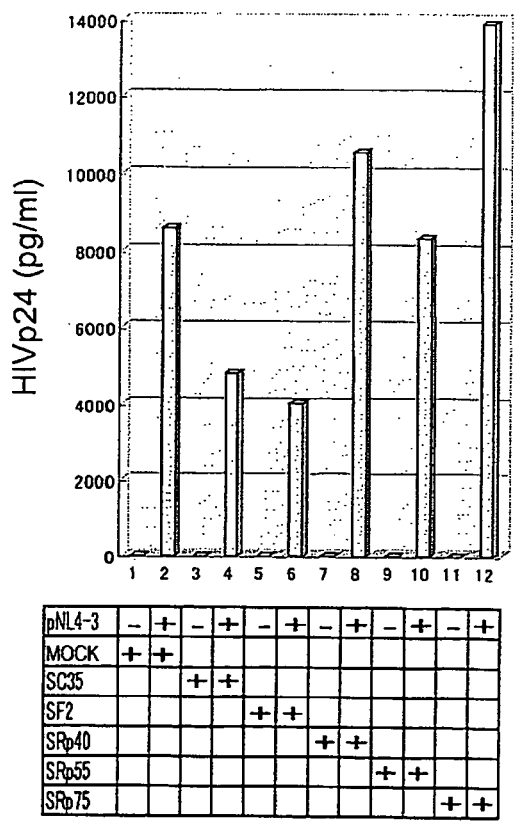
FIG. 3A: Evaluation of SR protein contributing to in-vivo HIV production. Mock plasmid, and the SC35, SF2, SRp40, SRp55, and SRp75 expression plasmids were each introduced into Flp-In293 cells. After 36 hours, culture supernatants were collected and the amount of HIVp24 were determined using the Lumipulse ELISA system.

As shown in Examples 1-2 (FIGS. 1-2), a host defense mechanism is activated upon HIV infection, and SR proteins are degraded as a result. However, there is no information about HIV's in vivo splicing reactions, nor the SR protein contribution to these reactions. In fact there are many types of SR proteins in cells, and thus expression plasmids (0.5 μg) for such SR proteins were introduced along with the HIVpNL4-3 genome (1.0 μg), and their effects were evaluated. The results are shown in FIG. 3A.

Each of the expression plasmids for mock, SC35, SF2, SRp40, SRp55, or SRp75 were introduced into Flp-In-293 cells. After 36 hours, the culture supernatants were collected and the amount of HIVp24 was determined using the Lumipulse ELISA system.

According to the results, more HIVp24 was produced for SRp40 and SRp75 than for the mock. Thus, SRp40 and SRp75 were found to have the effect of enhancing HIV production.

Example 3B

Evaluation of the Effect of Using hnRNPA1 on In vivo HIV Production

Figure 3B:
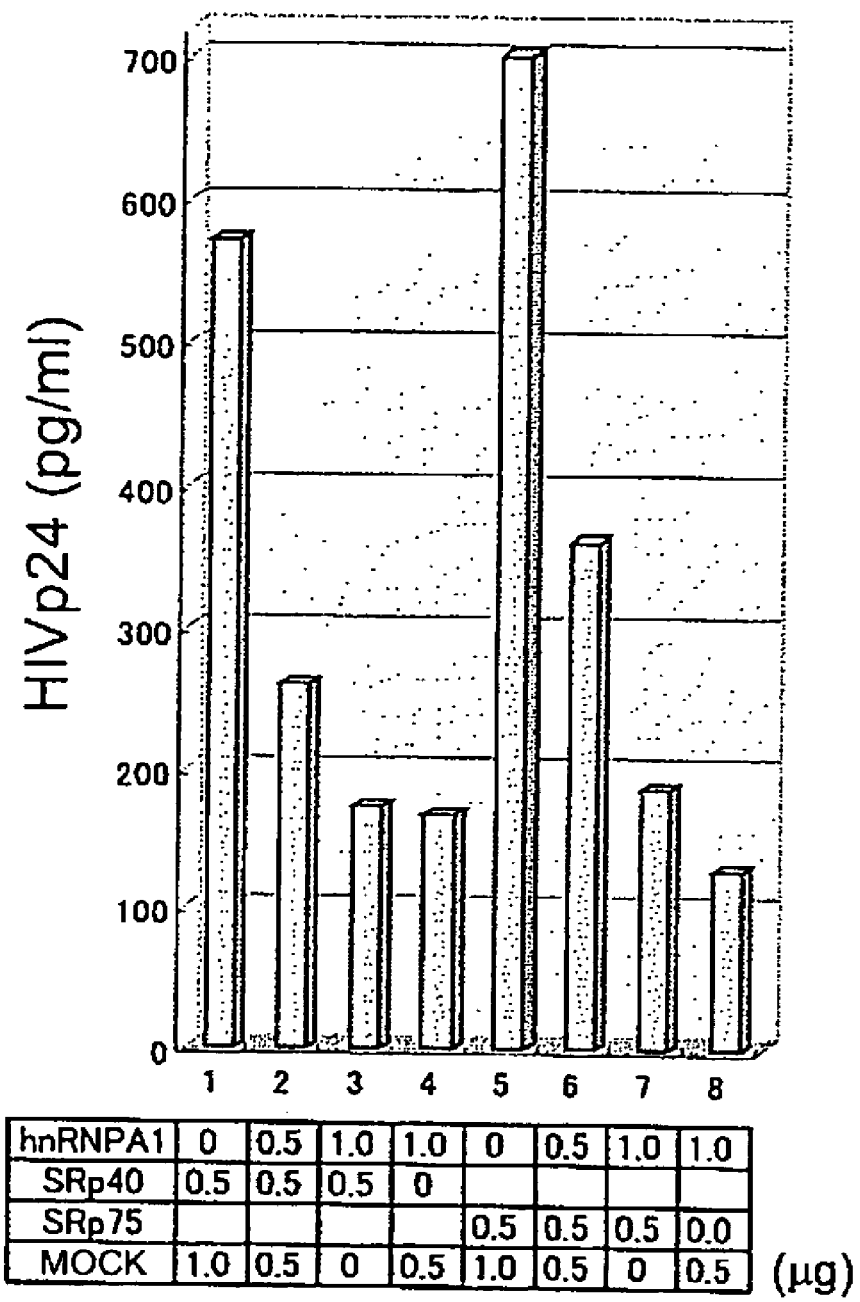
FIG. 3B: Evaluation of the effect of hnRNPA1 on in-vivo HIV production. Gene transfer into Flp-In293 cells was carried out using a fixed amount (500 ng) of an SRp40 or SRp75 expression plasmid as well as an hnRNPA1 expression plasmid, the amount of which was step increased. After 36 hours, culture supernatants were collected and the amount of HIVp24 was determined using the Lumipulse ELISA system.

As shown in FIG. 3B, in combination with HIVpNL4-3 genome (0.5 μg), a fixed amount (500 ng) of expression plasmid for SRp40 or SRp75 and increasing amounts of an expression plasmid for hnRNPA1 were introduced into Flp-In-293 cells. After 36 hours, the culture supernatant was collected and the amount of HIVp24 was determined using the Lumipulse ELISA system.

The results showed that the amount of HIVp24 determined by the Lumipulse ELISA system decreased depending on the dose of hnRNPA1. Specifically, hnRNPA1 suppresses HIV production, acting in competition with SRp40 and SRp75.

This suggests that HIV gene expression is regulated by splicing reactions in cells. Actually, since hnRNPA1 co-exists with SRp40 and SRp75 in cells, it is thought that HIV infection-induced degradation of SR proteins in cells functions as a defense mechanism by allowing hnRNPA1 to dominate in cells and thus suppressing HIV gene expression.

Example 4A

Search for SRPK Inhibitors of SR Protein Phosphorylation in Cells

Inhibitors that competitively bind to the ATP binding site shared by the kinases were sought. One hit compound in the results of screening was found to be commercially available from Maybridge (molecular weight=349.35; CAS Registry No. 218156-96-8). However, no information about the inhibition of kinase has been previously disclosed. The present inventors named the compound "SRPIN-1" (SRPk Inhibitor-1).

Example 4B

Evaluation of the Inhibition of SRPK1 Phosphorylation Activity by SRPIN-1

An RS peptide (NH2-RSPSYGRSRSRSRSRSRSRSNSRSRSY-OH; SEQ ID NO: 5) corresponding to the RS domain of SF2 was synthesized. The peptide was dissolved to a concentration of 1 mg/ml in 10 mM Tris-HCl (pH 7.5). SRPIN-1 (final concentration: 0.1, 0.3, 1.0, 3.0, or 10.0 μM) was incubated with 1 μg of purified recombinant SRPK1 protein, which had been expressed in $E.\ coli$, in a reaction buffer (250 μM MgCl$_2$, 0.25 mM ATP, 1 mCi of [γ-$^{32}$P] ATP) in a 30° C. water bath for ten minutes. The amounts of SRPK1 and RS peptide for the kinase activity assay, and the conditions for reaction time, were tested in advance and selected for reaction linearity.

Figure 4A:
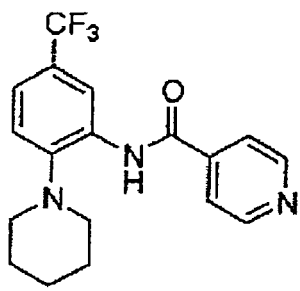
FIG. 4A: Search for SRPK inhibitors to inhibit the phosphorylation of intracellular SR protein. Structural formula of SRPIN-1 (SRPk Inhibitor-1).
Figure 4B:
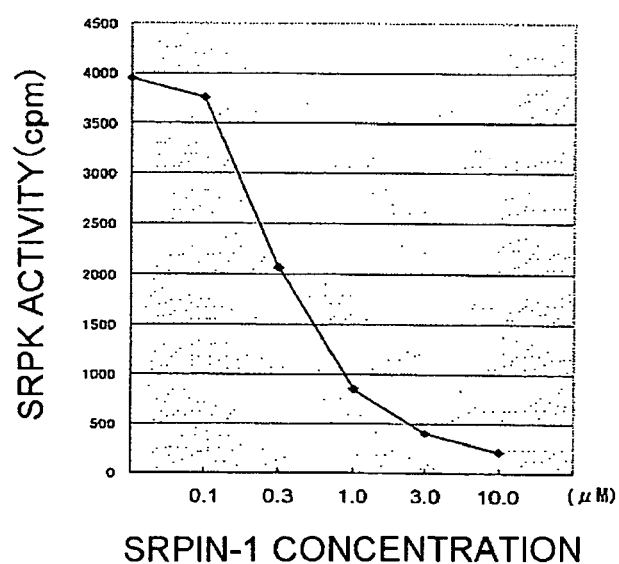
FIG. 4B: Evaluation of inhibition of the phosphorylation activity of SRPK1 by SRPIN-1. An RS peptide corresponding to RS domain of SF2 was dissolved in 10 mM Tris-HCl to a concentration of 1 mg/ml (pH 7.5). The peptide was incubated for ten minutes with 1 µg of SRPK1 protein in a reaction buffer (250 µM $MgCl_2$, 0.25 mM ATP, 1 mCi of [γ-$^{32}$P]ATP, and SRPIN-1 (final concentration: 0.1, 0.3, 1.0, 3.0, or 10.0 µM)) in a water bath at 30° C. The reaction mixture was dropped onto a P81 phosphocellulose membrane (P81; Whatman), and then the membrane was washed with a 5% phosphoric acid solution. After washing, the radioactivity of $^{32}$P on the P81 membrane was determined in a liquid scintillation counter.

SRPK1 and RS peptide were incubated together for ten minutes, then the reaction solution was dropped onto a P81 phosphocellulose membrane (P81; Whatman) and the membrane was washed with 5% phosphoric acid solution. After washing, $^{32}$P radioactivity on the P81 membrane was determined using a liquid scintillation counter. The results are shown in FIG. 4B.

The results showed that the IC50 of SRPIN-1 for SRPK1 was about 400 nM. When tested using the same technique, CLK1, CLK2, CLK3, CLK4, SRPK2, PRP4, PKA, and PKC did not exhibit an inhibitory effect, even at the final concentration of 10 μM. It is thus safe to conclude that SRPIN-1 is an SRPK1-specific inhibitor.

Example 4C

Figure 4C:
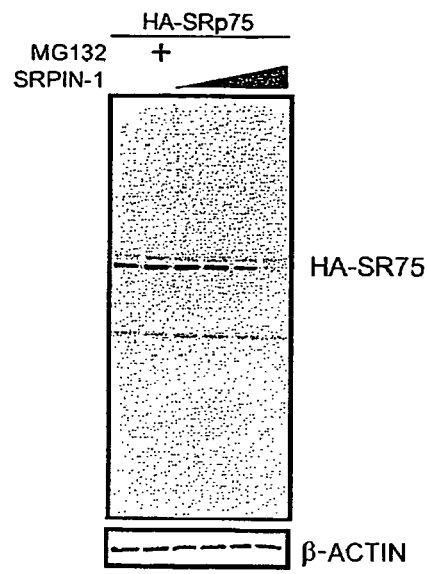
FIG. 4C: Evaluation of in-vivo inhibition of SR protein phosphorylation using SRPIN-1, and evaluation of the induction of the accompanying SR protein degradation. HA-SRp75 plasmid was introduced into Flp-In293 cells. After 36 hours, MG132 (final concentration: 10 µM) and SRPIN-1 (10, 20, or 50 µM) were added to the cells. The cells were incubated for 15 hours and then lysed. After SDS-PAGE, the samples were analyzed by Western blotting using anti-HA antibody. Western analysis was also carried out using an antibody against beta actin as a control protein amount.

Evaluation of In vivo Inhibition of SR Protein Phosphorylation by SRPIN-1 and the Accompanying Induction of SR Protein Cegradation HA-SRp75 plasmid (1.0 μg) was introduced into Flp-In-293 cells. After 36 hours, MG132 (final concentration: 10 μM) and SRPIN-1 (10, 20, or 50 μM) were added, and the cells were incubated for 15 hours. Then, the cells were lysed with SDS-PAGE sample buffer. The lysate was used as a protein sample. The sample was fractionated by SDS-PAGE and analyzed by Western blotting using the anti-HA antibody. In addition, as a control for protein amount, Western analysis was carried out using anti-beta actin antibody. The results are shown in FIG. 4C.

The result showed that the HA antibody signal weakened depending on the concentration of SRPIN-1. This suggests that the endogenous SRPK1 activity was inhibited in an SRPIN-1 dependent manner, and as a result SRp75 protein was degraded.

This finding shows that the inhibition of SRPK1 by SRPIN-1 can result in the inhibition of in vivo SR protein phosphorylation, labilizing SR protein as a result, and thus enhancing protein degradation.

Example 4D

Evaluation of the Inhibition of HIV Infection by Adding SRPIN-1

Figure 4D:
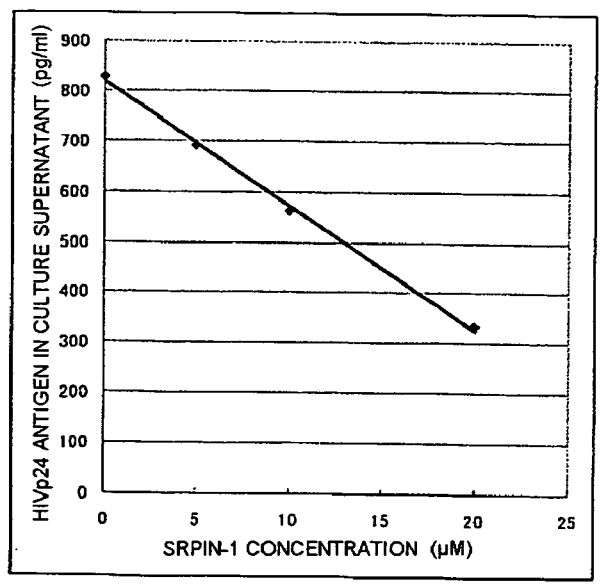
FIG. 4D: Evaluation of the inhibition of HIV infection upon addition of SRPIN-1. HIV virion was prepared using 293 T cells and then added to MT-4 cells along with SRPIN-1 (final concentration: 0.5, 10, or 20 µM). After two hours of incubation at 37° C. under 5% $CO_2$, the cells were centrifuged to change the culture medium. The culture supernatant was collected after 48 hours, and the amount of HIVp24 was determined by the Lumipulse ELISA system.

An infection experiment was carried out by adding HIV virions, which were prepared in 293T cells, to MT-4 cells. First, a prepared viral liquid and SRPIN-1 (final concentration: 0.5, 10, or 20 μM) were simultaneously added to the MT-4 cells. The cells were incubated at 37° C. under 5% CO$_2$ for two hours, then centrifuged, and the culture medium was exchanged for fresh medium. Then, the culture supernatant was collected after 48 hours, and the amount of HIVp24 was determined by the Lumipulse ELISA system. The results are shown in FIG. 4D.

The result showed that the amount of HIVp24 as determined by the Lumipulse ELISA system decreased in an SRPIN-1 concentration-dependent manner. This suggests that SRPIN-1 can inhibit HIV production in a concentration-dependent manner.

Example 5

Inhibition of SRPK1 or SRPK2 Phosphorylation Activity Using SRPIN-1 Analogs

The same procedure as described in Example 4B was used to determine whether SRPIN-1 analogs had the activity of inhibiting the phosphorylation activity of SRPK1 and SRPK2. Each SRPIN-1 analog (10 μM; in DMSO) was incubated with 1 μg of purified recombinant SRPK1 or SRPK2 protein, which was expressed in E. coli, in a reaction buffer (400 μM HEPES (pH 7.5), 100 μM MgCl$_2$, 200 μM ATP, 1 mCi [γ-$^{32}$P] ATP, and 1 mg/ml RS peptide (SEQ ID NO: 5)) in a 30° C. water bath for 20 minutes.

Figure 5A:
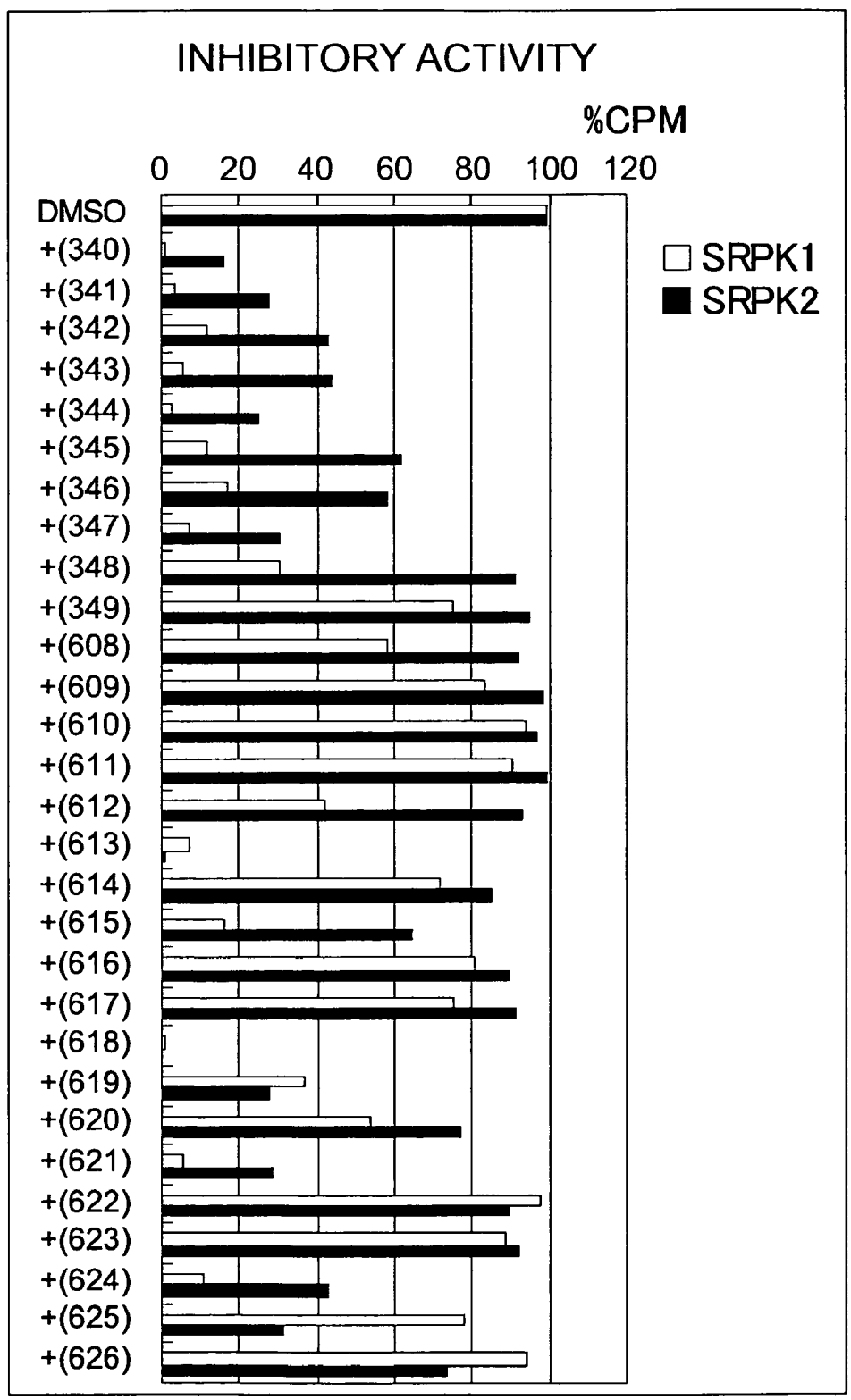
FIG. 5A: Evaluation of the SRPK-inhibiting activities of SRPIN-1 and analogs thereof. The inhibitory effects of SRPIN-1 (Compound No. 340) and analogs thereof (Compound Nos. 341 to 349, and 608 to 626) on the phosphorylation activities of SRPK1 and SRPK2 were determined.

After RS peptide was incubated with SRPK1 or SRPK2 for 20 minutes, the reaction solution was dropped onto P81 phosphocellulose membrane (P81; Whatman) and the membrane was washed three times for ten minutes with 5% phosphoric acid solution. After washing, $^{32}$P radioactivity on the P81 membrane was determined using a liquid scintillation counter. As shown in FIG. 5A, each SRPIN-1 analog exerted an inhibitory effect on the phosphorylation activity of SRPK1 and/or SRPK2. In particular, the compounds of Compound Nos. 340 (SRPIN-1) to 348, 612, 613, 615, 618, 619, 621, 624, and 625 were found to exhibit a strong inhibitory effect on SRPK1 or SRPK2.

Figure 5B:
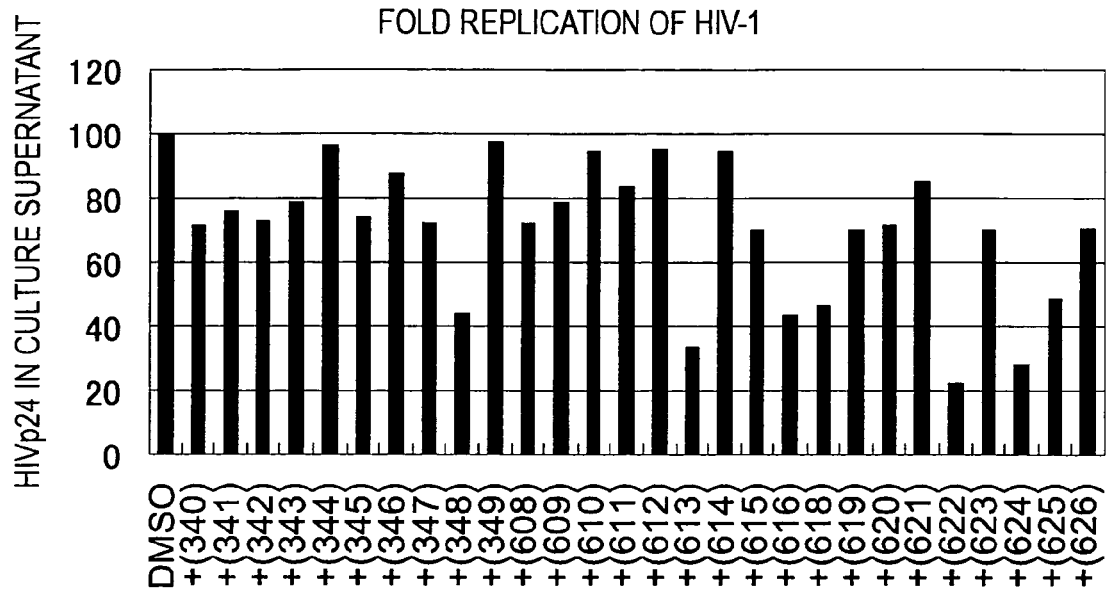
FIG. 5B: The effect of SRPIN-1 and analogs thereof in inhibiting HIV replication. This figure shows the results of assaying the effect of SRPIN-1 and analogs thereof in inhibiting HIV replication in MT-4 cells.
Figure 5C:
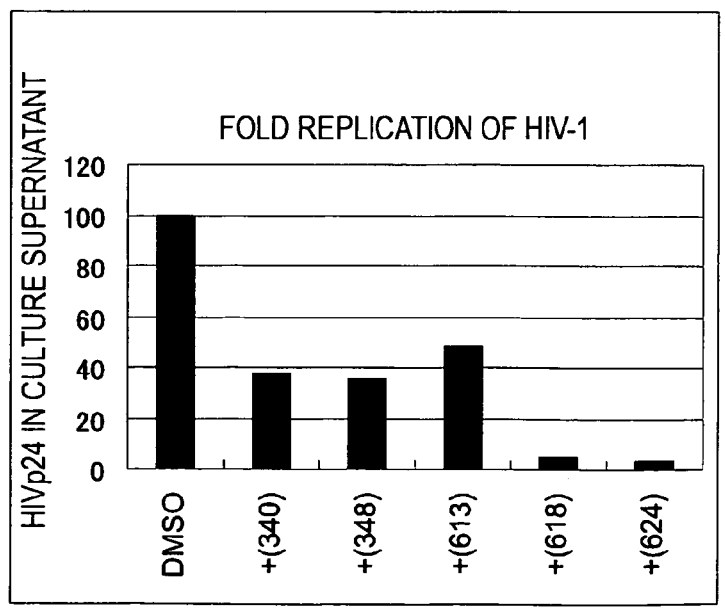
FIG. 5C: The effect of SRPIN-1 and analogs thereof in inhibiting HIV replication. Like FIG. 5B, this figure shows the results of assaying the effect of SRPIN-1 and analogs thereof in inhibiting HIV replication in Jurkat cells.

Then, each SRPIN-1 analog was tested for its effect in suppressing HIV replication. An infection experiment was carried out by adding HIV virions, which were prepared in 293T cells, to MT-4 cells (JCRB No. JCRB0135). First, a prepared viral liquid and an SRPIN-1 analog (final concentration: 5, 10, or 20 μM) were simultaneously added to the MT-4 cells. The cells were incubated at 37° C. under 5% CO$_2$ for two hours, then centrifuged, and the culture medium was exchanged for fresh medium. The culture supernatant was then collected after 48 hours, and the amount of HIVp24 was determined by the Lumipulse ELISA system. The results showed that each SRPIN-1 analog listed in FIG. 5B had the activity of inhibiting HIV replication. In particular, the compounds of Compound Nos. 340, 341, 342, 343, 345, 347, 348, 608, 613, 615, 616, 618, 619, 620, 622, 623, 624, 625, and 626 were found to have strong effects in suppressing HIV propagation. Furthermore, as shown in FIG. 5C, the compounds were also found to have the effect of suppressing HIV propagation in experiments using other cells (Jurkat).

Example 6

Suppressing Effect on Sindbis Virus Propagation

5 μl of sindbis virus (4.7×10$^7$ PFU/ml) was added to Vero cells (JCRB 0111) and the cells were cultured for 24 hours. The culture supernatant was collected as stock virus, diluted to 10$^2$ to 10$^7$ PFU, then added to BHK21 C13 cells (JCRB9020). SRPIN-1 was also added at the same time (final concentration: 5, 10, 20, or 40 μM). After one hour of infection at room temperature, a medium comprising 1% methylcellulose (SIGMA M0512-100 G) was added, and the cells were gently cultured at 37° C. under 5% CO$_2$ for 48 hours. Cell morphology was observed under a phase contrast microscope, and the number of plaques formed by cell death caused by sindbis virus infection was counted (plaque assay) to calculate the PFU/ml.

Figure 6A:
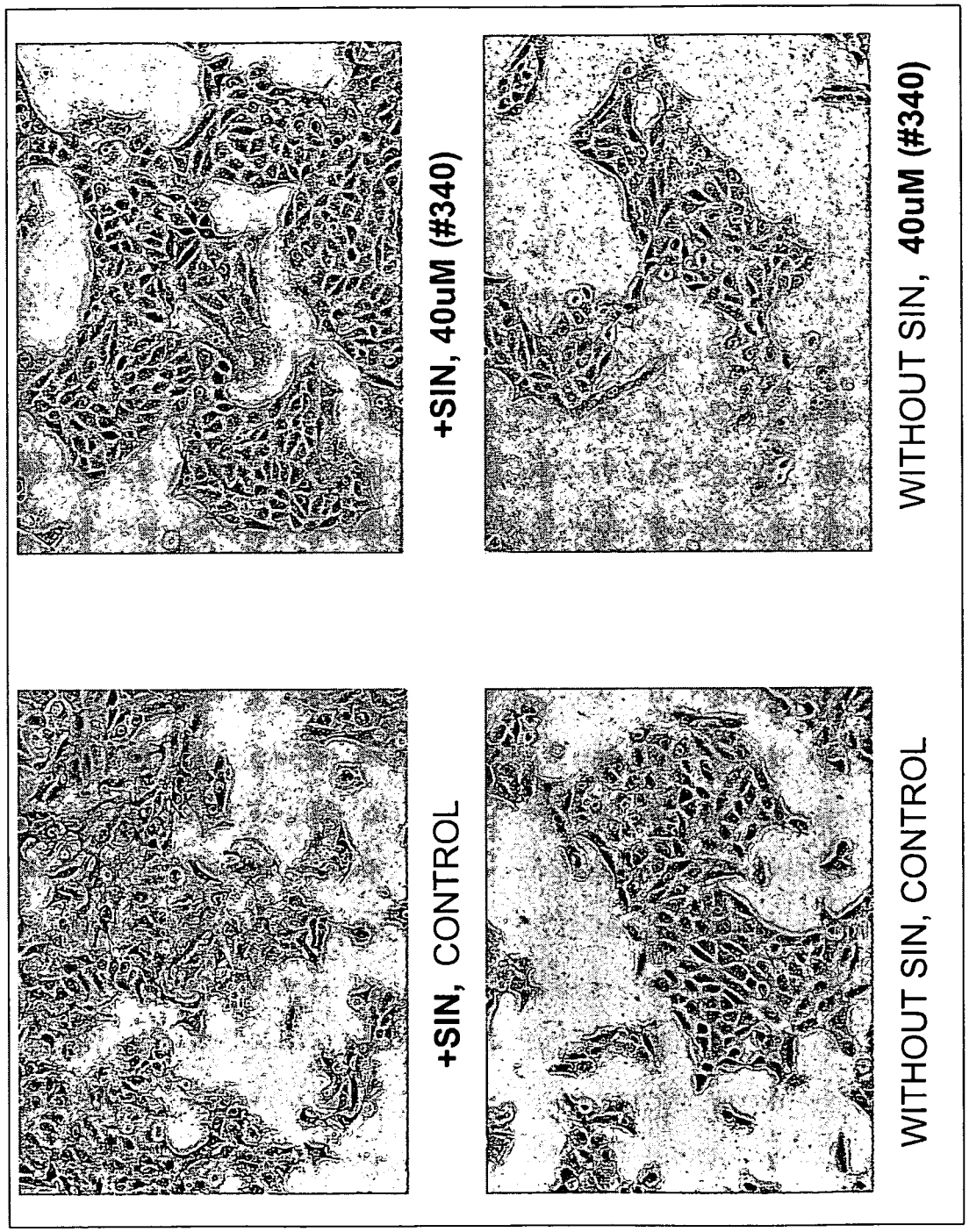
FIG. 6A: Antiviral activity of SRPIN-1 against sindbis virus. This figure shows phase contrast microscopic images of cells infected with sindbis virus. Marked cell damage caused by the propagation of sindbis virus was found in cells to which SRPIN-1 was not administered, while cell damage was dramatically inhibited by administering SRPIN-1.
Figure 6B:
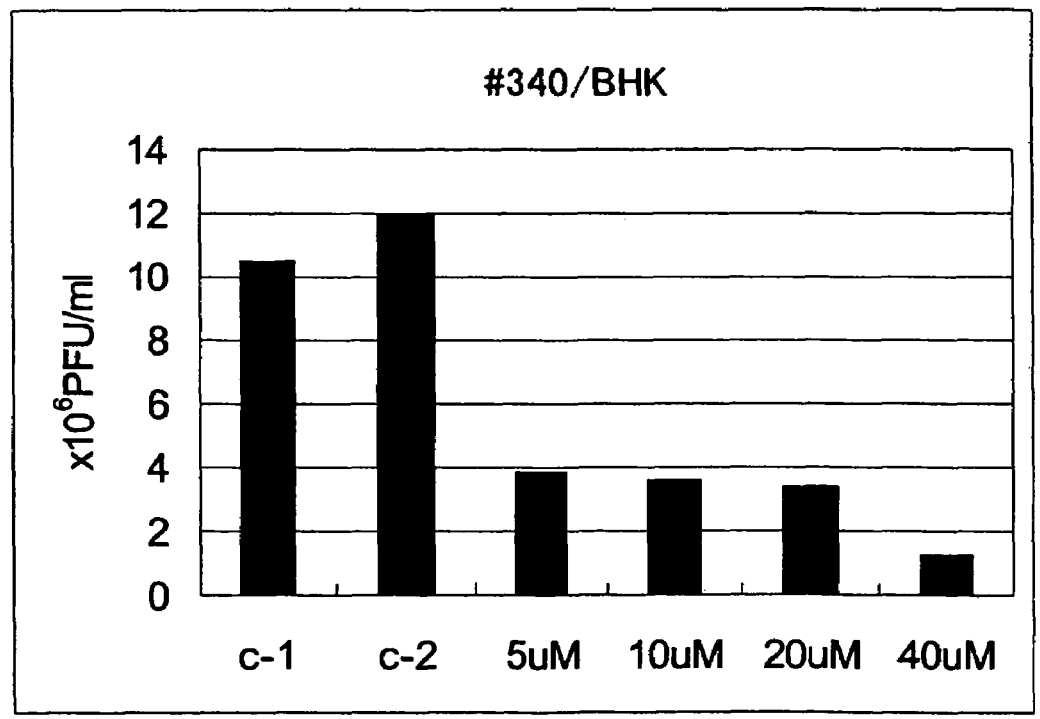
FIG. 6B: Antiviral activity of SRPIN-1 against sindbis virus. This figure shows the results of a plaque assay for sindbis virus-infected cells. SRPIN-1 significantly inhibited the propagation of Sindbis virus in a concentration-dependent manner when its concentration was 5 µM or higher.

FIG. 6A shows phase contrast microscopic images of cells 20 hours after virus infection. Marked cell damage caused by sindbis virus propagation was found in those cells not treated with SRPIN-1 ("+SIN, control" in this Figure), while cell damage was dramatically suppressed by administering SRPIN-1 (40 μM) ("+SIN,40μM (#340)" in this Figure). The plaque assay results also revealed that a 5 μM or higher concentration of SRPIN-1 significantly suppressed the propagation of sindbis virus in a concentration-dependent manner (FIG. 6B).

Example 7

Suppressing Effect on Cytomegalovirus Propagation

Figure 7:
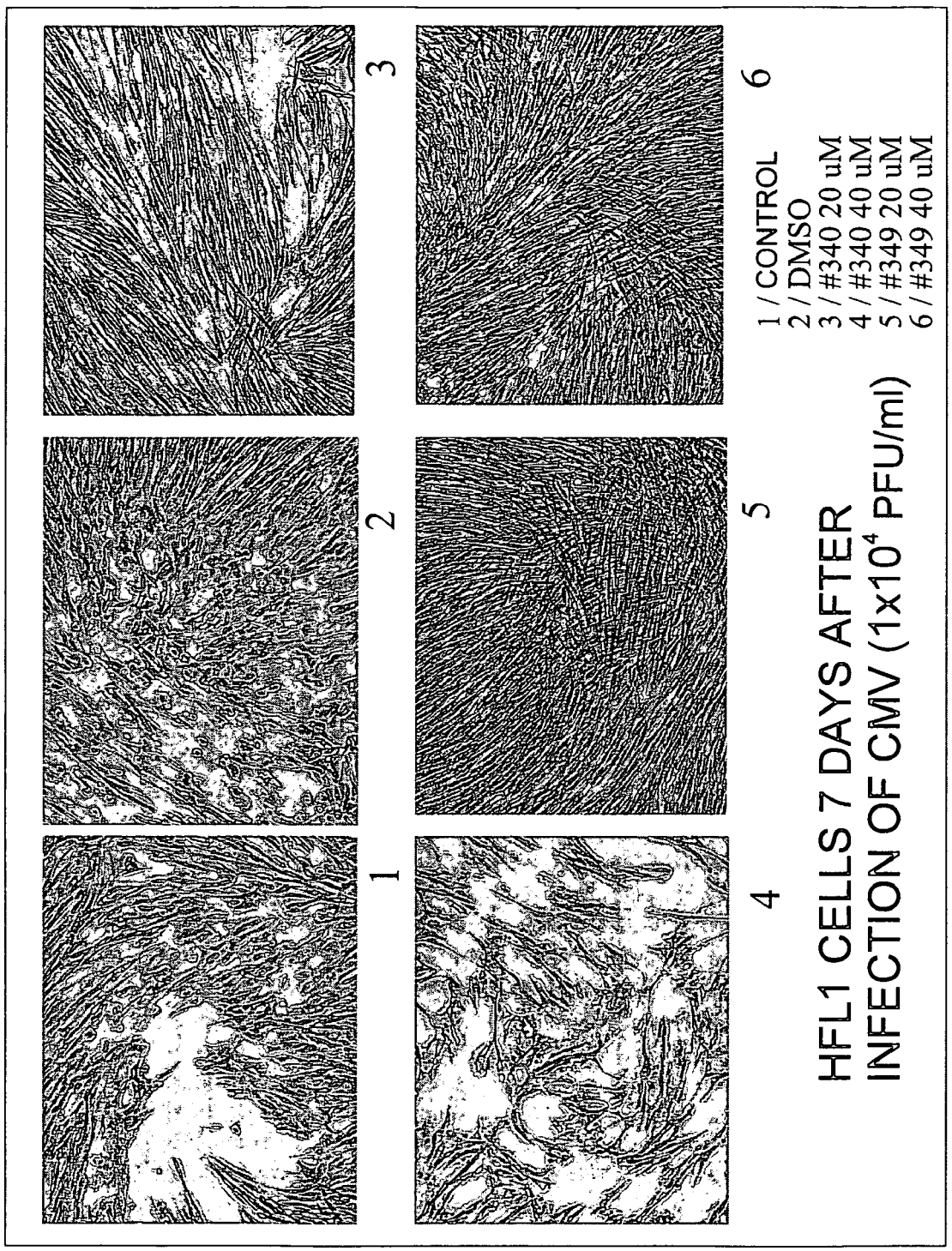
FIG. 7: Antiviral activity of SRPIN-1 and analogs thereof against cytomegalovirus. This figure shows phase contrast microscopic images of cytomegalovirus-infected cells. Morphological alterations characteristic of cytomegalovirus infection and cell death were frequently found in control group cells (1 and 2 in this figure). In contrast, the abnormal morphological alterations and cell death caused by cytomegalovirus infection were inhibited in cells to which 20 µl of SRPIN-1 or an analog thereof (Compound No. 349) was added (3 and 5 in this figure).

Cytomegalovirus (1×10$^4$ PFU/ml) and SRPIN-1 or an analog thereof (Compound No. 340 or 349; final concentration: 20 or 40 μM) were simultaneously added to HFL1 cells (IF050074). The HFL1 cells infected with cytomegalovirus were observed under a phase contrast microscope seven days after infection. As shown in FIG. 7, morphological changes characteristic of cytomegalovirus infection and cell death were found with high frequency in control group HFL1 cells (1 and 2 in this Figure), to which no SRPIN-1 was added. In contrast, when SRPIN-1 (20 μM) was added to the HFL1 cells, neither abnormal morphological changes nor cell death were detectable (3 in this Figure), despite the cytomegalovirus infection. Partial morphological changes thought to be induced by SRPIN-1 were detectable in HFL1 cells to which SRPIN-1 was added at a higher concentration (40 μM). Further, addition of an SRPIN-1 analog compound (Compound No. 349) at 20 or 40 μM to HFL1 cells also suppressed the abnormal morphological changes and cell death caused by cytomegalovirus infection (5 and 6 in this Figure). Thus, it was demonstrated that under these assay conditions SRPIN-1 and its analog compounds could suppress the changes in cell morphology and cell death caused by cytomegalovirus infection.

Example 8

Suppressing Effect on SARS Virus Propagation

Figure 8:
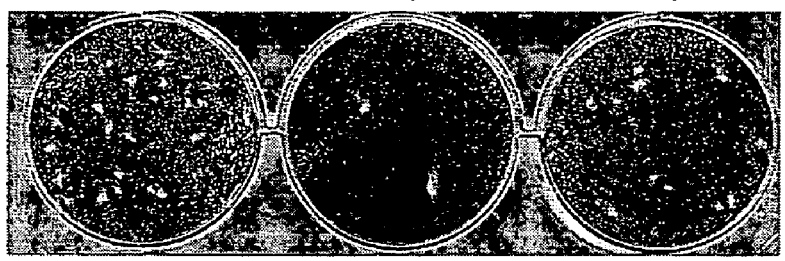
FIG. 8: Antiviral activities of SRPIN-1 and analogs thereof against SARS virus. This figure shows the results of plaque assays for SARS virus-infected cells. The number of plaques where SARS virus infection resulted in cell death was determined to evaluate the antiviral activity of SRPIN-1 and analogs thereof (plaque assay). As activity or expression level of SR proteins. To reduce the activity or expression level of an SR protein, for example, in addition to using the SR protein as a direct target, it is also preferable to inhibit phosphorylation of the SR protein by SRPKs and/or enhance dephosphorylation. Dephosphorylation of SR proteins is promoted, for example, by activating protein phosphatase 2A (also referred to as phosphatase 2A). Thus, viral propagation can be inhibited by using a compound that increases the expression and/or activity of protein phosphatase 2A. Phosphorylation of SR proteins can also be inhibited by inhibiting the expression and/or activity of SRPKs. Thus, SRPK inhibitors are preferable antiviral agents of the present invention.
Figure 8:
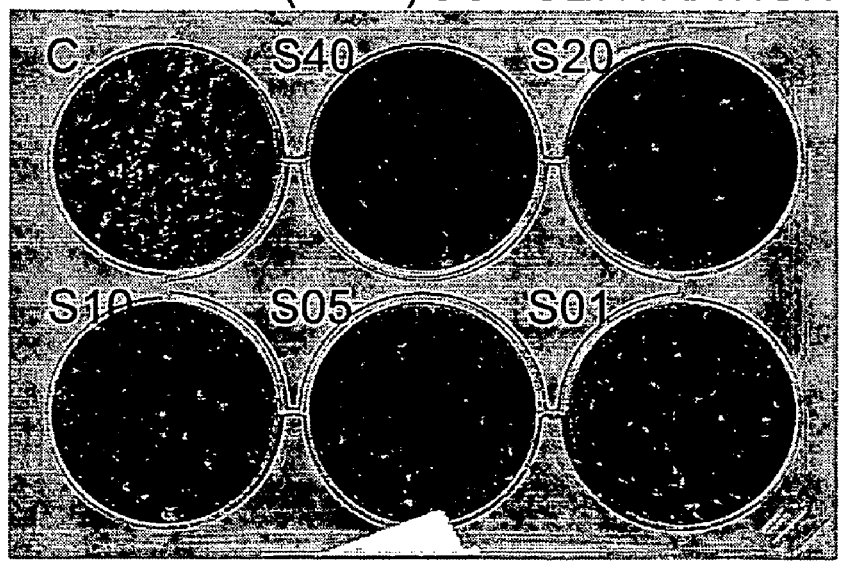

Vero cells (JCRB0111) were infected with SARS virus (FFM-1) (Yamamoto, N. et al., Biochem Biophys Res Commun. 318, 719-725 (2004)), and simultaneously SRPIN-1 or an analog thereof (final concentration: 5, 10, 20, or 40 μM) was added thereto. After two hours of infection at room temperature, D-MEM containing 1% methylcellulose (SIGMA M0512-100 G) was added and the cells were cultured at 37° C. under 5% $CO_2$ for 48 hours. The number of plaques formed by cell death caused by SARS virus infection was counted (plaque assay) to calculate PFU/ml. As shown in FIG. 8A, 40 μM SRPIN-1 and an analog compound thereof (Compound No. 349) significantly suppressed SARS virus propagation. The viral propagation-suppressing effect of SRPIN-1 was stronger than that of the analog compound (Compound No. 349). In addition, as seen in FIG. 8B, SRPIN-1 was found to suppress SARS virus propagation in a concentration-dependent manner within the concentration range of 1 to 40 μM.

INDUSTRIAL APPLICABILITY

The present invention revealed that SRPIN-1 (SR protein phosphorylation inhibitor 1) and analogs thereof have the activity of inhibiting SRPK kinases. When phosphorylated by SRPKs, SR proteins are stable in cells. However, SR proteins were found to be degraded via the ubiquitin-proteasome pathway when SR protein phosphorylation was inhibited by using SRPK inhibitors to inhibit SRPK enzymatic activity. Thus, the SRPK inhibitors were added to inhibit SRPK in HIV infection experiments, and were found to have the antiviral activity of suppressing viral replication.

The present invention is also beneficial in that it provides antiviral agents that control the activity of SR proteins, and thus by the same mechanism are effective against a broad range of viruses.

---

The invention claimed is:

1. A method for the treatment of a viral infection in a subject in need thereof, comprising administering to the subject in need of treatment for the viral infection, in an amount effective to treat the viral infection, an aniline derivative represented by the following formula (I):

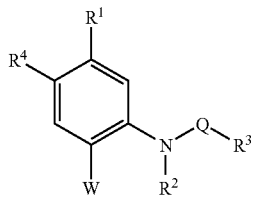

or a pharmaceutically acceptable salt or hydrate thereof, wherein, $R^1$ represents a hydrogen atom, a $C_{1-6}$ alkyl group which may have a substituent, a $C_{2-6}$ alkenyl group which may have a substituent, a $C_{2-6}$ alkynyl group which may have a substituent, a $C_{6-10}$ aryl group which may have a substituent, a halogen atom, a nitro group, a cyano group, an azide group, a hydroxy group, a $C_{1-6}$ alkoxy group which may have a substituent, a $C_{1-6}$ alkylthio group which may have a substituent, a $C_{1-6}$ alkylsulfonyl group which may have a substituent, a carboxyl group, a formyl group, a $C_{1-6}$ alkoxycarbonyl group which may have a substituent, an acyl group, an acylamino group, or a sulfamoyl group;

$R^2$ represents a hydrogen atom;

$R^3$ represents a $C_{6-10}$ aryl group which may have a substituent, or a nitrogen-containing heterocycle which may have a substituent;

$R^4$ represents a hydrogen atom;

Q represents —C(O)—, —C(S)—, —SO$_2$—, —C(S)NHC(O)—, —C(O)NHC(O)—, or —C(O)NHC(S)—;

W represents a hydrogen atom, a $C_{1-6}$ alkyl group which may have a substituent, a $C_{6-10}$ aryl group which may have a substituent, a halogen atom, a hydroxy group, a $C_{1-6}$ alkoxy group which may have a substituent, a $C_{1-6}$ alkylthio group which may have a substituent, a nitrogen-containing heterocycle which may have a substituent, a condensed aromatic heterocycle which may have a substituent, or a group represented by the following formula (II):

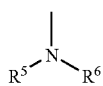

wherein, $R^5$ and $R^6$ are the same or different and each represents a hydrogen atom, a $C_{1-6}$ alkyl group which may have a substituent, a nitrogen-containing heterocycle which may have a substituent, a condensed aromatic heterocycle which may have a substituent, an acyl group, or an acylamino group;

the above $R^5$ and $R^6$ together with the adjacent nitrogen atom may form a heterocycle which may have a substituent, and the heterocycle may be a condensed aromatic heterocycle which may have a substituent;

the above $R^5$ and $R^6$ may be a cycloalkylidene amino group which may have a substituent, or an aromatic condensed cycloalkylidene group which may have a substituent, thereby treating the viral infection in the subject, and wherein the viral infection is caused by:

(1) any one of the following RNA viruses: severe acute respiratory syndrome (SARS), poliovirus, human rhinovirus, hepatitis A, C, D, and E viruses, vaccinia virus, Japanese encephalitis virus, dengue virus, human coronavirus, Ebola virus, influenza virus, or sindbis virus; or (2) any one of the following DNA viruses: a herpes simplex virus, human adenovirus, hepatitis B virus, cytomegalovirus, EB virus, herpesvirus, human herpesvirus, smallpox virus, polyoma virus, or human papilloma virus.

2. The method of claim 1, wherein $R^1$ is a hydrogen atom, a $C_{1-6}$ alkyl group which may have a substituent, or a halogen atom;

$R^2$ is a hydrogen atom;

$R^3$ is a $C_{6-10}$ aryl group which may have a substituent, or a nitrogen-containing 5- to 10-membered heteroaryl group which may have a substituent;

$R^4$ is a hydrogen atom;

Q represents —C(O)—, —C(S)—, —SO$_2$—, —C(S)NHC(O)—, —C(O)NHC(O)—, or —C(O)NHC(S)—;

W represents a hydrogen atom, a halogen atom, or a group represented by the following formula (II):

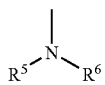

wherein, $R^5$ and $R^6$ are the same or different and each represent a $C_{1-6}$ alkyl group which may have a substituent; or the above $R^5$ and $R^6$ together with the adjacent nitrogen atom may form a heterocyclic group which may have a substituent, and the heterocyclic group may be a condensed aromatic heterocyclic group which may have a substituent.

3. The method of claim 1, wherein the aniline derivative of formula (I) is represented by the following formula (III):

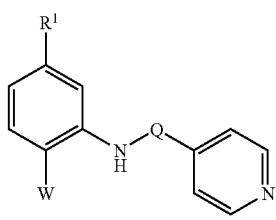

or a pharmaceutically acceptable salt or hydrate thereof, wherein, $R^1$ is a hydrogen atom, a fluorine atom or a trifluoromethyl group;

W represents

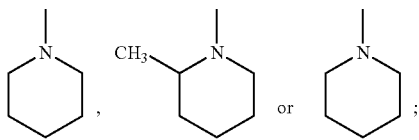

Q represents —C(O)— or —C(S)—.

4. The method of claim 1, wherein the viral infection is caused by any one of the following DNA viruses: a herpes simplex virus, human adenovirus, hepatitis B virus, cytomegalovirus, EB virus, herpesvirus, human herpesvirus, smallpox virus, polyoma virus, or human papilloma virus.

5. The method of claim 1, wherein the viral infection is caused by a herpes simplex virus.

6. The method of claim 1, wherein the viral infection is caused by a human adenovirus.

7. The method of claim 1, wherein the viral infection is caused by a cytomegalovirus.

* * * * *

UNITED STATES PATENT AND TRADEMARK OFFICE
CERTIFICATE OF CORRECTION

PATENT NO.        : 7,569,536 B2
APPLICATION NO.   : 10/584482
DATED             : August 4, 2009
INVENTOR(S)       : Hagiwara et al.

It is certified that error appears in the above-identified patent and that said Letters Patent is hereby corrected as shown below:

On the Title Pg, in the Title, Item (54):

In the title of the invention, "METHOD" should be --METHODS--.

Column 1, line 54, "Vol. 86" should be --Vol. 83--.

Column 15, line 36, "[46]" should be --[M6]--.

Column 35, "X" in subpart 3a, should be --N--, as follows:
$W = HNR^4R^5$

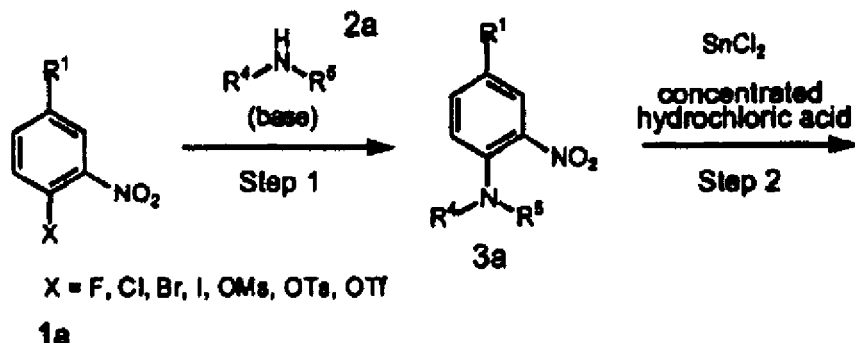

Column 35, --$R^3$-- should be added to subpart 6a, as follows:

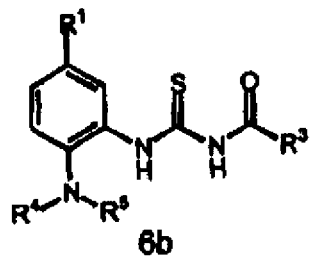

UNITED STATES PATENT AND TRADEMARK OFFICE
CERTIFICATE OF CORRECTION

PATENT NO. : 7,569,536 B2
APPLICATION NO. : 10/584482
DATED : August 4, 2009
INVENTOR(S) : Hagiwara et al.

It is certified that error appears in the above-identified patent and that said Letters Patent is hereby corrected as shown below:

Column 38, line 44, "P4S$_{10}$" should be --P$_4$S$_{10}$--.

Column 64, line 65, "Cl" should be --F--.

Column 65, line 20, "DMAP", appearing under "Et$_3$N", should be deleted.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,569,536 B2
APPLICATION NO. : 10/584482
DATED : August 4, 2009
INVENTOR(S) : Hagiwara et al.

It is certified that error appears in the above-identified patent and that said Letters Patent is hereby corrected as shown below:

On the Title Pg, Item (54) and at Column 1, line 1, in the title:

In the title of the invention, "METHOD" should be --METHODS--.

Column 1, line 54, "Vol. 86" should be --Vol. 83--.

Column 15, line 36, "[46]" should be --[M6]--.

Column 35, "X" in subpart 3a, should be --N--, as follows:
   $W = HNR^4R^5$

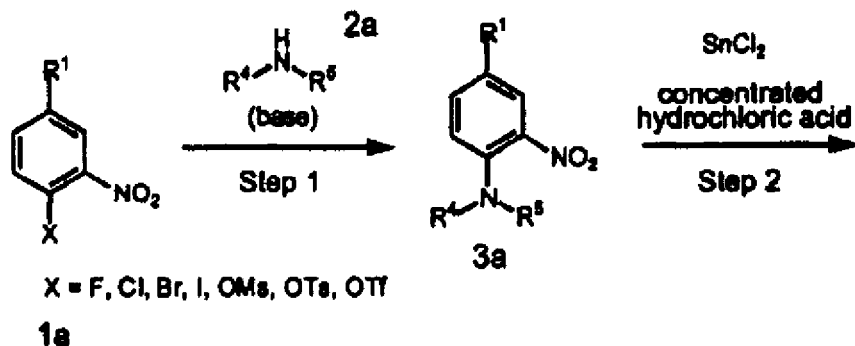

Column 35, --$R^3$-- should be added to subpart 6a, as follows:

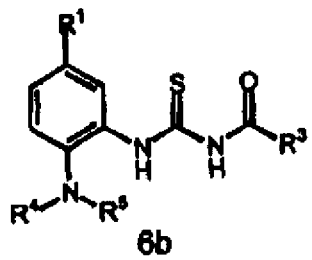

CERTIFICATE OF CORRECTION (continued)
U.S. Pat. No. 7,569,536 B2

Column 38, line 44, "P4S$_{10}$" should be --P$_4$S$_{10}$--.

Column 64, line 65, "Cl" should be --F--.

Column 65, line 20, "DMAP", appearing under "Et$_3$N", should be deleted.

This certificate supersedes the Certificate of Correction issued December 22, 2009.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,569,536 B2
APPLICATION NO. : 10/584482
DATED : August 4, 2009
INVENTOR(S) : Hagiwara et al.

It is certified that error appears in the above-identified patent and that said Letters Patent is hereby corrected as shown below:

On the Title Pg, Item (54) and at Column 1, line 1, in the title:

In the title of the invention, "METHOD" should be --METHODS--.

Column 1, line 54, "Vol. 86" should be --Vol. 83--.

Column 15, line 36, "[46]" should be --[M6]--.

Column 35, "X" in subpart 3a, should be --N--, as follows:
    $W = HNR^4R^5$

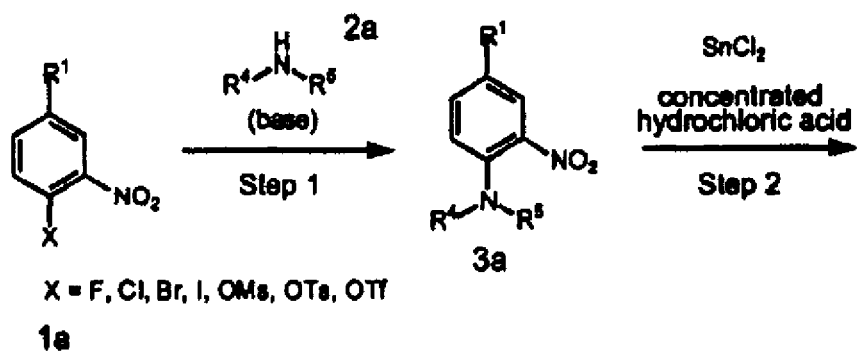

Column 35, --$R^3$-- should be added to subpart 6b, as follows:

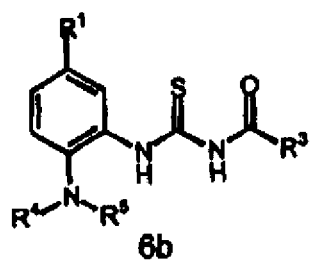

CERTIFICATE OF CORRECTION (continued)
U.S. Pat. No. 7,569,536 B2

Column 38, line 44, "P4S₁₀" should be --$P_4S_{10}$--.

Column 64, line 65, "Cl" should be --F--.

Column 65, line 20, "DMAP", appearing under "Et₃N", should be deleted.

This certificate supersedes the Certificates of Correction issued December 22, 2009 and January 12, 2010.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,569,536 B2 Page 1 of 1
APPLICATION NO. : 10/584482
DATED : August 4, 2009
INVENTOR(S) : Hagiwara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 39 days.

Signed and Sealed this

Seventh Day of September, 2010

David J. Kappos
*Director of the United States Patent and Trademark Office*

SEQUENCE LISTING

```
<160> NUMBER OF SEQ ID NOS: 5

<210> SEQ ID NO 1
<211> LENGTH: 1965
<212> TYPE: DNA
<213> ORGANISM: Homo sapiens
<220> FEATURE:
<221> NAME/KEY: CDS
<222> LOCATION: (1)..(1965)
<223> OTHER INFORMATION:

<400> SEQUENCE: 1 atg gag cgg aaa gtg ctt gcg ctc cag gcc cga aag aaa agg acc aag      48
Met Glu Arg Lys Val Leu Ala Leu Gln Ala Arg Lys Lys Arg Thr Lys
1               5                   10                  15 gcc aag aag gac aaa gcc caa agg aaa tct gaa act cag cac cga ggc      96
Ala Lys Lys Asp Lys Ala Gln Arg Lys Ser Glu Thr Gln His Arg Gly
            20                  25                  30 tct gct ccc cac tct gag agt gat cta cca gag cag gaa gag gag att     144
Ser Ala Pro His Ser Glu Ser Asp Leu Pro Glu Gln Glu Glu Glu Ile
```

-continued

```
                 35                  40                  45
ctg gga tct gat gat gat gag caa gaa gat cct aat gat tat tgt aaa          192
Leu Gly Ser Asp Asp Asp Glu Gln Glu Asp Pro Asn Asp Tyr Cys Lys
         50                  55                  60 gga ggt tat cat ctt gtg aaa att gga gat cta ttc aat ggg aga tac          240
Gly Gly Tyr His Leu Val Lys Ile Gly Asp Leu Phe Asn Gly Arg Tyr
 65                  70                  75                  80 cat gtg atc cga aag tta ggc tgg gga cac ttt tca aca gta tgg tta          288
His Val Ile Arg Lys Leu Gly Trp Gly His Phe Ser Thr Val Trp Leu
                 85                  90                  95 tca tgg gat att cag ggg aag aaa ttt gtg gca atg aaa gta gtt aaa          336
Ser Trp Asp Ile Gln Gly Lys Lys Phe Val Ala Met Lys Val Val Lys
                100                 105                 110 agt gct gaa cat tac act gaa aca gca cta gat gaa atc cgg ttg ctg          384
Ser Ala Glu His Tyr Thr Glu Thr Ala Leu Asp Glu Ile Arg Leu Leu
                115                 120                 125 aag tca gtt cgc aat tca gac cct aat gat cca aat aga gaa atg gtt          432
Lys Ser Val Arg Asn Ser Asp Pro Asn Asp Pro Asn Arg Glu Met Val
                130                 135                 140 gtt caa cta cta gat gac ttt aaa ata tca gga gtt aat gga aca cat          480
Val Gln Leu Leu Asp Asp Phe Lys Ile Ser Gly Val Asn Gly Thr His
145                 150                 155                 160 atc tgc atg gta ttt gaa gtt ttg ggg cat cat ctg ctc aag tgg atc          528
Ile Cys Met Val Phe Glu Val Leu Gly His His Leu Leu Lys Trp Ile
                165                 170                 175 atc aaa tcc aat tat cag ggg ctt cca ctg cct tgt gtc aaa aaa att          576
Ile Lys Ser Asn Tyr Gln Gly Leu Pro Leu Pro Cys Val Lys Lys Ile
                180                 185                 190 att cag caa gtg tta cag ggt ctt gat tat tta cat acc aag tgc cgt          624
Ile Gln Gln Val Leu Gln Gly Leu Asp Tyr Leu His Thr Lys Cys Arg
                195                 200                 205 atc atc cac act gac att aaa cca gag aac atc tta ttg tca gtg aat          672
Ile Ile His Thr Asp Ile Lys Pro Glu Asn Ile Leu Leu Ser Val Asn
        210                 215                 220 gag cag tac att cgg agg ctg gct gca gaa gca aca gaa tgg cag cga          720
Glu Gln Tyr Ile Arg Arg Leu Ala Ala Glu Ala Thr Glu Trp Gln Arg
225                 230                 235                 240 tct gga gct cct ccg cct tcc gga tct gca gtc agt act gct ccc cag          768
Ser Gly Ala Pro Pro Pro Ser Gly Ser Ala Val Ser Thr Ala Pro Gln
                245                 250                 255 cct aaa cca gct gac aaa atg tca aag aat aag aag aag aaa ttg aag          816
Pro Lys Pro Ala Asp Lys Met Ser Lys Asn Lys Lys Lys Lys Leu Lys
                260                 265                 270 aag aag cag aag cgc cag gca gaa tta cta gag aag cga atg cag gaa          864
Lys Lys Gln Lys Arg Gln Ala Glu Leu Leu Glu Lys Arg Met Gln Glu
                275                 280                 285 att gag gaa atg gag aaa gag tcg ggc cct ggg caa aaa aga cca aac          912
Ile Glu Glu Met Glu Lys Glu Ser Gly Pro Gly Gln Lys Arg Pro Asn
                290                 295                 300 aag caa gaa gaa tca gag agt cct gtt gaa aga ccc ttg aaa gag aac          960
Lys Gln Glu Glu Ser Glu Ser Pro Val Glu Arg Pro Leu Lys Glu Asn
305                 310                 315                 320 cca cct aat aaa atg acc caa gaa aaa ctt gaa gag tca agt acc att         1008
Pro Pro Asn Lys Met Thr Gln Glu Lys Leu Glu Glu Ser Ser Thr Ile
                325                 330                 335 ggc cag gat caa acg ctt atg gaa cgt gat aca gag ggt ggt gca gca         1056
Gly Gln Asp Gln Thr Leu Met Glu Arg Asp Thr Glu Gly Gly Ala Ala
                340                 345                 350 gaa att aat tgc aat gga gtg att gaa gtc att aat tat act cag aac         1104
```

-continued

```
                Glu Ile Asn Cys Asn Gly Val Ile Glu Val Ile Asn Tyr Thr Gln Asn
                    355                 360                 365 agt aat aat gaa aca ttg aga cat aaa gag gat cta cat aat gct aat      1152
Ser Asn Asn Glu Thr Leu Arg His Lys Glu Asp Leu His Asn Ala Asn
    370                 375                 380 gac tgt gat gtc caa aat ttg aat cag gaa tct agt ttc cta agc tcc      1200
Asp Cys Asp Val Gln Asn Leu Asn Gln Glu Ser Ser Phe Leu Ser Ser
385                 390                 395                 400 caa aat gga gac agc agc aca tct caa gaa aca gac tct tgt aca cct      1248
Gln Asn Gly Asp Ser Ser Thr Ser Gln Glu Thr Asp Ser Cys Thr Pro
                405                 410                 415 ata aca tct gag gtg tca gac acc atg gtg tgc cag tct tcc tca act      1296
Ile Thr Ser Glu Val Ser Asp Thr Met Val Cys Gln Ser Ser Ser Thr
            420                 425                 430 gta ggt cag tca ttc agt gaa caa cac att agc caa ctt caa gaa agc      1344
Val Gly Gln Ser Phe Ser Glu Gln His Ile Ser Gln Leu Gln Glu Ser
        435                 440                 445 att cgg gca gag ata ccc tgt gaa gat gaa caa gag caa gaa cat aac      1392
Ile Arg Ala Glu Ile Pro Cys Glu Asp Glu Gln Glu Gln Glu His Asn
    450                 455                 460 gga cca ctg gac aac aaa gga aaa tcc acg gct gga aat ttt ctt gtt      1440
Gly Pro Leu Asp Asn Lys Gly Lys Ser Thr Ala Gly Asn Phe Leu Val
465                 470                 475                 480 aat ccc ctt gag cca aaa aat gca gaa aag ctc aag gtg aag att gct      1488
Asn Pro Leu Glu Pro Lys Asn Ala Glu Lys Leu Lys Val Lys Ile Ala
                485                 490                 495 gac ctt gga aat gct tgt tgg gtg cac aaa cat ttc act gaa gat att      1536
Asp Leu Gly Asn Ala Cys Trp Val His Lys His Phe Thr Glu Asp Ile
            500                 505                 510 caa aca agg caa tat cgt tcc ttg gaa gtt cta atc gga tct ggc tat      1584
Gln Thr Arg Gln Tyr Arg Ser Leu Glu Val Leu Ile Gly Ser Gly Tyr
        515                 520                 525 aat acc cct gct gac att tgg agc acg gca tgc atg gcc ttt gaa ctg      1632
Asn Thr Pro Ala Asp Ile Trp Ser Thr Ala Cys Met Ala Phe Glu Leu
    530                 535                 540 gcc aca ggt gac tat ttg ttt gaa cct cat tca ggg gaa gag tac act      1680
Ala Thr Gly Asp Tyr Leu Phe Glu Pro His Ser Gly Glu Glu Tyr Thr
545                 550                 555                 560 cga gat gaa gat cac att gca ttg atc ata gaa ctt ctg ggg aag gtg      1728
Arg Asp Glu Asp His Ile Ala Leu Ile Ile Glu Leu Leu Gly Lys Val
                565                 570                 575 cct cgc aag ctc att gtg gca gga aaa tat tcc aag gaa ttt ttc acc      1776
Pro Arg Lys Leu Ile Val Ala Gly Lys Tyr Ser Lys Glu Phe Phe Thr
            580                 585                 590 aaa aaa ggt gac ctg aaa cat atc acg aag ctg aaa cct tgg ggc ctt      1824
Lys Lys Gly Asp Leu Lys His Ile Thr Lys Leu Lys Pro Trp Gly Leu
        595                 600                 605 ttt gag gtt cta gtg gag aag tat gag tgg tcg cag gaa gag gca gct      1872
Phe Glu Val Leu Val Glu Lys Tyr Glu Trp Ser Gln Glu Glu Ala Ala
    610                 615                 620 ggc ttc aca gat ttc tta ctg ccc atg ttg gag ctg atc cct gag aag      1920
Gly Phe Thr Asp Phe Leu Leu Pro Met Leu Glu Leu Ile Pro Glu Lys
625                 630                 635                 640 aga gcc act gcc gcc gag tgt ctc cgg cac cct tgg ctt aac tcc          1965
Arg Ala Thr Ala Ala Glu Cys Leu Arg His Pro Trp Leu Asn Ser
                645                 650                 655

<210> SEQ ID NO 2
<211> LENGTH: 655
<212> TYPE: PRT
```

<213> ORGANISM: Homo sapiens

<400> SEQUENCE: 2

```
Met Glu Arg Lys Val Leu Ala Leu Gln Ala Arg Lys Lys Arg Thr Lys
1               5                   10                  15

Ala Lys Lys Asp Lys Ala Gln Arg Lys Ser Glu Thr Gln His Arg Gly
            20                  25                  30

Ser Ala Pro His Ser Glu Ser Asp Leu Pro Glu Gln Glu Glu Glu Ile
        35                  40                  45

Leu Gly Ser Asp Asp Glu Gln Asp Pro Asn Asp Tyr Cys Lys
    50                  55                  60

Gly Gly Tyr His Leu Val Lys Ile Gly Asp Leu Phe Asn Gly Arg Tyr
65              70                  75                  80

His Val Ile Arg Lys Leu Gly Trp Gly His Phe Ser Thr Val Trp Leu
                85                  90                  95

Ser Trp Asp Ile Gln Gly Lys Lys Phe Val Ala Met Lys Val Val Lys
            100                 105                 110

Ser Ala Glu His Tyr Thr Glu Thr Ala Leu Asp Glu Ile Arg Leu Leu
        115                 120                 125

Lys Ser Val Arg Asn Ser Asp Pro Asn Asp Pro Asn Arg Glu Met Val
    130                 135                 140

Val Gln Leu Leu Asp Asp Phe Lys Ile Ser Gly Val Asn Gly Thr His
145                 150                 155                 160

Ile Cys Met Val Phe Glu Val Leu Gly His His Leu Leu Lys Trp Ile
                165                 170                 175

Ile Lys Ser Asn Tyr Gln Gly Leu Pro Leu Pro Cys Val Lys Lys Ile
            180                 185                 190

Ile Gln Gln Val Leu Gln Gly Leu Asp Tyr Leu His Thr Lys Cys Arg
        195                 200                 205

Ile Ile His Thr Asp Ile Lys Pro Glu Asn Ile Leu Leu Ser Val Asn
    210                 215                 220

Glu Gln Tyr Ile Arg Arg Leu Ala Ala Glu Ala Thr Glu Trp Gln Arg
225                 230                 235                 240

Ser Gly Ala Pro Pro Ser Gly Ser Ala Val Ser Thr Ala Pro Gln
                245                 250                 255

Pro Lys Pro Ala Asp Lys Met Ser Lys Asn Lys Lys Lys Leu Lys
            260                 265                 270

Lys Lys Gln Lys Arg Gln Ala Glu Leu Leu Glu Lys Arg Met Gln Glu
        275                 280                 285

Ile Glu Glu Met Glu Lys Glu Ser Gly Pro Gly Gln Lys Arg Pro Asn
    290                 295                 300

Lys Gln Glu Glu Ser Glu Ser Pro Val Glu Arg Pro Leu Lys Glu Asn
305                 310                 315                 320

Pro Pro Asn Lys Met Thr Gln Glu Lys Leu Glu Ser Ser Thr Ile
                325                 330                 335

Gly Gln Asp Gln Thr Leu Met Glu Arg Asp Thr Glu Gly Gly Ala Ala
            340                 345                 350

Glu Ile Asn Cys Asn Gly Val Ile Glu Val Ile Asn Tyr Thr Gln Asn
        355                 360                 365

Ser Asn Asn Glu Thr Leu Arg His Lys Glu Asp Leu His Asn Ala Asn
    370                 375                 380

Asp Cys Asp Val Gln Asn Leu Asn Gln Glu Ser Ser Phe Leu Ser Ser
385                 390                 395                 400
```

```
Gln Asn Gly Asp Ser Ser Thr Ser Gln Glu Thr Asp Ser Cys Thr Pro
            405                 410                 415

Ile Thr Ser Glu Val Ser Asp Thr Met Val Cys Gln Ser Ser Ser Thr
            420                 425                 430

Val Gly Gln Ser Phe Ser Glu Gln His Ile Ser Gln Leu Gln Glu Ser
            435                 440                 445

Ile Arg Ala Glu Ile Pro Cys Glu Asp Glu Gln Glu Gln His Asn
450                 455                 460

Gly Pro Leu Asp Asn Lys Gly Lys Ser Thr Ala Gly Asn Phe Leu Val
465                 470                 475                 480

Asn Pro Leu Glu Pro Lys Asn Ala Glu Lys Leu Lys Val Lys Ile Ala
                485                 490                 495

Asp Leu Gly Asn Ala Cys Trp Val His Lys His Phe Thr Glu Asp Ile
            500                 505                 510

Gln Thr Arg Gln Tyr Arg Ser Leu Glu Val Leu Ile Gly Ser Gly Tyr
            515                 520                 525

Asn Thr Pro Ala Asp Ile Trp Ser Thr Ala Cys Met Ala Phe Glu Leu
530                 535                 540

Ala Thr Gly Asp Tyr Leu Phe Glu Pro His Ser Gly Glu Glu Tyr Thr
545                 550                 555                 560

Arg Asp Glu Asp His Ile Ala Leu Ile Ile Glu Leu Leu Gly Lys Val
                565                 570                 575

Pro Arg Lys Leu Ile Val Ala Gly Lys Tyr Ser Lys Glu Phe Phe Thr
            580                 585                 590

Lys Lys Gly Asp Leu Lys His Ile Thr Lys Leu Lys Pro Trp Gly Leu
            595                 600                 605

Phe Glu Val Leu Val Glu Lys Tyr Glu Trp Ser Gln Glu Glu Ala Ala
            610                 615                 620

Gly Phe Thr Asp Phe Leu Leu Pro Met Leu Glu Leu Ile Pro Glu Lys
625                 630                 635                 640

Arg Ala Thr Ala Ala Glu Cys Leu Arg His Pro Trp Leu Asn Ser
                645                 650                 655

<210> SEQ ID NO 3
<211> LENGTH: 2058
<212> TYPE: DNA
<213> ORGANISM: Homo sapiens
<220> FEATURE:
<221> NAME/KEY: CDS
<222> LOCATION: (1)..(2058)
<223> OTHER INFORMATION:

<400> SEQUENCE: 3 atg tca gtt aac tct gag aag tcg tcc tct tca gaa agg ccg gag cct    48
Met Ser Val Asn Ser Glu Lys Ser Ser Ser Ser Glu Arg Pro Glu Pro
1               5                  10                  15 caa cag aaa gct cct tta gtt cct cct cct ccg cca cca cca cca        96
Gln Gln Lys Ala Pro Leu Val Pro Pro Pro Pro Pro Pro Pro Pro
            20                  25                  30 cca ccg cca cct ttg cca gac ccc aca ccc ccg gag cca gag gag gag    144
Pro Pro Pro Pro Leu Pro Asp Pro Thr Pro Pro Glu Pro Glu Glu Glu
        35                  40                  45 atc ctg gga tca gat gat gag gag caa gag gac cct gcg gac tac tgc    192
Ile Leu Gly Ser Asp Asp Glu Glu Gln Glu Asp Pro Ala Asp Tyr Cys
50                  55                  60 aaa ggt gga tat cat cca gtg aaa att gga gac ctc ttc aat ggc cgg    240
Lys Gly Gly Tyr His Pro Val Lys Ile Gly Asp Leu Phe Asn Gly Arg
65                  70                  75                  80
```

```
                                                            -continued tat cat gtt att aga aag ctt gga tgg ggg cac ttc tct act gtc tgg    288
Tyr His Val Ile Arg Lys Leu Gly Trp Gly His Phe Ser Thr Val Trp
             85                  90                  95 ctg tgc tgg gat atg cag ggg aaa aga ttt gtt gca atg aaa gtt gta    336
Leu Cys Trp Asp Met Gln Gly Lys Arg Phe Val Ala Met Lys Val Val
        100                 105                 110 aaa agt gcc cag cat tat acg gag aca gcc ttg gat gaa ata aaa ttg    384
Lys Ser Ala Gln His Tyr Thr Glu Thr Ala Leu Asp Glu Ile Lys Leu
            115                 120                 125 ctc aaa tgt gtt cga gaa agt gat ccc agt gac cca aac aaa gac atg    432
Leu Lys Cys Val Arg Glu Ser Asp Pro Ser Asp Pro Asn Lys Asp Met
130                 135                 140 gtg gtc cag ctc att gac gac ttc aag att tca ggc atg aat ggg ata    480
Val Val Gln Leu Ile Asp Asp Phe Lys Ile Ser Gly Met Asn Gly Ile
145                 150                 155                 160 cat gtc tgc atg gtc ttc gaa gta ctt ggc cat ctc ctc aag tgg        528
His Val Cys Met Val Phe Glu Val Leu Gly His His Leu Leu Lys Trp
                165                 170                 175 atc atc aaa tcc aac tat caa ggc ctc cca gta cgt tgt gtg aag agt    576
Ile Ile Lys Ser Asn Tyr Gln Gly Leu Pro Val Arg Cys Val Lys Ser
            180                 185                 190 atc att cga cag gtc ctt caa ggg tta gat tac tta cac agt aag tgc    624
Ile Ile Arg Gln Val Leu Gln Gly Leu Asp Tyr Leu His Ser Lys Cys
            195                 200                 205 aag atc att cat act gac ata aag ccg gaa aat atc ttg atg tgt gtg    672
Lys Ile Ile His Thr Asp Ile Lys Pro Glu Asn Ile Leu Met Cys Val
        210                 215                 220 gat gat gca tat gtg aga aga atg gca gct gag cct gag tgg cag aaa    720
Asp Asp Ala Tyr Val Arg Arg Met Ala Ala Glu Pro Glu Trp Gln Lys
225                 230                 235                 240 gca ggt gct cct cct cct tca ggg tct gca gtg agt acg gct cca cag    768
Ala Gly Ala Pro Pro Pro Ser Gly Ser Ala Val Ser Thr Ala Pro Gln
                245                 250                 255 cag aaa cct ata gga aaa ata tct aaa aac aaa aag aaa aaa ctg aaa    816
Gln Lys Pro Ile Gly Lys Ile Ser Lys Asn Lys Lys Lys Lys Leu Lys
            260                 265                 270 aag aaa cag aag agg cag gct gag tta ttg gag aag cgc ctg cag gag    864
Lys Lys Gln Lys Arg Gln Ala Glu Leu Leu Glu Lys Arg Leu Gln Glu
        275                 280                 285 ata gaa gaa ttg gag cga gaa gct gaa agg aaa ata ata gaa gaa aac    912
Ile Glu Glu Leu Glu Arg Glu Ala Glu Arg Lys Ile Ile Glu Glu Asn
    290                 295                 300 atc acc tca gct gca cct tcc aat gac cag gat ggc gaa tac tgc cca    960
Ile Thr Ser Ala Ala Pro Ser Asn Asp Gln Asp Gly Glu Tyr Cys Pro
305                 310                 315                 320 gag gtg aaa cta aaa aca aca gga tta gag gag gcg gct gag gca gag    1008
Glu Val Lys Leu Lys Thr Thr Gly Leu Glu Glu Ala Ala Glu Ala Glu
                325                 330                 335 act gca aag gac aat ggt gaa gct gag gac cag gaa gag aaa gaa gat    1056
Thr Ala Lys Asp Asn Gly Glu Ala Glu Asp Gln Glu Glu Lys Glu Asp
            340                 345                 350 gct gag aaa gaa aac att gaa aaa gat gaa gat gat gta gat cag gaa    1104
Ala Glu Lys Glu Asn Ile Glu Lys Asp Glu Asp Asp Val Asp Gln Glu
        355                 360                 365 ctt gcg aac ata gac cct acg tgg ata gaa tca cct aaa acc aat ggc    1152
Leu Ala Asn Ile Asp Pro Thr Trp Ile Glu Ser Pro Lys Thr Asn Gly
    370                 375                 380 cat att gag aat ggc cca ttc tca ctg gag cag caa ctg gac gat gaa    1200
His Ile Glu Asn Gly Pro Phe Ser Leu Glu Gln Gln Leu Asp Asp Glu
```

```
                385                 390                 395                 400
gat gat gat gaa gaa gac tgc cca aat cct gag gaa tat aat ctt gat          1248
Asp Asp Asp Glu Glu Asp Cys Pro Asn Pro Glu Glu Tyr Asn Leu Asp
                        405                 410                 415 gag cca aat gca gaa agt gat tac aca tat agc agc tcc tat gaa caa          1296
Glu Pro Asn Ala Glu Ser Asp Tyr Thr Tyr Ser Ser Ser Tyr Glu Gln
            420                 425                 430 ttc aat ggt gaa ttg cca aat gga cga cat aaa att ccc gag tca cag          1344
Phe Asn Gly Glu Leu Pro Asn Gly Arg His Lys Ile Pro Glu Ser Gln
        435                 440                 445 ttc cca gag ttt tcc acc tcg ttg ttc tct gga tcc tta gaa cct gtg          1392
Phe Pro Glu Phe Ser Thr Ser Leu Phe Ser Gly Ser Leu Glu Pro Val
    450                 455                 460 gcc tgc ggc tct gtg ctt tct gag gga tca cca ctt act gag caa gag          1440
Ala Cys Gly Ser Val Leu Ser Glu Gly Ser Pro Leu Thr Glu Gln Glu
465                 470                 475                 480 gag agc agt cca tcc cat gac aga agc aga acg gtt tca gcc tcc agt          1488
Glu Ser Ser Pro Ser His Asp Arg Ser Arg Thr Val Ser Ala Ser Ser
                485                 490                 495 act ggg gat ttg cca aaa gca aaa acc cgg gca gct gac ttg ttg gtg          1536
Thr Gly Asp Leu Pro Lys Ala Lys Thr Arg Ala Ala Asp Leu Leu Val
            500                 505                 510 aat ccc ctg gat ccg cgg aat cga gat aaa att aga gta aaa att gct          1584
Asn Pro Leu Asp Pro Arg Asn Arg Asp Lys Ile Arg Val Lys Ile Ala
        515                 520                 525 gac ctg gga aat gct tgt tgg gtg cat aaa cac ttc acg gaa gac atc          1632
Asp Leu Gly Asn Ala Cys Trp Val His Lys His Phe Thr Glu Asp Ile
    530                 535                 540 cag acg cgt cag tac cgc tcc ata gag gtt tta ata gga gcg ggg tac          1680
Gln Thr Arg Gln Tyr Arg Ser Ile Glu Val Leu Ile Gly Ala Gly Tyr
545                 550                 555                 560 agc acc cct gcg gac atc tgg agc acg gcg tgt atg gca ttt gag ctg          1728
Ser Thr Pro Ala Asp Ile Trp Ser Thr Ala Cys Met Ala Phe Glu Leu
                565                 570                 575 gca acg gga gat tat ttg ttt gaa cca cat tct ggg gaa gac tat tcc          1776
Ala Thr Gly Asp Tyr Leu Phe Glu Pro His Ser Gly Glu Asp Tyr Ser
            580                 585                 590 aga gac gaa gac cac ata gcc cac atc ata gag ctg cta ggc agt att          1824
Arg Asp Glu Asp His Ile Ala His Ile Ile Glu Leu Leu Gly Ser Ile
        595                 600                 605 cca agg cac ttt gct cta tct gga aaa tat tct cgg gaa ttc ttc aat          1872
Pro Arg His Phe Ala Leu Ser Gly Lys Tyr Ser Arg Glu Phe Phe Asn
    610                 615                 620 cgc aga gga gaa ctg cga cac atc acc aag ctg aag ccc tgg agc ctc          1920
Arg Arg Gly Glu Leu Arg His Ile Thr Lys Leu Lys Pro Trp Ser Leu
625                 630                 635                 640 ttt gat gta ctt gtg gaa aag tat ggc tgg ccc cat gaa gat gct gca          1968
Phe Asp Val Leu Val Glu Lys Tyr Gly Trp Pro His Glu Asp Ala Ala
                645                 650                 655 cag ttt aca gat ttc ctg atc ccg atg tta gaa atg gtt cca gaa aaa          2016
Gln Phe Thr Asp Phe Leu Ile Pro Met Leu Glu Met Val Pro Glu Lys
            660                 665                 670 cga gcc tca gct ggc gaa tgt cgg cat cct tgg ttg aat tct              2058
Arg Ala Ser Ala Gly Glu Cys Arg His Pro Trp Leu Asn Ser
        675                 680                 685

<210> SEQ ID NO 4
<211> LENGTH: 686
<212> TYPE: PRT
<213> ORGANISM: Homo sapiens
```

<400> SEQUENCE: 4

```
Met Ser Val Asn Ser Glu Lys Ser Ser Ser Glu Arg Pro Glu Pro
1               5                   10                  15

Gln Gln Lys Ala Pro Leu Val Pro Pro Pro Pro Pro Pro Pro Pro
            20                  25                  30

Pro Pro Pro Pro Leu Pro Asp Pro Thr Pro Glu Pro Glu Glu Glu
                35                  40                  45

Ile Leu Gly Ser Asp Asp Glu Gln Glu Asp Pro Ala Asp Tyr Cys
        50                  55                  60

Lys Gly Gly Tyr His Pro Val Lys Ile Gly Asp Leu Phe Asn Gly Arg
65                  70                  75                  80

Tyr His Val Ile Arg Lys Leu Gly Trp Gly His Phe Ser Thr Val Trp
                85                  90                  95

Leu Cys Trp Asp Met Gln Gly Lys Arg Phe Val Ala Met Lys Val Val
            100                 105                 110

Lys Ser Ala Gln His Tyr Thr Glu Thr Ala Leu Asp Glu Ile Lys Leu
            115                 120                 125

Leu Lys Cys Val Arg Glu Ser Asp Pro Ser Asp Pro Asn Lys Asp Met
130                 135                 140

Val Val Gln Leu Ile Asp Asp Phe Lys Ile Ser Gly Met Asn Gly Ile
145                 150                 155                 160

His Val Cys Met Val Phe Glu Val Leu Gly His His Leu Leu Lys Trp
                165                 170                 175

Ile Ile Lys Ser Asn Tyr Gln Gly Leu Pro Val Arg Cys Val Lys Ser
            180                 185                 190

Ile Ile Arg Gln Val Leu Gln Gly Leu Asp Tyr Leu His Ser Lys Cys
            195                 200                 205

Lys Ile Ile His Thr Asp Ile Lys Pro Glu Asn Ile Leu Met Cys Val
            210                 215                 220

Asp Asp Ala Tyr Val Arg Arg Met Ala Ala Glu Pro Glu Trp Gln Lys
225                 230                 235                 240

Ala Gly Ala Pro Pro Ser Gly Ser Ala Val Ser Thr Ala Pro Gln
            245                 250                 255

Gln Lys Pro Ile Gly Lys Ile Ser Lys Asn Lys Lys Lys Leu Lys
            260                 265                 270

Lys Lys Gln Lys Arg Gln Ala Glu Leu Leu Glu Lys Arg Leu Gln Glu
            275                 280                 285

Ile Glu Glu Leu Glu Arg Glu Ala Glu Arg Lys Ile Ile Glu Glu Asn
            290                 295                 300

Ile Thr Ser Ala Ala Pro Ser Asn Asp Gln Asp Gly Glu Tyr Cys Pro
305                 310                 315                 320

Glu Val Lys Leu Lys Thr Thr Gly Leu Glu Glu Ala Glu Ala Glu
            325                 330                 335

Thr Ala Lys Asp Asn Gly Glu Ala Glu Asp Gln Glu Lys Glu Asp
            340                 345                 350

Ala Glu Lys Glu Asn Ile Glu Lys Asp Glu Asp Val Asp Gln Glu
            355                 360                 365

Leu Ala Asn Ile Asp Pro Thr Trp Ile Glu Ser Pro Lys Thr Asn Gly
            370                 375                 380

His Ile Glu Asn Gly Pro Phe Ser Leu Glu Gln Gln Leu Asp Asp Glu
385                 390                 395                 400

Asp Asp Asp Glu Glu Asp Cys Pro Asn Pro Glu Glu Tyr Asn Leu Asp
```

```
                        405                 410                 415
Glu Pro Asn Ala Glu Ser Asp Tyr Thr Tyr Ser Ser Tyr Glu Gln
            420                 425                 430

Phe Asn Gly Glu Leu Pro Asn Gly Arg His Lys Ile Pro Glu Ser Gln
        435                 440                 445

Phe Pro Glu Phe Ser Thr Ser Leu Phe Ser Gly Ser Leu Glu Pro Val
    450                 455                 460

Ala Cys Gly Ser Val Leu Ser Glu Gly Ser Pro Leu Thr Glu Gln Glu
465                 470                 475                 480

Glu Ser Ser Pro Ser His Asp Arg Ser Arg Thr Val Ser Ala Ser Ser
                485                 490                 495

Thr Gly Asp Leu Pro Lys Ala Lys Thr Arg Ala Ala Asp Leu Leu Val
            500                 505                 510

Asn Pro Leu Asp Pro Arg Asn Arg Asp Lys Ile Arg Val Lys Ile Ala
        515                 520                 525

Asp Leu Gly Asn Ala Cys Trp Val His Lys His Phe Thr Glu Asp Ile
    530                 535                 540

Gln Thr Arg Gln Tyr Arg Ser Ile Glu Val Leu Ile Gly Ala Gly Tyr
545                 550                 555                 560

Ser Thr Pro Ala Asp Ile Trp Ser Thr Ala Cys Met Ala Phe Glu Leu
                565                 570                 575

Ala Thr Gly Asp Tyr Leu Phe Glu Pro His Ser Gly Glu Asp Tyr Ser
            580                 585                 590

Arg Asp Glu Asp His Ile Ala His Ile Ile Glu Leu Leu Gly Ser Ile
        595                 600                 605

Pro Arg His Phe Ala Leu Ser Gly Lys Tyr Ser Arg Glu Phe Phe Asn
    610                 615                 620

Arg Arg Gly Glu Leu Arg His Ile Thr Lys Leu Lys Pro Trp Ser Leu
625                 630                 635                 640

Phe Asp Val Leu Val Glu Lys Tyr Gly Trp Pro His Glu Asp Ala Ala
                645                 650                 655

Gln Phe Thr Asp Phe Leu Ile Pro Met Leu Glu Met Val Pro Glu Lys
            660                 665                 670

Arg Ala Ser Ala Gly Glu Cys Arg His Pro Trp Leu Asn Ser
        675                 680                 685

<210> SEQ ID NO 5
<211> LENGTH: 29
<212> TYPE: PRT
<213> ORGANISM: Artificial
<220> FEATURE:
<223> OTHER INFORMATION: a substrate polypeptide for SRPK

<400> SEQUENCE: 5

Arg Ser Pro Ser Tyr Gly Arg Ser Arg Ser Arg Ser Arg Ser Arg Ser
1               5                   10                  15

Arg Ser Arg Ser Arg Ser Asn Ser Arg Ser Arg Ser Tyr
            20                  25
```